United States Patent
Kim et al.

(10) Patent No.: US 10,816,809 B2
(45) Date of Patent: Oct. 27, 2020

(54) HOLOGRAPHIC IN-FIELD ILLUMINATOR

(71) Applicant: FACEBOOK TECHNOLOGIES, LLC, Menlo Park, CA (US)

(72) Inventors: Ganghun Kim, Midvale, UT (US); Andrew Maimone, Duvall, WA (US); Alexander Jobe Fix, Seattle, WA (US); Robert Dale Cavin, Seattle, WA (US); Hee Yoon Lee, Bellevue, WA (US); Matthieu Charles Raoul Leibovici, Seattle, WA (US); Brian Wheelwright, Sammamish, WA (US); Douglas Robert Lanman, Bellevue, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/222,990

(22) Filed: Dec. 17, 2018

(65) Prior Publication Data
US 2020/0192097 A1 Jun. 18, 2020

(51) Int. Cl.
*G03B 17/00* (2006.01)
*G02B 27/01* (2006.01)
*G03H 1/04* (2006.01)
*G06T 7/73* (2017.01)

(52) U.S. Cl.
CPC ..... *G02B 27/0172* (2013.01); *G02B 27/0179* (2013.01); *G03H 1/0402* (2013.01); *G06T 7/74* (2017.01); *G02B 2027/0174* (2013.01); *G02B 2027/0187* (2013.01); *G03H 2001/0413* (2013.01); *G03H 2001/0415* (2013.01); *G06T 2207/30201* (2013.01)

(58) Field of Classification Search
USPC .......................................................... 396/51
See application file for complete search history.

(56) References Cited

U.S. PATENT DOCUMENTS

| 3,658,403 A | 4/1972 | Greenaway et al. |
| 3,941,450 A | 3/1976 | Spitz et al. |
| 4,701,005 A | 10/1987 | Noguchi |
| 2010/0157400 A1* | 6/2010 | Dimov ............... G02B 27/0172 359/13 |
| 2011/0109880 A1* | 5/2011 | Nummela ............. A61B 3/113 351/210 |

(Continued)

OTHER PUBLICATIONS

Facebook Technologies, LLC, International Search Report and Written Opinion, PCT/US2019/066758, dated Mar. 31, 2020, 12 pgs.

*Primary Examiner* — Rodney E Fuller
(74) *Attorney, Agent, or Firm* — Morgan, Lewis & Bockius LLP

(57) ABSTRACT

An eye-tracking system includes a holographic illuminator and a detector. The holographic illuminator includes a light source configured to provide light and a holographic medium optically coupled with the light source. The holographic medium is configured to receive the light provided from the light source and concurrently project a plurality of separate light patterns toward an eye. The detector is configured to detect a reflection of at least a subset of the plurality of separate light patterns, reflected off the eye, for determining a location of a pupil of the eye. Also disclosed is a method for determining a location of a pupil of an eye with the eye-tracking system that includes the holographic illuminator.

20 Claims, 24 Drawing Sheets

(56) References Cited

U.S. PATENT DOCUMENTS

| | | | |
|---|---|---|---|
| 2014/0232651 A1* | 8/2014 | Kress | G02B 27/0172 345/158 |
| 2016/0041384 A1* | 2/2016 | Robbins | G02B 27/017 345/156 |
| 2016/0085300 A1* | 3/2016 | Robbins | G06F 3/013 345/633 |
| 2016/0209657 A1* | 7/2016 | Popovich | G02B 27/017 |
| 2016/0252742 A1* | 9/2016 | Wakabayashi | G02B 27/4227 345/8 |
| 2016/0349514 A1* | 12/2016 | Alexander | G02B 5/32 |
| 2017/0082858 A1* | 3/2017 | Klug | A61B 3/14 |
| 2017/0123526 A1 | 5/2017 | Trail et al. | |
| 2017/0227764 A1* | 8/2017 | Kim | G02B 6/00 |
| 2018/0203234 A1* | 7/2018 | Fiess | G02B 27/017 |
| 2018/0275409 A1* | 9/2018 | Gao | H04N 13/344 13/344 |
| 2018/0332275 A1* | 11/2018 | Gruhlke | H04N 13/383 |
| 2019/0258062 A1* | 8/2019 | Aleem | G02B 27/0172 |

* cited by examiner

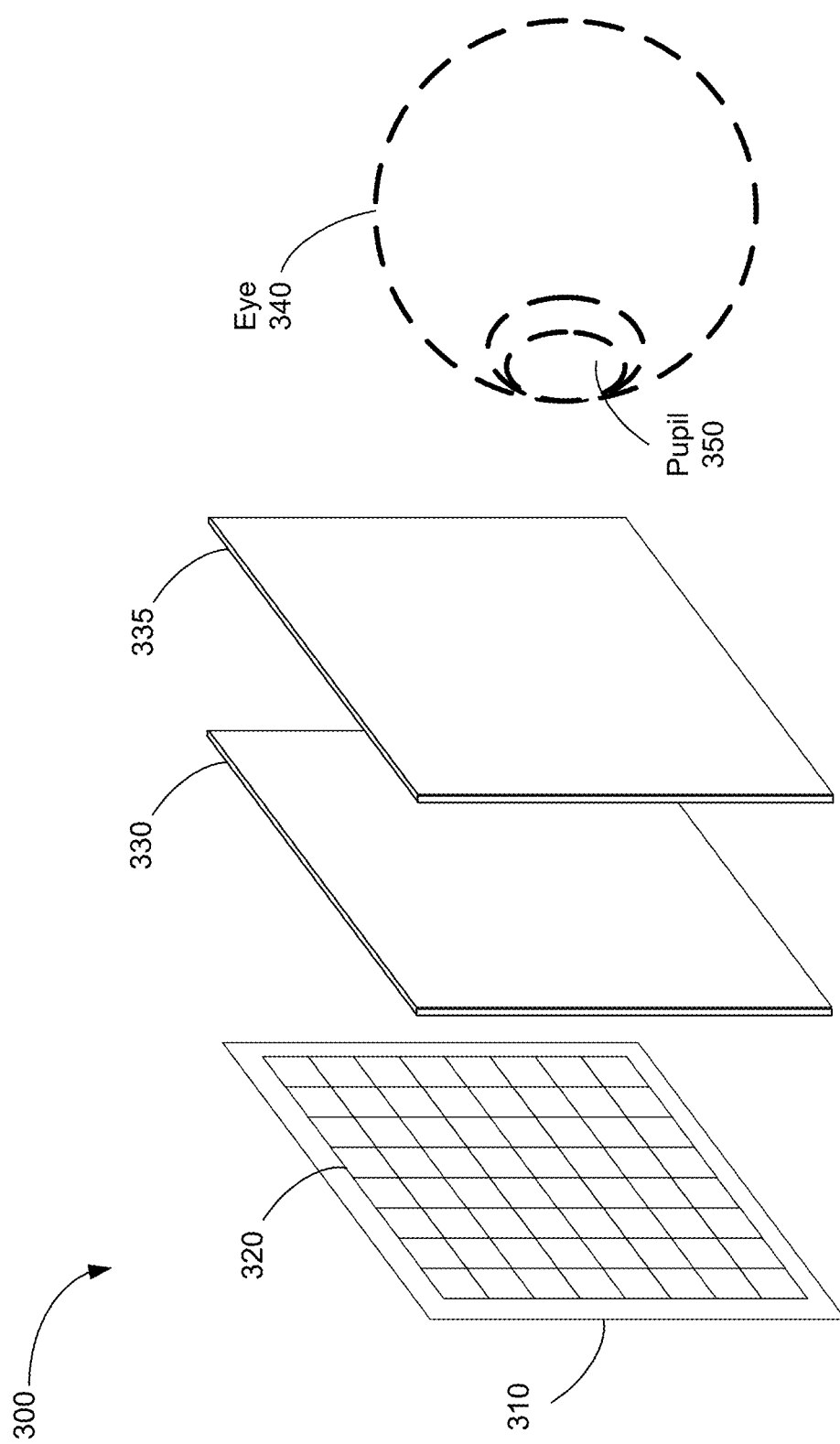

HOLOGRAPHIC IN-FIELD ILLUMINATOR

RELATED APPLICATIONS

This application is related to U.S. patent application Ser. No. 16/222,993, entitled "Wide-Field Holographic Pattern Generation for Head-Mounted Display (HMD) Eye Tracking" filed Dec. 17, 2018, U.S. patent application Ser. No. 16/222,997, entitled "Holographic Pattern Generation for Head-Mounted Display (HMD) Eye Tracking Using a Lens Array" filed Dec. 17, 2018, U.S. patent application Ser. No. 16/223,023, entitled "Holographic Pattern Generation for Head-Mounted Display (HMD) Eye Tracking Using a Prism Array" filed Dec. 17, 2018, U.S. patent application Ser. No. 16/223,026, entitled "Holographic Pattern Generation for Head-Mounted Display (HMD) Eye Tracking Using an Array of Parabolic Mirrors" filed Dec. 17, 2018, U.S. patent application Ser. No. 16/223,030, entitled "Holographic Pattern Generation for Head-Mounted Display (HMD) Eye Tracking Using a Diffractive Optical Element" filed Dec. 17, 2018, and U.S. patent application Ser. No. 16/223,033, entitled "Holographic Pattern Generation for Head-Mounted Display (HMD) Eye Tracking Using a Fiber Exposure" filed Dec. 17, 2018. All of these applications are incorporated by reference herein in their entireties.

TECHNICAL FIELD

This relates generally to display devices, and more specifically to head-mounted display devices.

BACKGROUND

Head-mounted display devices (also called herein head-mounted displays or headsets) are gaining popularity as means for providing visual information to a user. For example, the head-mounted display devices are used for virtual reality and augmented reality operations.

However, the size and weight of conventional head-mounted displays have limited applications of head-mounted displays.

SUMMARY

Accordingly, there is a need for head-mounted displays that are compact and light, thereby enhancing the user's virtual-reality and/or augmented reality experience.

In particular, conventional head-mounted display devices (e.g., conventional head-mounted display devices configured for augmented reality operations) project images over a large area around an eye of a user in order to provide a wide field of view in all gaze-directions (e.g., in order to deal with pupil steering). However, projecting images over a large area leads to reduced brightness of the projected images. Compensating for the reduced brightness typically requires a high intensity light source, which is typically large and heavy, and has high power consumption. There is a need for eye-tracking systems for determining a position of a pupil of an eye in order to project images over a reduced area toward the pupil of the eye. Such system, in turn, allows compact, light, and low power-consumption head-mounted displays. In addition, in some cases, the content displayed by the head-mounted displays needs to be updated based on a gaze direction of a user, which also requires eye-tracking systems for determining the position of the pupil of the eye.

One approach to track movements of an eye is to illuminate a surface of the eye, and detect reflections of the illuminated patterns off the surface of the eye (e.g., glints). In order to avoid occluding a field-of-view of a user, the light source for illuminating the surface of the eye is typically positioned away from the field-of view. However, eye tracking with such illumination has challenges, such as having to take into account a variety of eye reliefs, eye lid occlusions, iris sizes and inter pupillary distances of different users. Therefore, there is a need for eye-tracking systems with in-field (e.g., in-field-of-view) illumination without occluding the field-of-view.

The above deficiencies and other problems associated with conventional eye-tracking systems are reduced or eliminated by the disclosed systems with in-field illumination of the eye.

In accordance with some embodiments, an eye-tracking system includes a holographic illuminator that includes a light source configured to provide light and a holographic medium optically coupled with the light source. The holographic medium is configured to receive the light provided from the light source and project a plurality of separate light patterns concurrently toward an eye. The eye-tracking system also includes a detector configured to detect a reflection of at least a subset of the plurality of separate light patterns, reflected off the eye, for determining a location of a pupil of the eye.

In accordance with some embodiments, a head-mounted display device includes one or more optical elements, one or more displays configured to project light through or off of the one or more optical elements, and the eye-tracking system described herein.

In accordance with some embodiments, a method for determining a location of a pupil of an eye includes providing light with a light source; receiving, with a holographic medium optically coupled with the light source, the light provided by the light source; and projecting, with the holographic medium, a plurality of separate light patterns concurrently toward an eye. The method also includes detecting, with a detector, a reflection of at least a subset of the plurality of separate light patterns reflected off the eye of the wearer. The method further includes determining, based on the reflection of at least the subset of the plurality of separate light patterns reflected off the eye, a location of a pupil of the eye.

In accordance with some embodiments, a method includes providing light from a light source and separating the light into a first portion of the light and a second portion of the light that is spatially separated from the first portion of the light. The method also includes transmitting the first portion of the light through a first set of optical elements to provide a first wide-field beam, transmitting the second portion of the light through a second set of optical elements to provide a second wide-field beam that is spatially separated from the first wide-field beam, and transmitting the second wide-field beam through a third set of optical elements to provide a plurality of separate light patterns. The method further includes concurrently projecting the first wide-field beam and the plurality of separate light patterns onto an optically recordable medium to form a holographic medium.

In accordance with some embodiments, a system for making a holographic medium includes a light source configured to provide light and a beam splitter configured to separate the light into a first portion of the light and a second portion of the light that is spatially separated from the first portion of the light. The system also includes a first set of optical elements configured to transmit the first portion of the light for providing a first wide-field beam, a second set of optical elements configured to transmit the second portion of the light for providing a second wide-field beam, and a third set of optical elements optically coupled with the second set of optical elements and configured to transmit the second wide-field beam for providing a plurality of separate light patterns onto an optically recordable medium for forming the holographic medium.

In accordance with some embodiments, a system for making a holographic medium includes a light source configured to provide light and a beam splitter configured to separate the light into a first portion of the light and a second portion of the light that is spatially separated from the first portion of the light. The system also includes a first set of optical elements configured to transmit the first portion of the light for providing a first wide-field beam onto an optically recordable medium, a second set of optical elements configured to transmit the second portion of the light through for providing a second wide-field beam, and a plurality of lenses optically coupled with the second set of optical elements configured to receive the second wide-field beam and project a plurality of separate light patterns onto the optically recordable medium for forming the holographic medium.

In accordance with some embodiments, a method for making a holographic medium includes providing light from a light source and separating the light into a first portion of the light and a second portion of the light that is spatially separated from the first portion of the light. The method also includes transmitting the first portion of the light through a first set of optical elements to provide a first wide-field beam, transmitting the second portion of the light through a second set of optical elements to provide a second wide-field beam that is spatially separated from the first wide-field beam onto an optically recordable medium, and transmitting the second wide-field beam through a plurality of lenses to provide a plurality of separate light patterns. The method further includes concurrently projecting the first wide-field beam and the plurality of separate light patterns onto the optically recordable medium to form the holographic medium.

In accordance with some embodiments, a system for making a holographic medium includes a light source configured to provide light, and a beam splitter configured to separate the light into a first portion of the light and a second portion of the light that is spatially separated from the first portion of the light. The system also includes a first set of optical elements configured to transmit the first portion of the light for providing a first wide-field beam onto an optically recordable medium, a second set of optical elements configured to transmit the second portion of the light for providing a second wide-field beam, and a plurality of prisms optically coupled with the second set of optical elements and configured to receive the second wide-field beam and project a plurality of separate light patterns onto the optically recordable medium for forming the holographic medium.

In accordance with some embodiments, a method for making a holographic medium includes providing light from a light source, and separating the light into a first portion of the light and a second portion of the light that is spatially separated from the first portion of the light. The method also includes transmitting the first portion of the light through a first set of optical elements to provide a first wide-field beam, transmitting the second portion of the light through a second set of optical elements to provide a second wide-field beam that is spatially separated from the first wide-field beam onto an optically recordable medium, and transmitting the second wide-field beam through a plurality of prisms to provide a plurality of separate light patterns. The method further includes concurrently projecting the first wide-field beam and the plurality of separate light patterns onto the optically recordable medium to form the holographic medium.

In accordance with some embodiments, a system for making a holographic medium includes a light source configured to provide light and a beam splitter configured to separate the light into a first portion of the light and a second portion of the light that is spatially separated from the first portion of the light. The system also includes a first set of optical elements configured to transmit the first portion of the light for providing a first wide-field beam onto an optically recordable medium, a second set of optical elements configured to transmit the second portion of the light for providing a second wide-field beam, and a plurality of parabolic reflectors optically coupled with the second set of optical elements and configured to receive the second wide-field beam and project a plurality of separate light patterns onto the optically recordable medium for forming the holographic medium.

In accordance with some embodiments, a method for making a holographic medium includes providing light from a light source, and separating the light into a first portion of the light and a second portion of the light that is spatially separated from the first portion of the light. The method also includes transmitting the first portion of the light through a first set of optical elements to provide a first wide-field beam, transmitting the second portion of the light through a second set of optical elements to provide a second wide-field beam that is spatially separated from the first wide-field beam onto an optically recordable medium, and reflecting the second wide-field beam with a plurality of parabolic reflectors to provide a plurality of separate light patterns. The method further includes concurrently projecting the first wide-field beam and reflecting the plurality of separate light patterns onto the optically recordable medium to form the holographic medium.

In accordance with some embodiments, a system for making a holographic medium includes a light source configured to provide light and a beam splitter configured to separate the light into a first portion of the light and a second portion of the light that is spatially separated from the first portion of the light. The system also includes a first set of optical elements configured to transmit the first portion of the light for providing a first wide-field beam onto an optically recordable medium and one or more diffractive optical elements configured to receive the second portion of the light and project a plurality of separate light patterns onto the optically recordable medium for forming the holographic medium.

In accordance with some embodiments, a method for making a holographic medium includes providing light from a light source and separating the light into a first portion of the light and a second portion of the light that is spatially separated from the first portion of the light. The method also includes transmitting the first portion of the light through a first set of optical elements to provide a first wide-field beam, transmitting the second portion of the light through one or more diffractive optical elements to provide a plurality of separate light patterns, and concurrently projecting the first wide-field beam and the plurality of separate light patterns onto the optically recordable medium to form the holographic medium.

In accordance with some embodiments, a system for making a holographic medium includes a light source configured to provide light and a beam splitter configured to separate the light into a first portion of the light and a second portion of the light that is spatially separated from the first portion of the light. The system also includes a first set of optical elements configured to transmit the first portion of the light for providing a first wide-field beam onto an optically recordable medium and a plurality of optical fibers configured to receive the second portion of the light and project a plurality of separate light patterns onto the optically recordable medium for forming the holographic medium.

In accordance with some embodiments, a method for making a holographic medium includes providing light from a light source and separating the light into a first portion of the light and a second portion of the light that is spatially separated from the first portion of the light. The method also includes transmitting the first portion of the light through a first set of optical elements to provide a first wide-field beam, transmitting the second portion of the light through a plurality of optical fibers to provide a plurality of separate light patterns, and concurrently projecting the first wide-field beam and the plurality of separate light patterns onto the optically recordable medium to form the holographic medium.

In accordance with some embodiments, a holographic medium is made by any of the methods described herein.

Thus, the disclosed embodiments provide eye-tracking systems and eye-tracking methods based on holographic media, and devices and methods for making holographic media.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIG. 3 is an isometric view of a display device in accordance with some embodiments.

FIG. 4D is a schematic diagram illustrating a holographic illuminator shown in

FIG. 4A.

Figure 1:
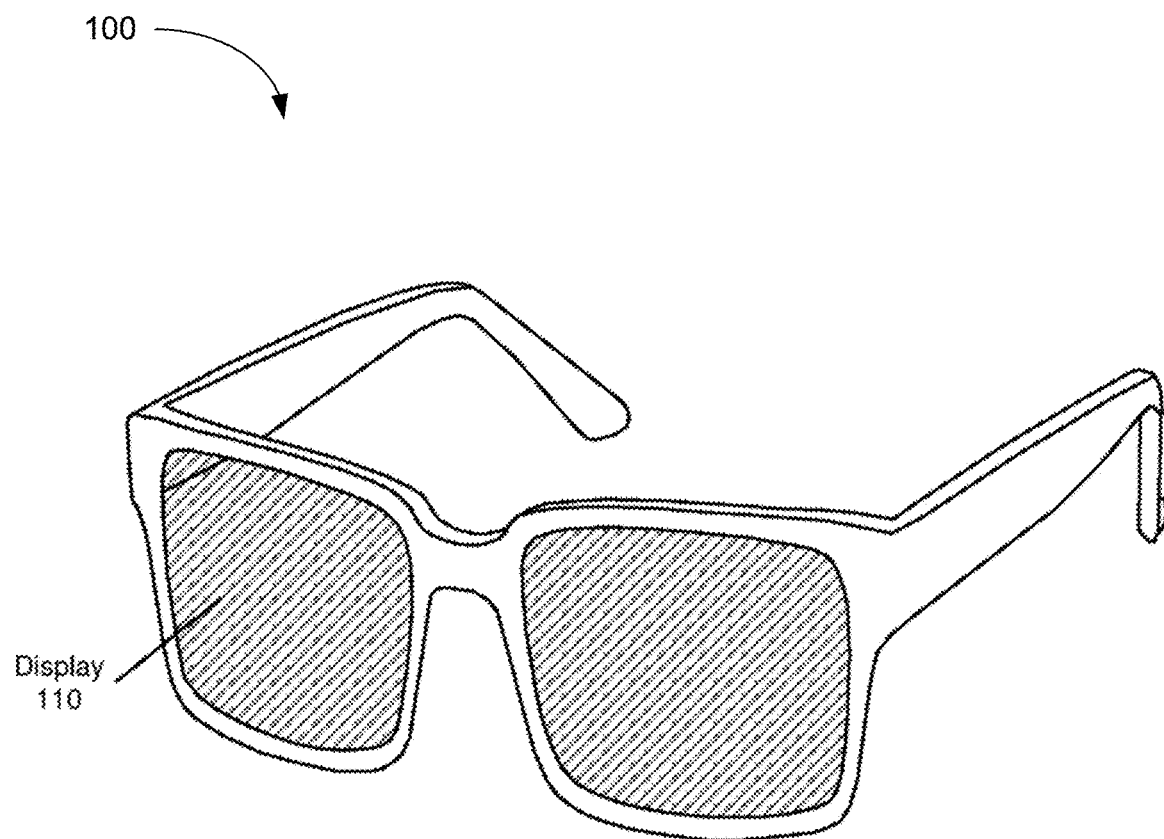
FIG. 1 is a perspective view of a display device in accordance with some embodiments.

These figures are not drawn to scale unless indicated otherwise.

DETAILED DESCRIPTION

Eye-tracking systems with in-field illumination provide accurate and reliable determination of a position of a pupil of an eye because the illumination is projected toward the eye in the direction of the field-of-view of the eye. Such illumination projects glints in the center region of the eye, which can be analyzed for accurate determination of the position of the pupil of the eye. The disclosed embodiments provide (i) holographic illuminators and (ii) methods and systems for making such holographic illuminators that provide in-field illumination. In addition, such holographic illuminators have reduced or no occlusion of the field-of-view of the eye of the user.

In some embodiments, the holographic illuminator includes a light source positioned away from the field-of-view of an eye projecting a non-visible (e.g., an infrared (IR)

or near-infrared (NIR)) light toward a holographic medium (e.g., a holographic film) positioned in-field of the eye.

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are used only to distinguish one element from another. For example, a first surface could be termed a second surface, and, similarly, a second surface could be termed a first surface, without departing from the scope of the various described embodiments. The first surface and the second surface are both surfaces, but they are not the same surface.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "exemplary" is used herein in the sense of "serving as an example, instance, or illustration" and not in the sense of "representing the best of its kind."

FIG. 1 illustrates display device 100 in accordance with some embodiments. In some embodiments, display device 100 is configured to be worn on a head of a user (e.g., by having the form of spectacles or eyeglasses, as shown in FIG. 1) or to be included as part of a helmet that is to be worn by the user. When display device 100 is configured to be worn on a head of a user or to be included as part of a helmet, display device 100 is called a head-mounted display. Alternatively, display device 100 is configured for placement in proximity of an eye or eyes of the user at a fixed location, without being head-mounted (e.g., display device 100 is mounted in a vehicle, such as a car or an airplane, for placement in front of an eye or eyes of the user). As shown in FIG. 1, display device 100 includes display 110. Display 110 is configured for presenting visual contents (e.g., augmented reality contents, virtual reality contents, mixed reality contents, or any combination thereof) to a user.

Figure 2:
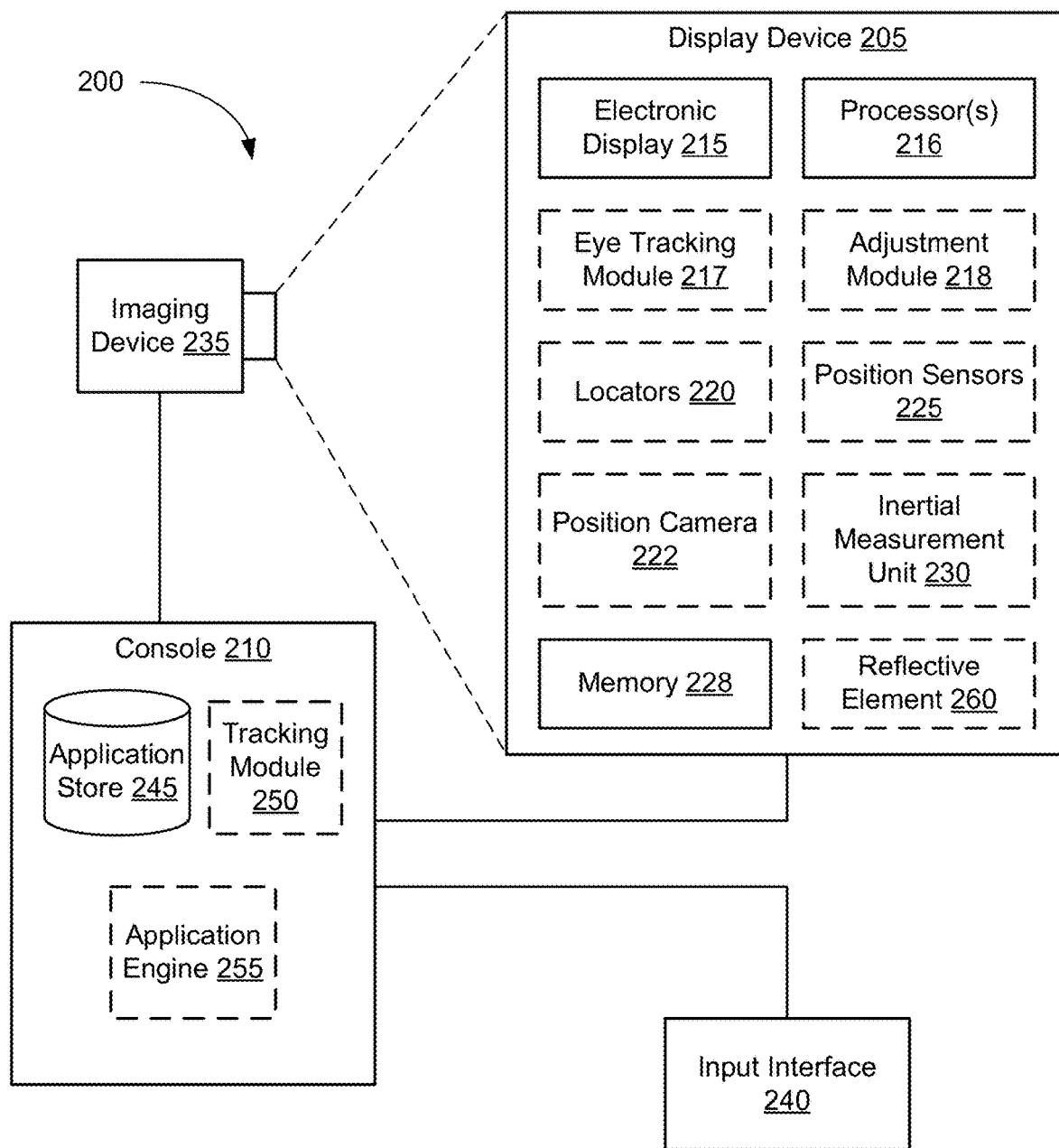
FIG. 2 is a block diagram of a system including a display device in accordance with some embodiments.

In some embodiments, display device 100 includes one or more components described herein with respect to FIG. 2. In some embodiments, display device 100 includes additional components not shown in FIG. 2.

FIG. 2 is a block diagram of system 200 in accordance with some embodiments. The system 200 shown in FIG. 2 includes display device 205 (which corresponds to display device 100 shown in FIG. 1), imaging device 235, and input interface 250 that are each coupled to console 210. While FIG. 2 shows an example of system 200 including one display device 205, imaging device 235, and input interface 250, in other embodiments, any number of these components may be included in system 200. For example, there may be multiple display devices 205 each having associated input interface 250 and being monitored by one or more imaging devices 235, with each display device 205, input interface 250, and imaging devices 235 communicating with console 210. In alternative configurations, different and/or additional components may be included in system 200. For example, in some embodiments, console 210 is connected via a network (e.g., the Internet) to system 200 or is self-contained as part of display device 205 (e.g., physically located inside display device 205). In some embodiments, display device 205 is used to create mixed reality by adding in a view of the real surroundings. Thus, display device 205 and system 200 described here can deliver augmented reality, virtual reality, and mixed reality.

In some embodiments, as shown in FIG. 1, display device 205 is a head-mounted display that presents media to a user. Examples of media presented by display device 205 include one or more images, video, audio, or some combination thereof. In some embodiments, audio is presented via an external device (e.g., speakers and/or headphones) that receives audio information from display device 205, console 210, or both, and presents audio data based on the audio information. In some embodiments, display device 205 immerses a user in an augmented environment.

In some embodiments, display device 205 also acts as an augmented reality (AR) headset. In these embodiments, display device 205 augments views of a physical, real-world environment with computer-generated elements (e.g., images, video, sound, etc.). Moreover, in some embodiments, display device 205 is able to cycle between different types of operation. Thus, display device 205 operate as a virtual reality (VR) device, an augmented reality (AR) device, as glasses or some combination thereof (e.g., glasses with no optical correction, glasses optically corrected for the user, sunglasses, or some combination thereof) based on instructions from application engine 255.

Display device 205 includes electronic display 215, one or more processors 216, eye tracking module 217, adjustment module 218, one or more locators 220, one or more position sensors 225, one or more position cameras 222, memory 228, inertial measurement unit (IMU) 230, one or more reflective elements 260 or a subset or superset thereof (e.g., display device 205 with electronic display 215, one or more processors 216, and memory 228, without any other listed components). Some embodiments of display device 205 have different modules than those described here. Similarly, the functions can be distributed among the modules in a different manner than is described here.

One or more processors 216 (e.g., processing units or cores) execute instructions stored in memory 228. Memory 228 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 228, or alternately the non-volatile memory device(s) within memory 228, includes a non-transitory computer readable storage medium. In some embodiments, memory 228 or the computer readable storage medium of memory 228 stores programs, modules and data structures, and/or instructions for displaying one or more images on electronic display 215.

Electronic display 215 displays images to the user in accordance with data received from console 210 and/or processor(s) 216. In various embodiments, electronic display 215 may comprise a single adjustable display element or multiple adjustable display elements (e.g., a display for each eye of a user). In some embodiments, electronic display 215 is configured to display images to the user by projecting the images onto one or more reflective elements 260.

In some embodiments, the display element includes one or more light emission devices and a corresponding array of spatial light modulators. A spatial light modulator is an array of electro-optic pixels, opto-electronic pixels, some other array of devices that dynamically adjust the amount of light transmitted by each device, or some combination thereof. These pixels are placed behind one or more lenses. In some embodiments, the spatial light modulator is an array of liquid crystal based pixels in an LCD (a Liquid Crystal Display). Examples of the light emission devices include: an organic light emitting diode, an active-matrix organic light-emitting diode, a light emitting diode, some type of device capable of being placed in a flexible display, or some combination thereof. The light emission devices include devices that are capable of generating visible light (e.g., red, green, blue, etc.) used for image generation. The spatial light modulator is configured to selectively attenuate individual light emission devices, groups of light emission devices, or some combination thereof. Alternatively, when the light emission devices are configured to selectively attenuate individual emission devices and/or groups of light emission devices, the display element includes an array of such light emission devices without a separate emission intensity array. In some embodiments, electronic display 215 projects images to one or more reflective elements 260, which reflect at least a portion of the light toward an eye of a user.

One or more lenses direct light from the arrays of light emission devices (optionally through the emission intensity arrays) to locations within each eyebox and ultimately to the back of the user's retina(s). An eyebox is a region that is occupied by an eye of a user located proximity to display device 205 (e.g., a user wearing display device 205) for viewing images from display device 205. In some cases, the eyebox is represented as a 10 mm×10 mm square. In some embodiments, the one or more lenses include one or more coatings, such as anti-reflective coatings.

In some embodiments, the display element includes an infrared (IR) detector array that detects IR light that is retro-reflected from the retinas of a viewing user, from the surface of the corneas, lenses of the eyes, or some combination thereof. The IR detector array includes an IR sensor or a plurality of IR sensors that each correspond to a different position of a pupil of the viewing user's eye. In alternate embodiments, other eye tracking systems may also be employed. As used herein, IR refers to light with wavelengths ranging from 700 nm to 1 mm including near infrared (NIR) ranging from 750 nm to 1500 nm.

Eye tracking module 217 determines locations of each pupil of a user's eyes. In some embodiments, eye tracking module 217 instructs electronic display 215 to illuminate the eyebox with IR light (e.g., via IR emission devices in the display element).

A portion of the emitted IR light will pass through the viewing user's pupil and be retro-reflected from the retina toward the IR detector array, which is used for determining the location of the pupil. Alternatively, the reflection off of the surfaces of the eye is used to also determine location of the pupil. The IR detector array scans for retro-reflection and identifies which IR emission devices are active when retro-reflection is detected. Eye tracking module 217 may use a tracking lookup table and the identified IR emission devices to determine the pupil locations for each eye. The tracking lookup table maps received signals on the IR detector array to locations (corresponding to pupil locations) in each eyebox. In some embodiments, the tracking lookup table is generated via a calibration procedure (e.g., user looks at various known reference points in an image and eye tracking module 217 maps the locations of the user's pupil while looking at the reference points to corresponding signals received on the IR tracking array). As mentioned above, in some embodiments, system 200 may use other eye tracking systems than the embedded IR one described herein.

Adjustment module 218 generates an image frame based on the determined locations of the pupils. In some embodiments, this sends a discrete image to the display that will tile subimages together thus a coherent stitched image will appear on the back of the retina. Adjustment module 218 adjusts an output (i.e. the generated image frame) of electronic display 215 based on the detected locations of the pupils. Adjustment module 218 instructs portions of electronic display 215 to pass image light to the determined locations of the pupils. In some embodiments, adjustment module 218 also instructs the electronic display to not pass image light to positions other than the determined locations of the pupils. Adjustment module 218 may, for example, block and/or stop light emission devices whose image light falls outside of the determined pupil locations, allow other light emission devices to emit image light that falls within the determined pupil locations, translate and/or rotate one or more display elements, dynamically adjust curvature and/or refractive power of one or more active lenses in the lens (e.g., microlens) arrays, or some combination thereof.

Optional locators 220 are objects located in specific positions on display device 205 relative to one another and relative to a specific reference point on display device 205. A locator 220 may be a light emitting diode (LED), a corner cube reflector, a reflective marker, a type of light source that contrasts with an environment in which display device 205 operates, or some combination thereof. In embodiments where locators 220 are active (i.e., an LED or other type of light emitting device), locators 220 may emit light in the visible band (e.g., about 500 nm to 750 nm), in the infrared band (e.g., about 750 nm to 1 mm), in the ultraviolet band (about 100 nm to 500 nm), some other portion of the electromagnetic spectrum, or some combination thereof.

In some embodiments, locators 220 are located beneath an outer surface of display device 205, which is transparent to the wavelengths of light emitted or reflected by locators 220 or is thin enough to not substantially attenuate the wavelengths of light emitted or reflected by locators 220. Additionally, in some embodiments, the outer surface or other portions of display device 205 are opaque in the visible band of wavelengths of light. Thus, locators 220 may emit light in the IR band under an outer surface that is transparent in the IR band but opaque in the visible band.

IMU 230 is an electronic device that generates calibration data based on measurement signals received from one or more position sensors 225. Position sensor 225 generates one or more measurement signals in response to motion of display device 205. Examples of position sensors 225 include: one or more accelerometers, one or more gyroscopes, one or more magnetometers, another suitable type of sensor that detects motion, a type of sensor used for error correction of IMU 230, or some combination thereof. Position sensors 225 may be located external to IMU 230, internal to IMU 230, or some combination thereof.

Based on the one or more measurement signals from one or more position sensors 225, IMU 230 generates first calibration data indicating an estimated position of display device 205 relative to an initial position of display device 205. For example, position sensors 225 include multiple accelerometers to measure translational motion (forward/back, up/down, left/right) and multiple gyroscopes to measure rotational motion (e.g., pitch, yaw, roll). In some embodiments, IMU 230 rapidly samples the measurement signals and calculates the estimated position of display device 205 from the sampled data. For example, IMU 230 integrates the measurement signals received from the accelerometers over time to estimate a velocity vector and integrates the velocity vector over time to determine an estimated position of a reference point on display device 205. Alternatively, IMU 230 provides the sampled measurement signals to console 210, which determines the first calibration data. The reference point is a point that may be used to describe the position of display device 205. While the reference point may generally be defined as a point in space; however, in practice the reference point is defined as a point within display device 205 (e.g., a center of IMU 230).

In some embodiments, IMU 230 receives one or more calibration parameters from console 210. As further discussed below, the one or more calibration parameters are used to maintain tracking of display device 205. Based on a received calibration parameter, IMU 230 may adjust one or more IMU parameters (e.g., sample rate). In some embodiments, certain calibration parameters cause IMU 230 to update an initial position of the reference point so it corresponds to a next calibrated position of the reference point. Updating the initial position of the reference point as the next calibrated position of the reference point helps reduce accumulated error associated with the determined estimated position. The accumulated error, also referred to as drift error, causes the estimated position of the reference point to "drift" away from the actual position of the reference point over time.

Imaging device 235 generates calibration data in accordance with calibration parameters received from console 210. Calibration data includes one or more images showing observed positions of locators 220 that are detectable by imaging device 235. In some embodiments, imaging device 235 includes one or more still cameras, one or more video cameras, any other device capable of capturing images including one or more locators 220, or some combination thereof. Additionally, imaging device 235 may include one or more filters (e.g., used to increase signal to noise ratio). Imaging device 235 is configured to optionally detect light emitted or reflected from locators 220 in a field of view of imaging device 235. In embodiments where locators 220 include passive elements (e.g., a retroreflector), imaging device 235 may include a light source that illuminates some or all of locators 220, which retro-reflect the light towards the light source in imaging device 235. Second calibration data is communicated from imaging device 235 to console 210, and imaging device 235 receives one or more calibration parameters from console 210 to adjust one or more imaging parameters (e.g., focal length, focus, frame rate, ISO, sensor temperature, shutter speed, aperture, etc.).

In some embodiments, display device 205 optionally includes one or more reflective elements 260. In some embodiments, electronic display device 205 optionally includes a single reflective element 260 or multiple reflective elements 260 (e.g., a reflective element 260 for each eye of a user). In some embodiments, electronic display device 215 projects computer-generated images on one or more reflective elements 260, which, in turn, reflect the images toward an eye or eyes of a user. The computer-generated images include still images, animated images, and/or a combination thereof. The computer-generated images include objects that appear to be two-dimensional and/or three-dimensional objects. In some embodiments, one or more reflective elements 260 are partially transparent (e.g., the one or more reflective elements 260 have a transmittance of at least 15%, 20%, 25%, 30%, 35%, 50%, 55%, or 50%), which allows transmission of ambient light. In such embodiments, computer-generated images projected by electronic display 215 are superimposed with the transmitted ambient light (e.g., transmitted ambient image) to provide augmented reality images.

Input interface 250 is a device that allows a user to send action requests to console 210. An action request is a request to perform a particular action. For example, an action request may be to start or end an application or to perform a particular action within the application. Input interface 250 may include one or more input devices. Example input devices include: a keyboard, a mouse, a game controller, data from brain signals, data from other parts of the human body, or any other suitable device for receiving action requests and communicating the received action requests to console 210. An action request received by input interface 250 is communicated to console 210, which performs an action corresponding to the action request. In some embodiments, input interface 250 may provide haptic feedback to the user in accordance with instructions received from console 210. For example, haptic feedback is provided when an action request is received, or console 210 communicates instructions to input interface 250 causing input interface 250 to generate haptic feedback when console 210 performs an action.

Console 210 provides media to display device 205 for presentation to the user in accordance with information received from one or more of: imaging device 235, display device 205, and input interface 250. In the example shown in FIG. 2, console 210 includes application store 255, tracking module 250, and application engine 255. Some embodiments of console 210 have different modules than those described in conjunction with FIG. 2. Similarly, the functions further described herein may be distributed among components of console 210 in a different manner than is described here.

When application store 255 is included in console 210, application store 255 stores one or more applications for execution by console 210. An application is a group of instructions, that when executed by a processor, is used for generating content for presentation to the user. Content generated by the processor based on an application may be in response to inputs received from the user via movement of display device 205 or input interface 250. Examples of applications include: gaming applications, conferencing applications, video playback application, or other suitable applications.

When tracking module 250 is included in console 210, tracking module 250 calibrates system 200 using one or more calibration parameters and may adjust one or more calibration parameters to reduce error in determination of the position of display device 205. For example, tracking module 250 adjusts the focus of imaging device 235 to obtain a more accurate position for observed locators on display device 205. Moreover, calibration performed by tracking module 250 also accounts for information received from IMU 230. Additionally, if tracking of display device 205 is lost (e.g., imaging device 235 loses line of sight of at least a threshold number of locators 220), tracking module 250 re-calibrates some or all of system 200.

In some embodiments, tracking module 250 tracks movements of display device 205 using second calibration data from imaging device 235. For example, tracking module 250 determines positions of a reference point of display device 205 using observed locators from the second calibration data and a model of display device 205. In some embodiments, tracking module 250 also determines positions of a reference point of display device 205 using position information from the first calibration data. Additionally, in some embodiments, tracking module 250 may use portions of the first calibration data, the second calibration data, or some combination thereof, to predict a future location of display device 205. Tracking module 250 provides the estimated or predicted future position of display device 205 to application engine 255.

Application engine 255 executes applications within system 200 and receives position information, acceleration information, velocity information, predicted future positions, or some combination thereof of display device 205 from tracking module 250. Based on the received information, application engine 255 determines content to provide to display device 205 for presentation to the user. For example, if the received information indicates that the user has looked to the left, application engine 255 generates content for display device 205 that mirrors the user's movement in an augmented environment. Additionally, application engine 255 performs an action within an application executing on console 210 in response to an action request received from input interface 250 and provides feedback to the user that the action was performed. The provided feedback may be visual or audible feedback via display device 205 or haptic feedback via input interface 250.

FIG. 3 is an isometric view of display device 300 in accordance with some embodiments. In some other embodiments, display device 300 is part of some other electronic display (e.g., a digital microscope, a head-mounted display device, etc.). In some embodiments, display device 300 includes light emission device array 310 and one or more lenses 330. In some embodiments, display device 300 also includes an IR detector array.

Light emission device array 310 emits image light and optional IR light toward the viewing user. Light emission device array 310 may be, e.g., an array of LEDs, an array of microLEDs, an array of OLEDs, or some combination thereof. Light emission device array 310 includes light emission devices 320 that emit light in the visible light (and optionally includes devices that emit light in the IR).

In some embodiments, display device 300 includes an emission intensity array configured to selectively attenuate light emitted from light emission array 310. In some embodiments, the emission intensity array is composed of a plurality of liquid crystal cells or pixels, groups of light emission devices, or some combination thereof. Each of the liquid crystal cells is, or in some embodiments, groups of liquid crystal cells are, addressable to have specific levels of attenuation. For example, at a given time, some of the liquid crystal cells may be set to no attenuation, while other liquid crystal cells may be set to maximum attenuation. In this manner, the emission intensity array is able to control what portion of the image light emitted from light emission device array 310 is passed to the one or more lenses 330. In some embodiments, display device 300 uses an emission intensity array to facilitate providing image light to a location of pupil 350 of eye 350 of a user, and minimize the amount of image light provided to other areas in the eyebox.

One or more lenses 330 receive the modified image light (e.g., attenuated light) from emission intensity array (or directly from emission device array 310), and direct the modified image light to a location of pupil 350.

An optional IR detector array detects IR light that has been retro-reflected from the retina of eye 350, a cornea of eye 350, a crystalline lens of eye 350, or some combination thereof. The IR detector array includes either a single IR sensor or a plurality of IR sensitive detectors (e.g., photodiodes). In some embodiments, the IR detector array is separate from light emission device array 310. In some embodiments, the IR detector array is integrated into light emission device array 310.

In some embodiments, light emission device array 310 and an emission intensity array make up a display element. Alternatively, the display element includes light emission device array 310 (e.g., when light emission device array 310 includes individually adjustable pixels) without the emission intensity array. In some embodiments, the display element additionally includes the IR array. In some embodiments, in response to a determined location of pupil 350, the display element adjusts the emitted image light such that the light output by the display element is refracted by one or more lenses 330 toward the determined location of pupil 350, and not toward other locations in the eyebox.

In some embodiments, display device 300 includes one or more broadband sources (e.g., one or more white LEDs) coupled with a plurality of color filters, in addition to, or instead of, light emission device array 310.

Display device 300 also includes holographic medium 335, which is included in a holographic illuminator.

Figure 4A:
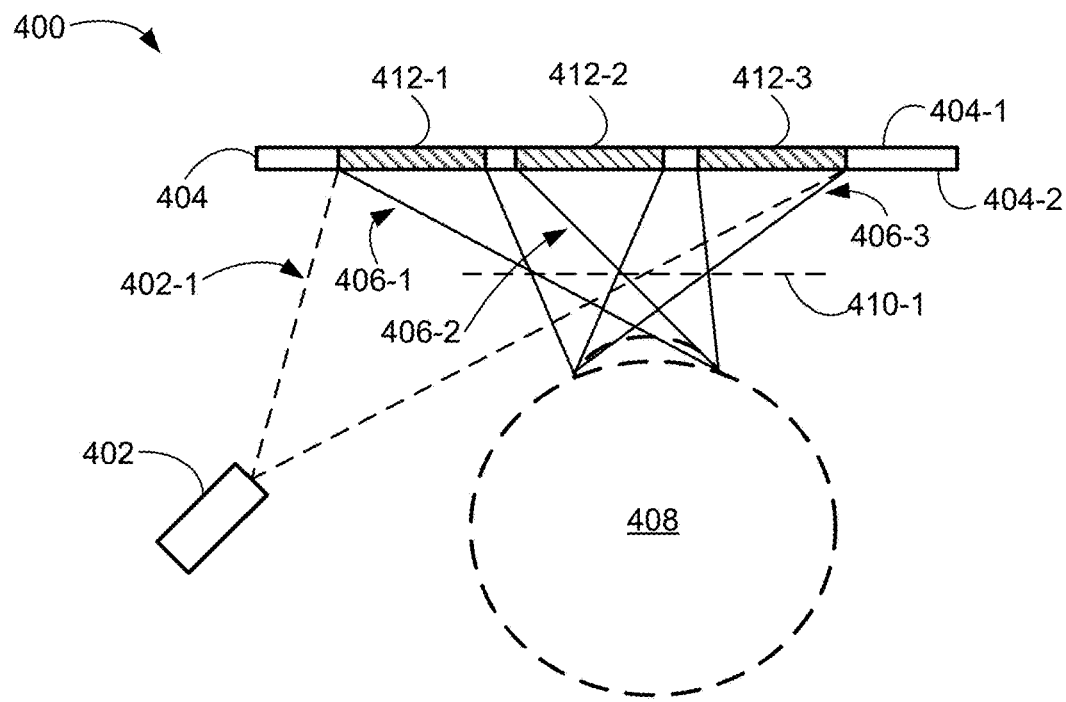
FIG. 4A is a schematic diagram illustrating a holographic illuminator in accordance with some embodiments.

FIG. 4A is a schematic diagram illustrating holographic illuminator 400 in accordance with some embodiments. Holographic illuminator 400 includes light source 402 and holographic medium 404. Holographic medium 404 is a wide-field holographic medium for projecting a plurality of light patterns onto a surface of an eye of a user of a head-mounted display device for eye-tracking purposes. In some cases, a wide-field holographic medium refers to a holographic medium configured to illuminate an area with a characteristic dimension of at least 10 mm (e.g., illuminating an area of at least 10 mm in diameter or length with a plurality of light patterns). In some embodiments, light source 402 is a single-point light source (e.g., a laser or an LED). In some embodiments, light source 402 is a wide-field light source. In some embodiments, light 402-1 provided by light source 402 is collimated light.

In FIG. 4A, light source 402 is located away from an optical axis of holographic medium 404. In some embodiments, light source 402 is located away from an optical axis of a lens (e.g., lens 330 in FIG. 3) of a head-mounted display device. In some embodiments, light source 402 is located away from a field of view of eye 408 (e.g., eye 408 corresponds to an eye of a user of a head-mounted display device). By providing an off-axis illumination, light source 402 does not occlude the field of view of eye 408. In some embodiments, light source 402 is positioned on the optical axis of holographic medium 404.

In FIG. 4A, light 402-1 provided by light source 402 is projected toward holographic medium 404. Holographic medium 404 is a reflection holographic medium having surface 404-1 and surface 404-2 with one or more recorded interference patterns. The one or more recorded interference patterns modify light impinging on recorded interference patterns and project one or more holographic patterns. In FIG. 4A, light 402-1 is received by surface 404-2 of holographic medium 404. Holographic medium 404 includes areas 412-1, 412-2, and 412-3 that are configured to interact with light 402-1 and concurrently direct (e.g., reflect, diffract, etc.) separate light patterns 406-1, 406-2, and 406-3 toward eye 408. In some embodiments, light patterns 406-1, 406-2, and 406-3 convergence on reference plane 410-1 adjacent to eye 408, as shown in FIG. 4A, creating three virtual single-point light sources near eye 408. In FIG. 4A, light patterns 406-1, 406-2, and 406-3 are each projected toward eye 408 at different angles. For example, light pattern 406-1 is directed toward eye 408 at a first angle, light pattern 406-2 is directed toward eye 408 at a second angle, and light pattern 406-3 is directed toward eye 408 at a third angle.

In some embodiments, holographic medium 404 has a limited angular and/or spectral selectivity. For example, holographic medium 404 reflects light 402-1 with a specific wavelength range and/or with a specific distribution of incident angles while transmitting light with wavelengths outside the specific wavelength range and/or with incident angles outside the specific distribution of incident angles. In some embodiments, holographic medium 404 reflects light in the IR (e.g., NIR) wavelength range.

In some embodiments, holographic medium 404 is a volume hologram (also called a Bragg hologram). A volume hologram refers to a hologram with thickness sufficiently large for inducing Bragg diffraction, i.e., the thickness of the recording material used for recording a volume hologram is significantly larger than the wavelength of light used for recording the hologram. Such holograms have spectral selectivity, angular selectivity of an incident light and/or selectivity with respect to wavefront profile of an incident light.

Figure 4B:
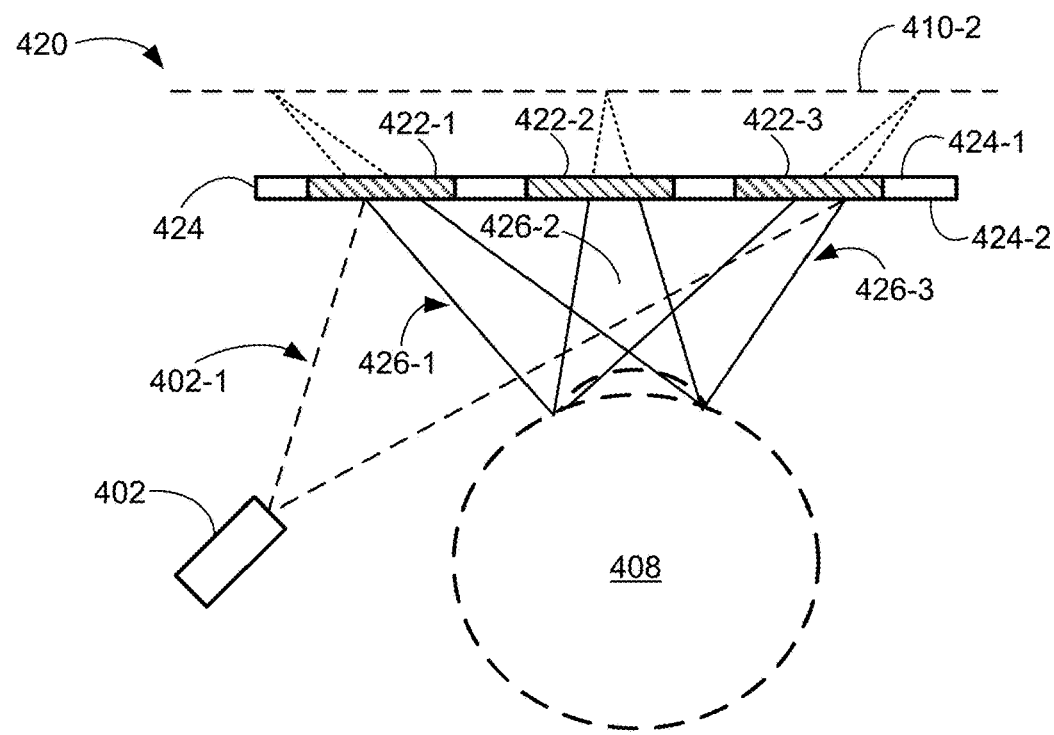
FIG. 4B is a schematic diagram illustrating a holographic illuminator in accordance with some embodiments.

FIG. 4B is a schematic diagram illustrating holographic illuminator 420 in accordance with some embodiments. Holographic illuminator 420 is similar to holographic illuminator 400 described above with respect to FIG. 4A, except that holographic illuminator 420 includes holographic medium 424 instead of holographic medium 420. Holographic medium 424 includes areas 422-1, 422-2, and 422-3 that are configured to interact with light 402-1 and concurrently direct (e.g., reflect, diffract, etc.) separate light patterns 426-1, 426-2, and 426-3 toward eye 408. Light patterns 426-1, 426-2, and 426-3 are distinct from the corresponding light patterns of FIG. 4A such that light patterns 426-1, 426-3, and 426-3 do not converge on a plane adjacent to eye 408. Instead, light patterns 426-1, 426-3, and 426-3 in FIG. 4B have projected convergence points on reference plane 410-2 positioned on an opposite side of holographic medium 424 from eye 408 (e.g., facing surface 424-1 of holographic medium 424 so that reference plane 410-2 is closer to surface 424-1 of holographic medium 424 than surface 424-2 of holographic medium 424).

Figure 4C:
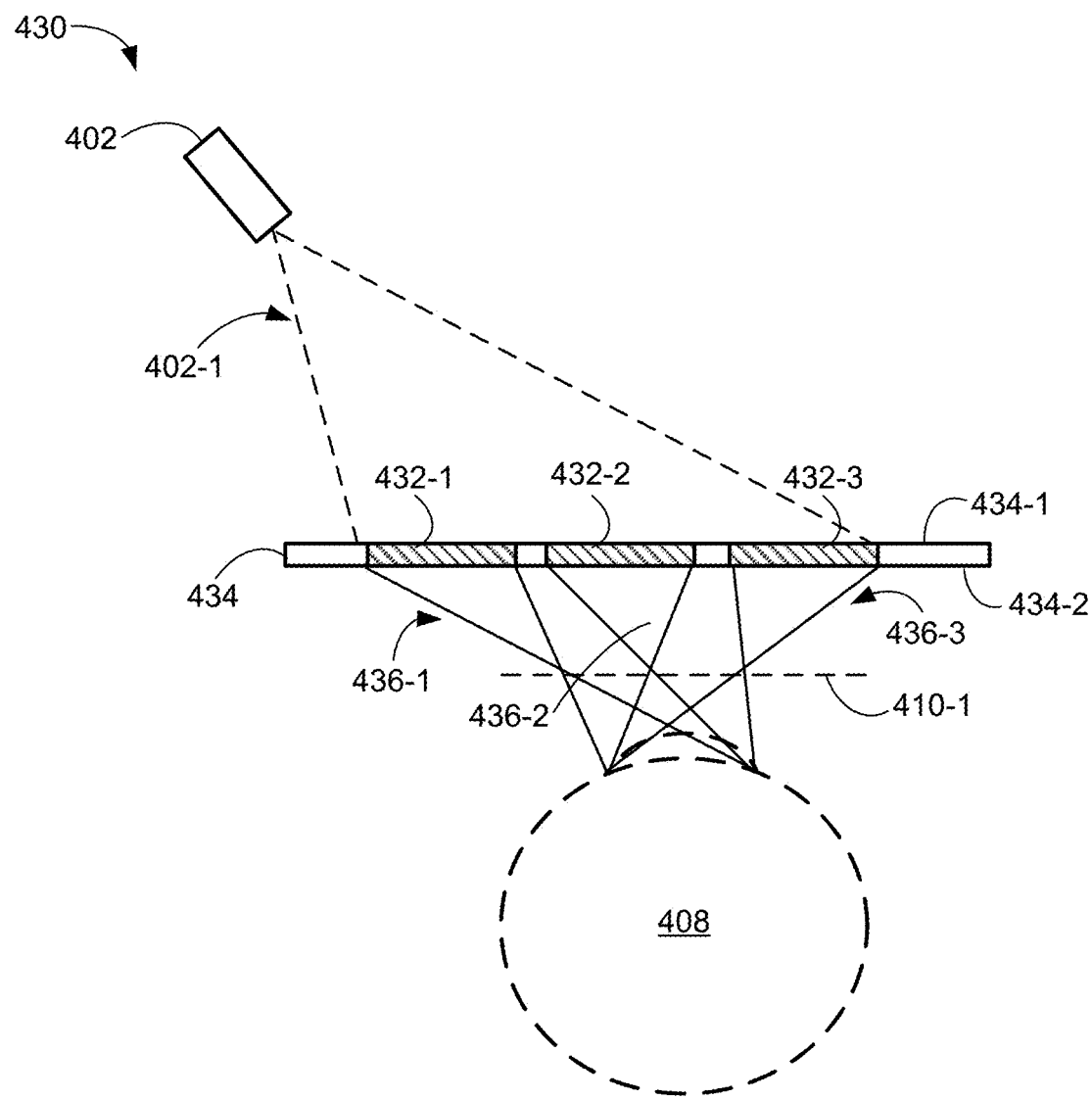
FIG. 4C is a schematic diagram illustrating a holographic illuminator in accordance with some embodiments.

FIG. 4C is a schematic diagram illustrating holographic illuminator 430 in accordance with some embodiments. Holographic illuminator 430 is similar to holographic illuminator 400 described above with respect to FIG. 4A, except that holographic illuminator 430 includes holographic medium 434, which is a transmission holographic medium having surfaces 434-1 and 434-2. Light source 402 is positioned away from an optical axis of holographic medium 434 and away from a field of view of eye 408. In holographic illuminator 430, light source 402 is positioned on opposite side of holographic medium 434 from eye 408, facing surface 434-1 of holographic medium 434 (e.g., light source 402 is positioned closer to surface 434-1 of holographic medium 434 than surface 434-2 of holographic medium 434). Holographic medium 434 includes areas 432-1, 432-2, and 432-3 that are configured to interact with light 402-1 and concurrently direct separate light patterns 436-1, 436-2, and 436-3 toward eye 408. Similar to the corresponding light patterns 406-1, 406-2, and 406-3 in FIG. 4A, light patterns 436-1, 436-2, and 436-3, in some embodiments, converge on reference plane 410-1 in proximity to eye 408 as shown in FIG. 4C, creating three virtual single-point light sources near eye 408. In some embodiments, light patterns 436-1, 436-2, and 436-3 have projected convergence points on a reference plane (e.g., reference plane 410-2 in FIG. 4B) positioned on opposite side of holographic medium 434 (e.g., facing surface 4341 of holographic medium 434).

Figure 4D:
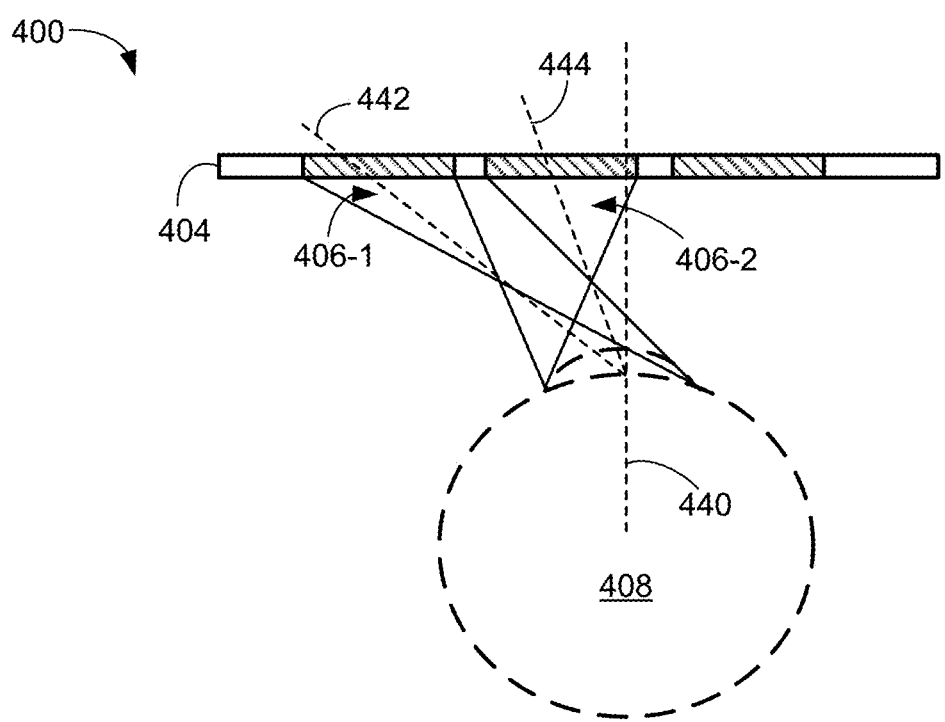

FIG. 4D is a schematic diagram illustrating holographic illuminator 400 shown in FIG. 4A. As explained above with respect to FIG. 4A, light patterns projected by holographic medium 404 (e.g., light patterns 406-1 and 406-2) are projected toward eye 408 at respective angles. FIG. 4A illustrates holographic illuminator 400 with reference line 442 representing the direction of light pattern 406-1 projected toward eye 408 and reference line 444 representing the direction of light pattern 406-2 projected toward eye 408. In FIG. 4D, reference line 440 corresponds to an optical axis of eye 408. As illustrated with respective reference lines 442 and 444, the direction of light pattern 406-1 is distinct from the direction of light pattern 406-2. In FIG. 4D, light pattern 406-1, which is the outermost light pattern projected by holographic medium 404, is projected toward eye 408 at a 53-degree angle with respect to reference line 440 and light pattern 406-2 is projected toward eye 408 at a 20-degree angle with respect to reference line 440. In some embodiments, light pattern 406-1 is projected toward eye 408 at an angle ranging from 30 to 40 degrees. In some embodiments, light pattern 406-1 is projected toward eye 408 in an angle ranging from 40 to 50 degrees. In some embodiments, light pattern 406-1 is projected toward eye 408 in an angle ranging from 50 to 55 degrees. In some embodiments, light pattern 406-1 is projected toward eye 408 in an angle of 45 degrees or more.

Figure 4E:
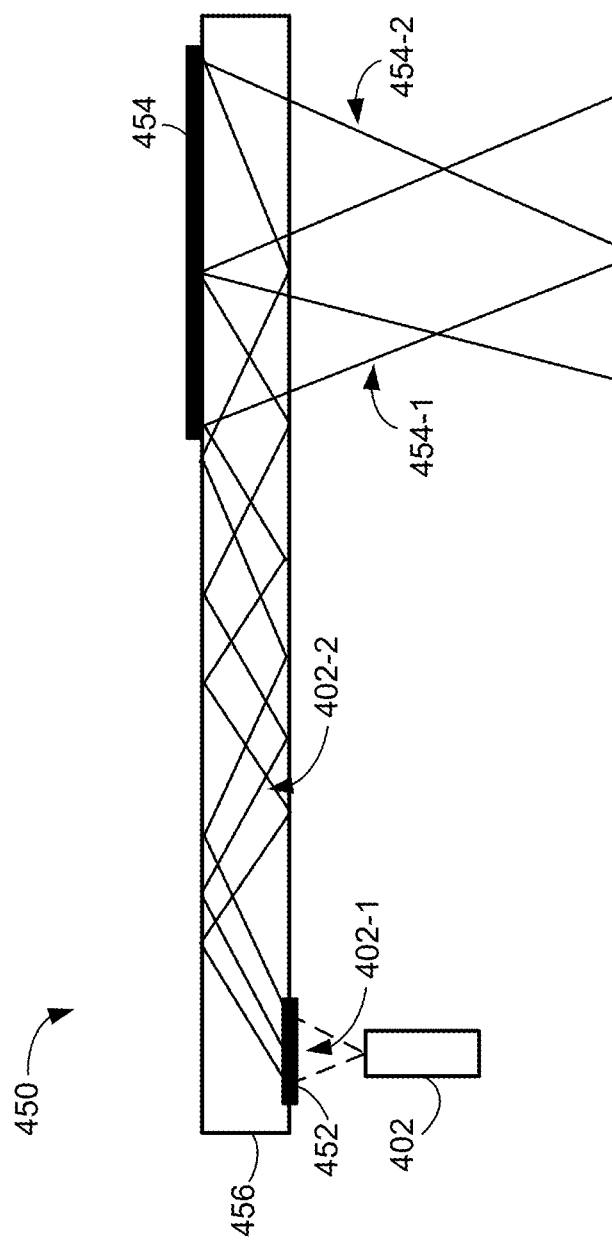
FIG. 4E is a schematic diagram illustrating a holographic illuminator in accordance with some embodiments.

FIG. 4E is a schematic diagram illustrating holographic illuminator 450 in accordance with some embodiments. Holographic illuminator 450 includes holographic medium 454 coupled with waveguide 456. In some embodiments, holographic medium 454 corresponds to holographic medium 404 described above with respect to FIG. 4A. Waveguide 456 is optically coupled with light source 402 and configured to receive light 402-1 projected by light source 402. In some embodiments, waveguide includes, or is coupled with, in-coupling element 452. In some embodiments, in-coupling element 452 is a prism or a diffractive or holographic structure (e.g., a surface relief grating or a volume hologram). In-coupling element 452 is configured to receive light 402-1 and transmit light 402-1 to waveguide 456 in such an angle that light 402-1 propagates through waveguide 456 by internal reflection, as illustrated with light 402-2. Holographic medium 454 acts as an out-coupling element such that when light 402-2 propagating through waveguide 456 interacts with holographic medium, the light is emitted as a plurality of light patterns (e.g., light patterns 454-1 and 454-2). In some embodiments, light patterns 454-1 and 454-2 correspond to light patterns 406-1, 406-2, and 406-3 reflected toward eye 408 described above with respect to FIG. 4A. In some embodiments, holographic illuminator 450 with waveguide 456 is configured to reduce the distance between light source 402 and holographic medium 454 in a direction parallel to an optical axis of holographic medium 454, thereby making holographic illuminator 450 more compact.

FIGS. 5A-5F are schematic diagrams illustrating configurations of light patterns used for eye tracking in accordance with some embodiments. The example light patterns illustrated in FIGS. 5A-5F are used for in-field illumination of an eye. In some embodiments, the eye is illuminated with an IR or NIR light for eye-tracking purposes (e.g., the light patterns illustrated in FIG. 5A-5F are illuminated with an IR or NIR light). In some embodiments, the light patterns shown in FIG. 5A-5F are configured to illuminate an area with a characteristic dimension (e.g., a diameter or width) of at least 10 mm on a surface of the eye. The configurations shown in FIGS. 5A-5F include a plurality of distinct and separate light patterns (e.g., image objects or image structures, such as light patterns 502-1, 502-2, and 502-3 in FIG. 5A), arranged in a uniform or a non-uniform configuration. In some embodiments, a number of patterns in the plurality of separate light patterns is between 5 and 2000. In some embodiments, the number of light patterns in a particular configuration is between seven and twenty. In some embodiments, the number of light patterns is between 20 and 1000. In some embodiments, the number of light patterns is between 1000 and 2000. In some embodiments, the light patterns have one or more predefined shapes, such as circles (e.g., spots), stripes, triangles, squares, polygons, crosses, sinusoidal objects and/or any other uniform or non-uniform shapes.

Figure 5A:
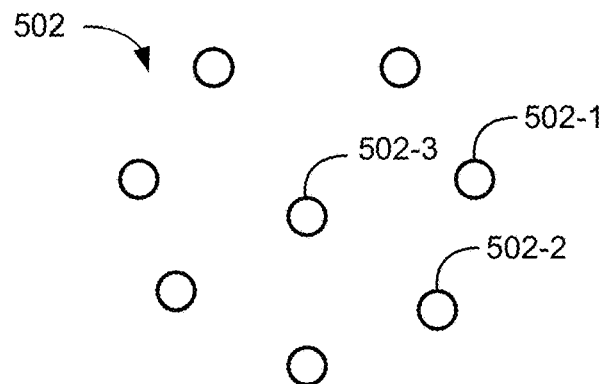
FIGS. 5A-5F are schematic diagrams illustrating configurations of light patterns used for eye tracking in accordance with some embodiments.

FIG. 5A illustrates configuration 502 including seven separate light patterns (e.g., light patterns 502-1, 502-2, and 502-3). In FIG. 5A, each light pattern has a shape of a circle (e.g., a solid circle or a hollow circle). Multiple light patterns (e.g., light patterns 502-1 and 502-2 among others) are arranged in a circular configuration with light pattern 502-3 positioned at the center of the circular configuration. In some embodiments, configuration 502 includes light patterns arranged in a plurality of concentric circles (e.g., 2, 3, 4, 5 circles or more). In some embodiments, configuration 502 does not include a central light pattern (e.g., light pattern 502-3).

Figure 5B:

FIG. 5B illustrates rectangular configuration 504 including a plurality (e.g., eight) of separate stripe-shaped light patterns (e.g., light patterns 504-1 and 504-2).

Figure 5C:
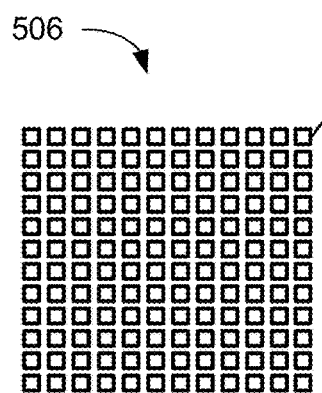

FIG. 5C illustrates configuration 506 including a plurality of light patterns arranged in a two-dimensional configuration (e.g., a rectangular configuration). In FIG. 5C, the plurality of light patterns is arranged in multiple rows and multiple columns (e.g., 144 light patterns arranged in twelve rows and twelve columns). In some embodiments, the plurality of light patterns is arranged to have a uniform spacing in a first direction and a uniform spacing in a second direction that is distinct from the first direction (e.g., the second direction is orthogonal to the first direction). In some embodiments, the plurality of light patterns is arranged to have a first spacing in the first direction and a second spacing in the second direction that is distinct from the first spacing. In some embodiments, the plurality of light patterns is arranged to have a uniform spacing in the first direction and a non-uniform spacing in the second direction. In some embodiments, the plurality of light patterns is arranged to have a uniform center-to-center distance in the first direction and a uniform center-to-center distance in the second direction. In some embodiments, the plurality of light patterns is arranged to have a first center-to-center distance in the first direction and a second center-to-center distance in the second direction that is distinct from the first center-to-center distance. In some embodiments, the plurality of light patterns is arranged to have a uniform center-to-center distance in the first direction and a non-uniform center-to-center distance in the second direction.

In FIG. 5C, each light pattern has a same shape (e.g., a square, rectangle, triangle, circle, ellipse, oval, star, polygon, etc.).

Figure 5D:
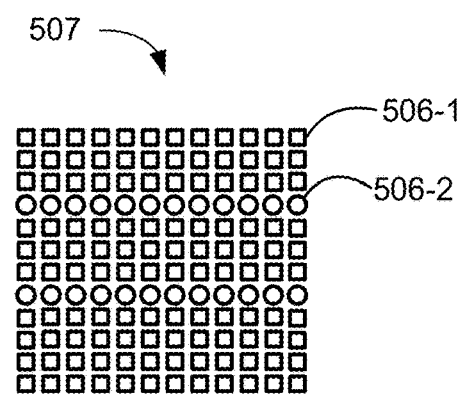

FIG. 5D is similar to FIG. 5C, except that, in FIG. 5D, configuration 507 of the plurality of light patterns includes a first set of light patterns 506-1 each having a first shape (e.g., a square or a rectangle) and a second set of light patterns 506-2 each having a second shape (e.g., a circle) that is distinct from the first shape.

Figure 5E:
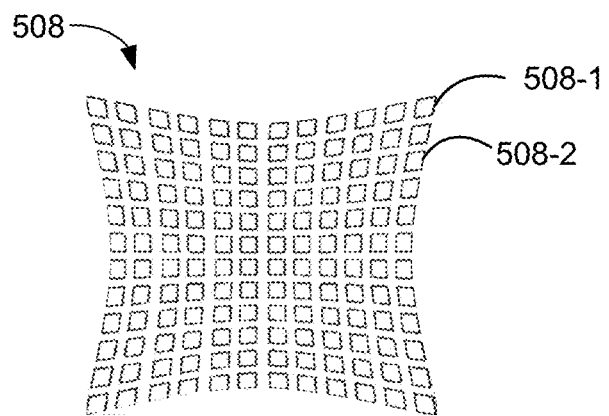

FIG. 5E illustrates configuration 508 (e.g., a pincushion shape as shown in FIG. 5E, a barrel shape, etc.) including distorted square-shaped light patterns (e.g., light patterns 508-1 and 508-2, among others). Configuration 508 shown in FIG. 5E is configured to account for the contoured surface profile of an eye so that when configuration 508 of light patterns, or at least a portion of configuration 508 of light patterns, is reflected off from the surface of the eye, the captured reflections (e.g., reflected glints) are arranged in a non-distorted configuration (e.g., in a rectangular arrangement). For example, configuration 508 of light patterns arranged in the pincushion shape shown in FIG. 5E is configured so that the reflection of configuration 508 of light patterns projects at least a subset of the light patterns arranged in a rectangular configuration (e.g., an image of the light patterns reflected by the surface of the eye shows the light patterns arranged in a rectangular arrangement as shown in FIG. 5C).

Figure 5F:
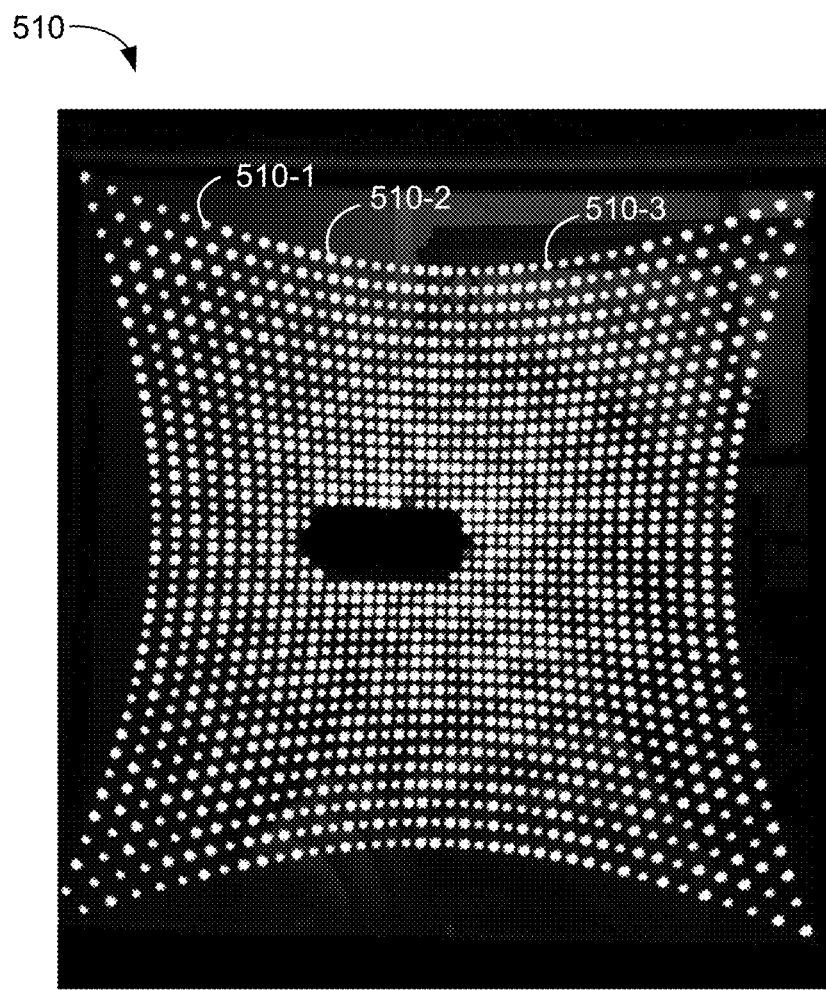

FIG. 5F illustrates an image of light patterns arranged in pincushion configuration 510. The light patterns shown in FIG. 5F (e.g., light patterns 510-1, 510-2, and 510-3) have a shape of a circle.

In some embodiments, light patterns of a respective configuration have same characteristics, such as shape, size, intensity, and/or wavelength. In some embodiments, light patterns of a respective configuration have different characteristics. For example, in FIG. 5F, light pattern 510-1 has a smaller size than light pattern 510-2. In some embodiments, light pattern 510-1 is illuminated with lower intensity that light pattern 510-2. In some embodiments, light pattern 510-1 is illuminated with different wavelength than light pattern 510-2.

Figure 6A:
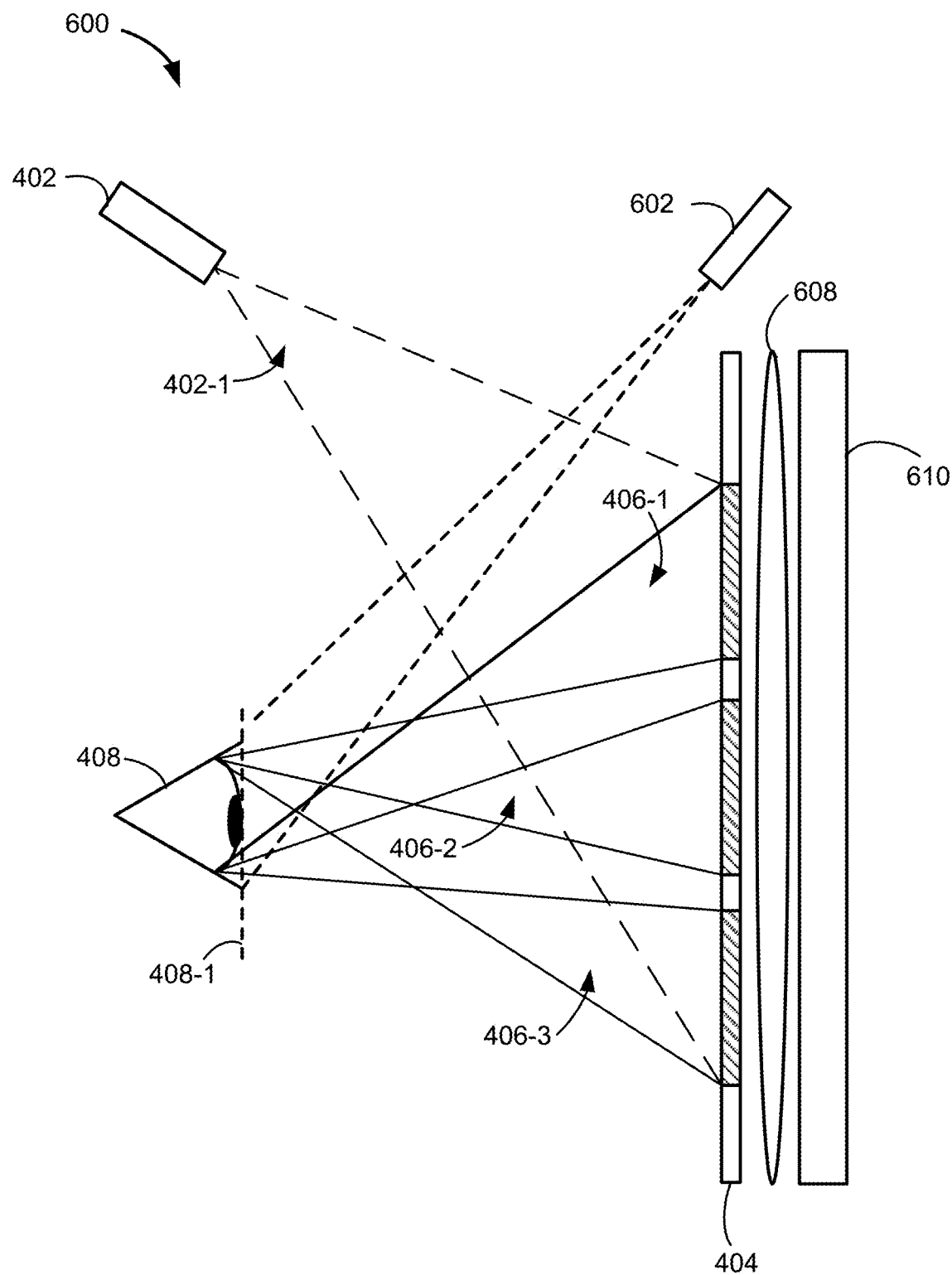
FIG. 6A is a schematic diagram illustrating a display device in accordance with some embodiments.

FIG. 6A is a schematic diagram illustrating display device 600 in accordance with some embodiments. In some embodiments, display device 600 is configured to provide virtual reality content to a user. In some embodiments, display device 600 corresponds to display device 100 described above with respect to FIG. 1. In FIG. 6A, display device 600 includes light source 402, holographic medium 404, detector 602, display 610 and one or more lenses 608. Holographic medium 404 optically coupled with light source 402 operates as a holographic illuminator described above with respect to FIG. 4A. Light source 402 provides light 402-1 received by holographic medium 404, which then projects the light as light patterns 406-1, 406-2, and 406-3 toward eye 408. Detector 602 captures an image (e.g., an image of an area defined by rays 608-1) of at least a portion of light patterns 406-1, 406-2, and 406-3 reflected off a surface (e.g., a sclera) of eye 408 directed by holographic medium 404 toward detector 602 for determining a position of a pupil of eye 408.

Holographic medium 404, light source 402 and detector 602 of an eye-tracking system are configured to determine a position of the pupil of eye 408 and/or track its movement as eye 408 rotates toward different gaze directions. In some embodiments, the eye tracking system corresponds to, is coupled with, or is included in eye tracking module 217 described herein with respect to FIG. 2. In some embodiments, detector 602 is an IR and/or NIR camera (e.g., a still camera or a video camera) or other IR and/or NIR sensitive photodetector (e.g., an array of photodiodes). In some embodiments, determining a position of the pupil includes determining the position of the pupil on an x-y plane of the pupil (e.g., reference plane 408-1). In some embodiments, the x-y plane is a curvilinear plane. In some embodiments, detector 602 is integrated with light source 402. In some embodiments, light projected by light source 402 (e.g., light 402-1) and an image captured by detector 602 (e.g., an image of an area defined by rays 608-1) have the same optical path (or parallel optical paths) and are transmitted or guided by the same optical elements (e.g., holographic medium 404).

In some embodiments, the position of the pupil of eye 408 is determined based on a representative intensity or intensities of detected glints. In some embodiments, the position of the pupil is determined based on an incident angle of detected glints (e.g., display device 600 includes one or more optical elements to determine the incident angle of the detected glint). For example, the position of the pupil is determined by comparing an incident angle of reflected light patterns 406-1, 406-2, and 406-3 to an estimated surface profile of the surface of eye 408. The surface profile of an eye does not correspond to a perfect sphere but instead has a distinct curvature in the area that includes the cornea and the pupil. Therefore, a position of the pupil can be determined by determining the surface profile of the eye.

In some embodiments, at least a portion of light patterns 406-1, 406-2, and 406-3 impinges on other surfaces of eye 408 than sclera (e.g., the pupil). In some embodiments, the position of the pupil is determined based on a portion of light patterns 406-1, 406-2, and 406-3 impinging on the sclera and impinging on the other surfaces of eye 408. In some embodiments, the position of the pupil of eye 408 is determined based on a difference (and/or a ratio) between an intensity of a portion of light patterns 406-1, 406-2, and 406-3 impinging on the sclera and on the pupil. For example, the intensity of the portion of light patterns reflected on the sclera of eye is higher than the intensity the portion of light patterns reflected on the pupil and therefore the location of the pupil can be determined based on the intensity difference.

In some embodiments, the position of the pupil of eye 408 is determined based on a difference in a configuration (e.g., configurations described above with respect to FIG. 5A-5F) projected by the holographic illuminator and a configuration captured by detector 602. For example, as a light with a specific configuration is reflected off the non-flat surface of eye 408, the structured pattern is modified (e.g., distorted). The non-flat surface profile of eye 408 is then determined based on the distorted structured pattern and the position of the pupil is determined based on the surface profile.

In FIG. 6A, light source 402 and detector 602 are located away from an optical axis of holographic medium 404, as well as away from optical axes of one or more lenses 608 and display 610. For example, light source 402 and detector 602 are position on a temple and/or a frame of a head-mounted display device. Furthermore, light source 402 and detector 602 are positioned away from a field-of-view of eye 408 so that they do not occlude display 610. In FIG. 6A, holographic medium 404 is positioned adjacent to one or more lenses 608. Holographic medium 404 is configured to provide light patterns 406-1, 406-2, and 406-3 in the field-of-view of eye 408. In FIG. 6A, holographic medium 404 is a reflection holographic medium, and light source 402 is located to illuminate a surface of holographic medium 404 that is configured to face eye 408.

In some embodiments, holographic medium 404 is wavelength selective, thereby reflecting light 402-1 with specific wavelength range while transmitting light with other wavelengths, such as light from display 610. In some embodiments, light 402-1 used for eye-tracking is IR or NIR light, and therefore does not interfere with visible light projected from display 610.

Figure 6B:
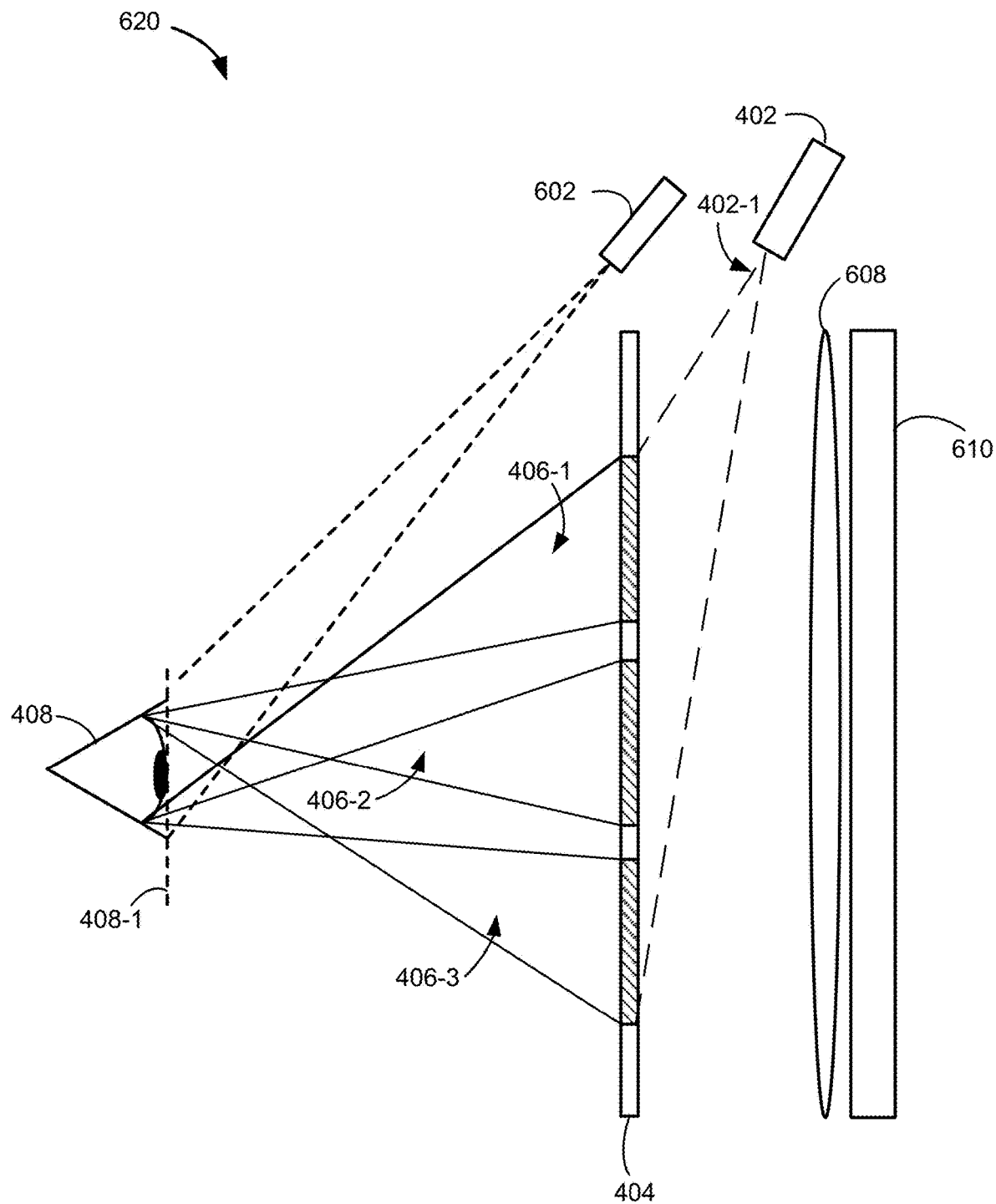
FIG. 6B is a schematic diagram illustrating a display device in accordance with some embodiments.

FIG. 6B is a schematic diagram illustrating display device 620 in accordance with some embodiments. Display device 620 is similar to display device 600 described above with respect to FIG. 6A, except that holographic medium 404 is a transmission holographic medium and light source 402 is located to illuminate a surface of holographic medium 404 that is configured to face away from eye 408 (e.g., configured to face display 610).

Figure 6C:
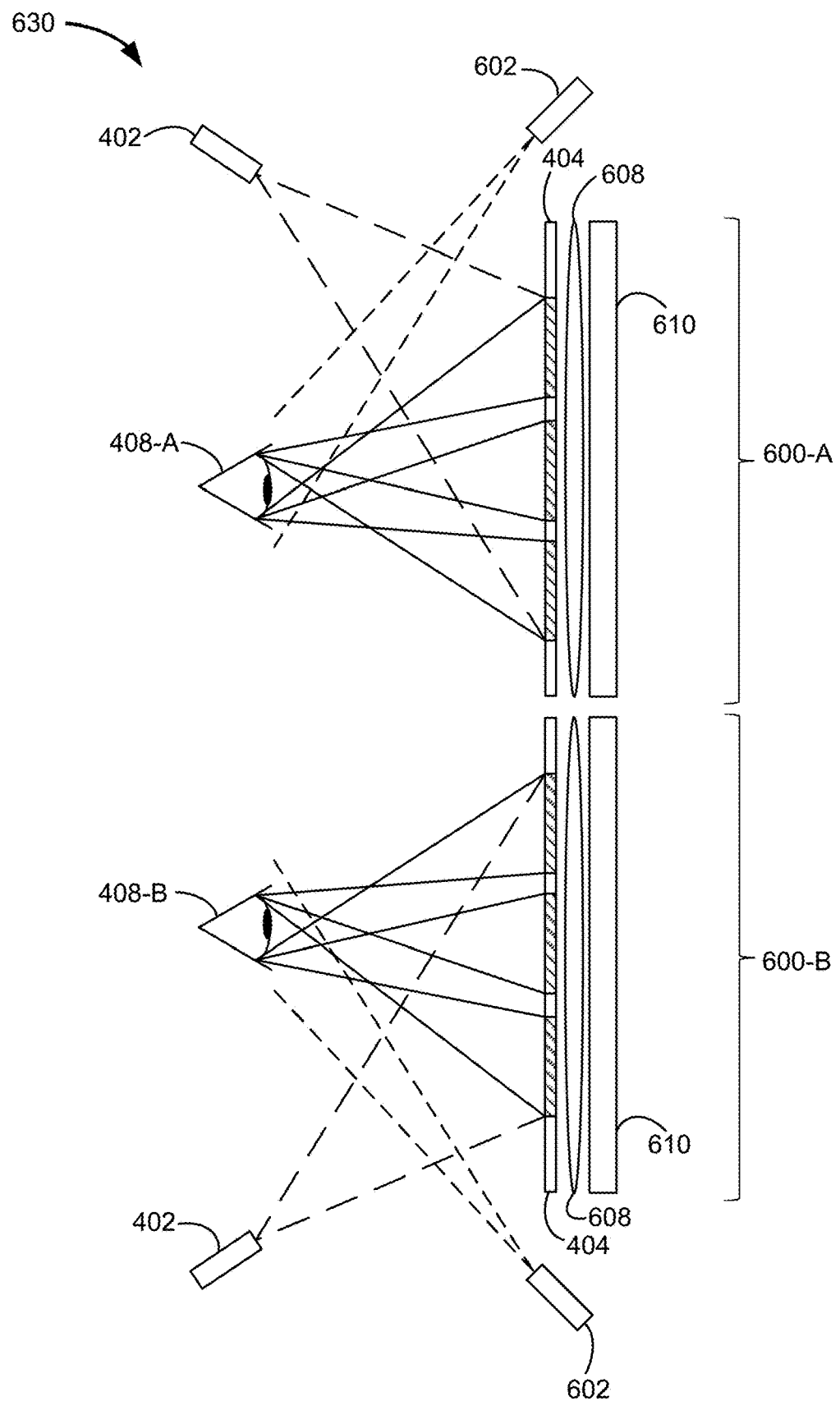
FIG. 6C is a schematic diagram illustrating a display device in accordance with some embodiments.

FIG. 6C is a schematic diagram illustrating display device 630 in accordance with some embodiments. Display device 630 includes display device 600-A for eye 408-A (e.g., the left eye of a user of a head-mounted display device 630) and display device 600-B for eye 408-B (e.g., the right eye of a user of a head-mounted display device 630). In some embodiments, each of display devices 600-A and 600-B corresponds to display device 600 described above with respect to FIG. 6A. In some embodiments, a head-mounted display includes two display devices, each corresponding to display device 620 described above with respect to FIG. 6B. In some embodiments, display device 630 corresponds to display device 100 described above with respect to FIG. 1.

Figure 6D:
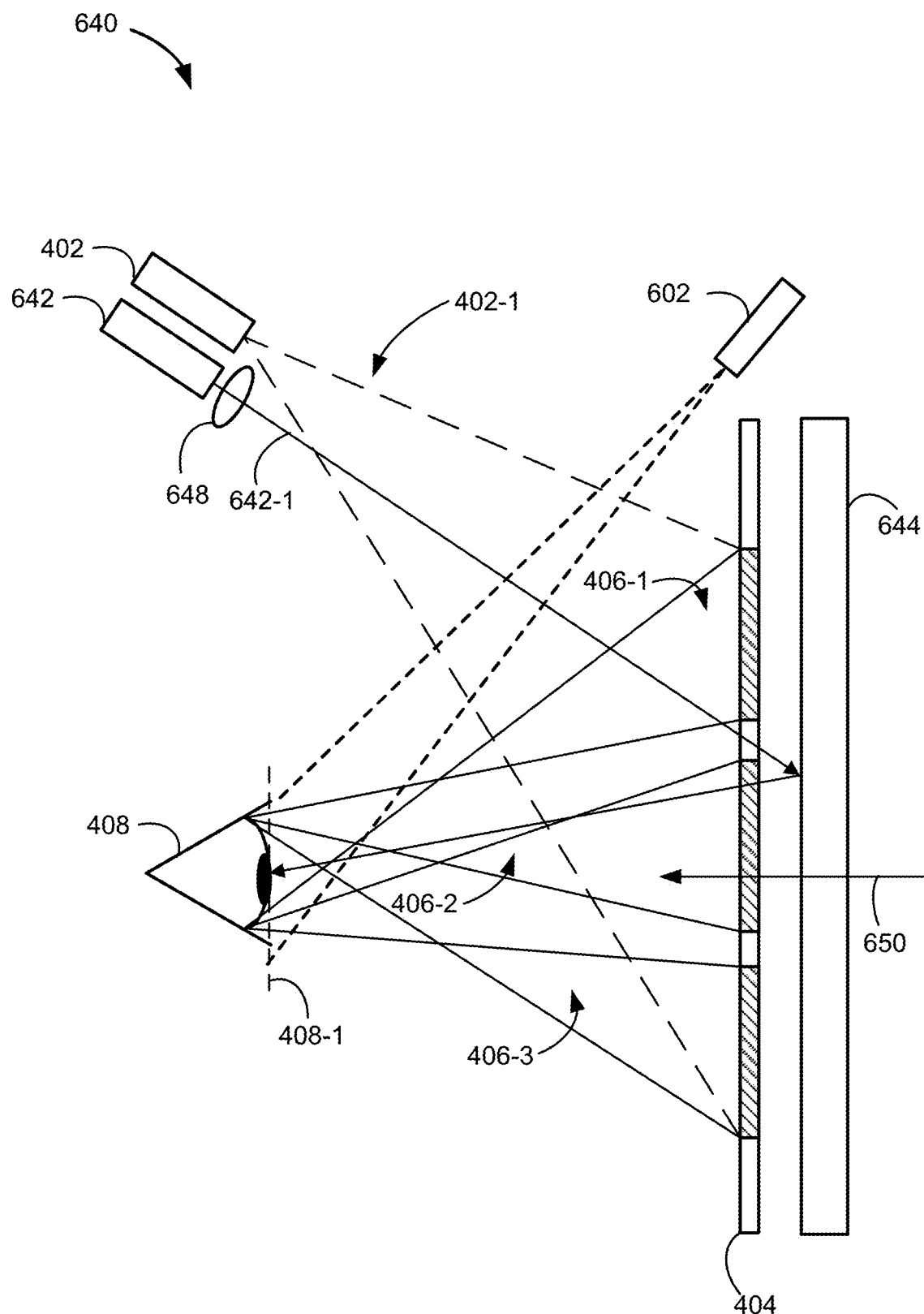
FIG. 6D is a schematic diagram illustrating a display device in accordance with some embodiments.

FIG. 6D is a schematic diagram illustrating display device 640 in accordance with some embodiments. Display device 640 is similar to display device 600 described above with respect to FIG. 6A, except that display device 640 is configured for providing augmented reality content to a user. Display device 640 includes display 642 (or a light projector) positioned in adjacent to light source 402 (e.g., positioned on a temple of a head-mounted display device). Display 642 projects light 642-1 toward beam combiner 644. Beam combiner 644 reflects and/or guides at least a portion of light 642-1 toward eye 408. Beam combiner 644 combines light 642-1 with light (e.g., light 650) coming from the outside of display device 640 (e.g., ambient light) so that an image represented by light 642-1 is overlapped with, or superimposed on, a real-world image provided by light 650. In some embodiments, beam combiner 644 is a polarization-dependent reflector that is configured to reflect light having a first polarization and transmits light having a second polarization that is distinct from the first polarization. In some embodiments, beam combiner 644 is an angle-dependent reflector that is configured to reflect light having a first incident angle and transmit light having a second incident angle that is distinct from the first incident angle (e.g., the second incident angle is less than the first incident angle).

Figure 7A:
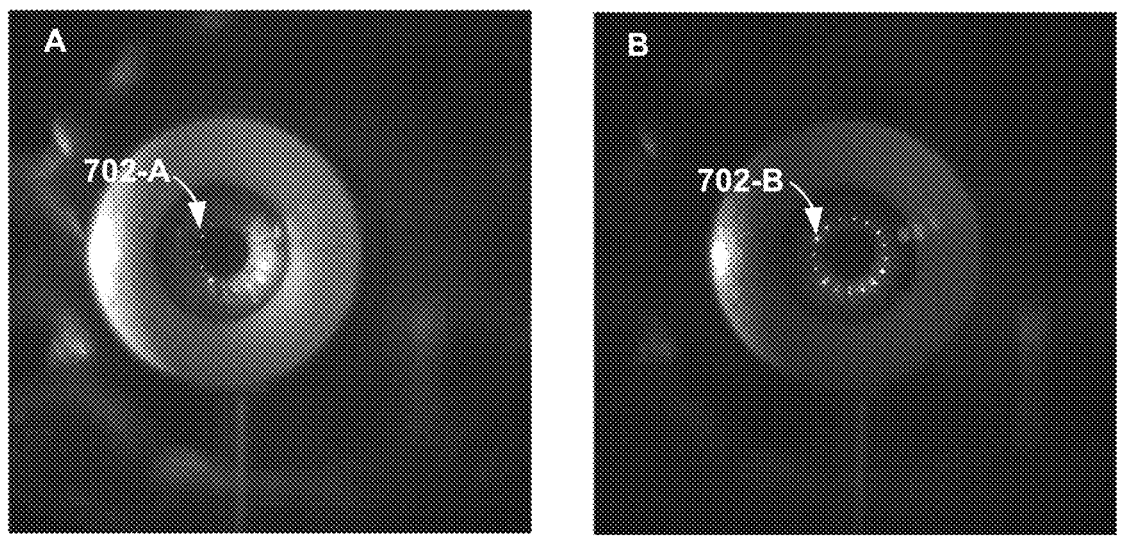
FIG. 7A is an image illustrating a plurality of light patterns reflected off one or more surfaces of an eye in accordance with some embodiments.

FIG. 7A is an image illustrating a plurality of light patterns projected on (and reflected off) one or more surfaces of an eye in accordance with some embodiments. Sections A and B of FIG. 7A are images of a model eye captured by a detector of an eye-tracking system (e.g., detector 602 of display device 600 described above with respect to FIG. 6A) when a reference eye is in different positions. Section A of FIG. 7A illustrates a plurality of glints, including glint 702-A, arranged in a circle when a reference eye is at a first position and Section B of FIG. 7A illustrates a plurality of glints, including glint 702-B, when the reference eye is at a second position. A position of a pupil of the reference eye can be determined based on the captured images. In some embodiments, the position of a pupil of the reference eye is determined based on intensities of respective glints. For example, glint 702-A in Section A has a lower intensity than the corresponding glint 702-B in Section B. This indicates that the pupil of the eye is tilted toward glint 702-B (e.g., glint 702-B is projected on the pupil so that glint 702-B is not reflected or reflected at a lower intensity than glints reflected off an iris of the eye). In some embodiments, the position of the pupil of the reference eye is determined based on locations of respective glints, such as locations of glints 702-A and 702-B.

Figure 7B:
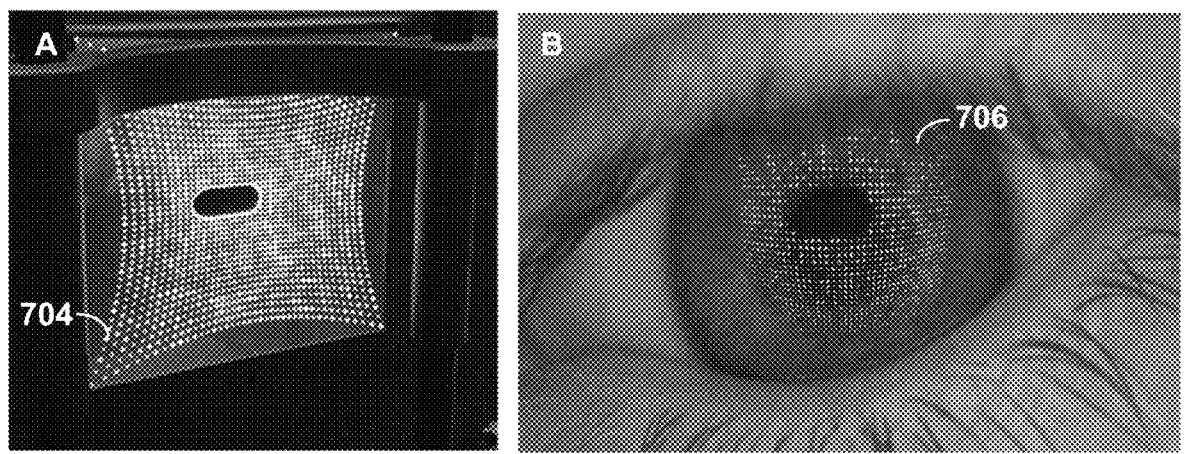
FIG. 7B is an image illustrating a plurality of light patterns and a reflection of the plurality of light patterns from one or more surfaces of an eye in accordance with some embodiments.

FIG. 7B is an image illustrating a plurality of light patterns projected by a light source (Section A of FIG. 7B) and a plurality of light patterns imaged from one or more surfaces of an eye (Section B of FIG. 7B) in accordance with some embodiments. Section A is an example image of a plurality of separate image patterns (e.g., plurality of light patterns 704) projected by a holographic illuminator. The patterns in Section A are arranged in a pincushion configuration (e.g., corresponding to the configuration described with respect to FIG. 5E). The pincushion configuration is configured to counter for a surface profile of an eye so that the light patterns reflected off the surface of the eye are configured in a non-distorted configuration (e.g., a rectangle). Section B of FIG. 7B is an exemplary image captured by a detector of an eye-tracking system, (e.g., detector 602 of display device 600 described above with respect to FIG. 6A). The image in Section B of FIG. 7B illustrates plurality of glints 706 reflected off one or more surfaces of the reference eye, arranged in a rectangular configuration. In some embodiments, the position of the pupil of the reference eye is determined based on the detected glints (e.g., the intensity and/or the presence-absence of respective glints). In FIG. 7B, the pincushion shape in Section A is modified by the surface profile of the reference eye to have the rectangular shape as shown in Section B. The position of the pupil is determined based on the surface profile of the reference eye (which is determined based on the arrangement of detected glints).

Figure 8A:
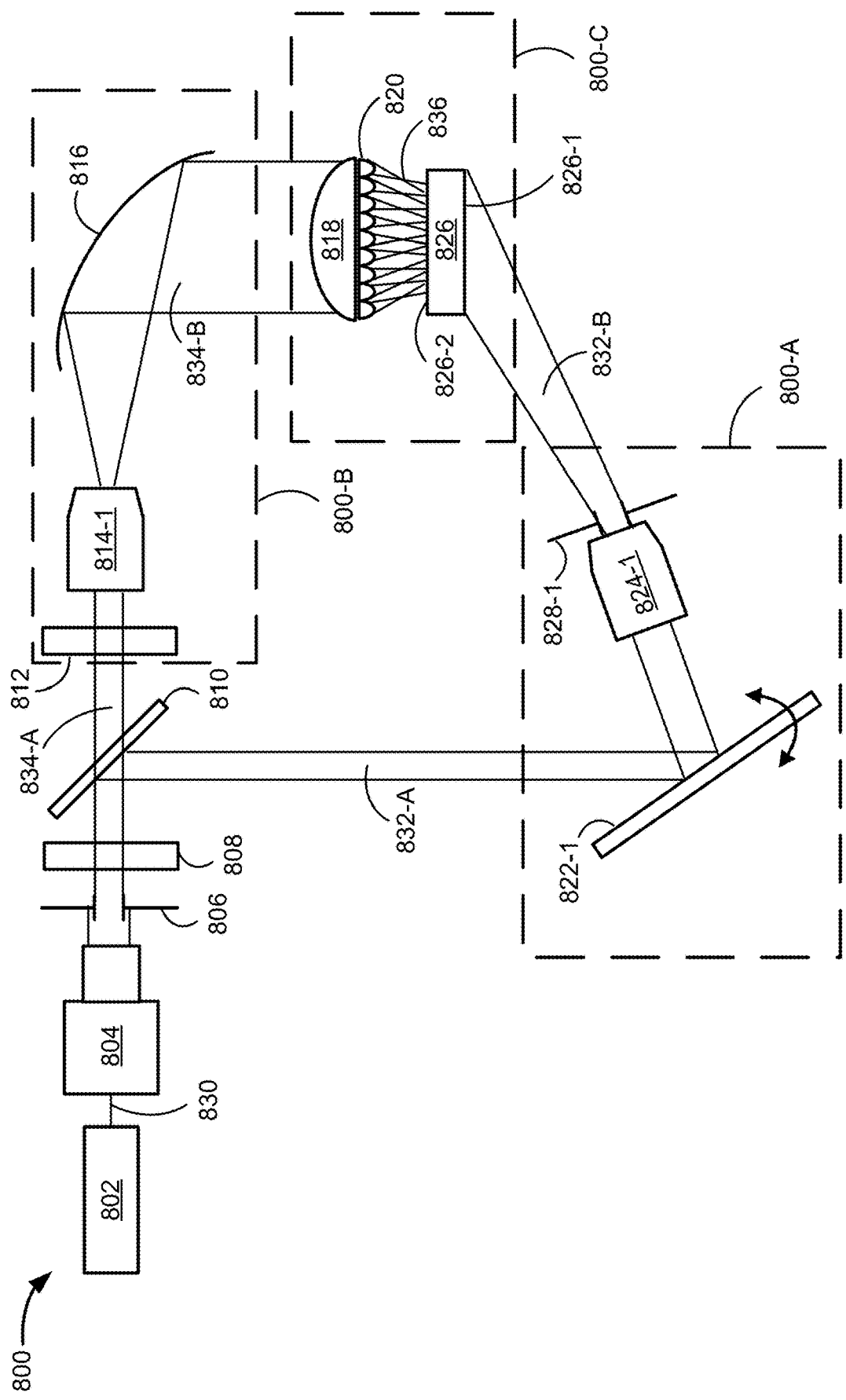
FIG. 8A is a schematic diagram illustrating a system for preparing a wide-field holographic medium in accordance with some embodiments.

FIG. 8A is a schematic diagram illustrating system 800 for generating a wide-field holographic medium in accordance with some embodiments. System 800 includes light source 802. In some embodiments, light source 802 is a point-light source (e.g., a laser). In some embodiments, beam 830 provided by light source 802 is coherent light. Light source 802 is optionally coupled optically with a plurality of optical components for modifying beam 830, such as beam expander 804 that expands beam 830 and aperture 806 for adjusting the beam size of beam 830. In some embodiments, beam 830 provided by light source 802 has a beam size with diameter less than 1 mm, which is then expanded to a beam size with a diameter greater than 10 mm, which is, in turn, clipped to a beam size with a diameter between 7 mm and 9 mm by aperture 806.

In some embodiments, system 800 includes polarizer 808 and a polarization of beam 830 is adjusted by polarizer 808. For example, in some implementations, polarizer 808 is a half-wave plate configured to adjust a direction of a linear polarized light.

In FIG. 8A, beam 830 is divided into two physically separated beams 832-A and 834-A by beam splitter 810. In some embodiments, beam splitter 810 is a 50/50 reflector (e.g., beam 832-A and beam 834-A have the same intensity).

In some embodiments, beam splitter 810 is a polarizing beam splitter dividing beam 830 into beam 832-A with a first polarization (e.g., polarization in the vertical direction) and beam 834-A with a second polarization (e.g., polarization in the horizontal direction). In some embodiments, a combination of a half-wave plate (e.g., polarizer 808) and a polarizing beam splitter (e.g., beam splitter 810) is used for adjusting intensities of beams 832-A and 834-A and/or adjusting a ratio of intensities of beams 832-A and 834-A. For example, in some implementations, the intensities are adjusted by changing the orientation of the half-wave plate. In some embodiments, the polarization of one or more of the beams 832-A and 834-A is further adjusted by one or more polarizers (e.g., polarizer 812, which can be a half-way plate). In FIG. 8A, polarizer 812 of a second set of optical elements 800-B adjusts the polarization of beam 834-A to correspond to the polarization of beam 832-A. In some implementations, polarizer 812 is included in a first set of optical elements 800-A for adjusting the polarization of beam 832-A.

Beam 832-A is directed, for example by beam splitter 810, toward the first set of optical elements 800-A. The first set of optical elements 800-A includes optical elements for providing a wide-field illumination serving as a reference light in a formation of a holographic medium. In some embodiments, the first set of optical elements 800-A includes reflector 822-1, which directs beam 832-A toward lens 824-1. In some embodiments, the first set of optical elements 800-A includes lens 824-1 for expanding beam 832-A and transmitting wide-field beam 832-B toward optically recordable medium 826. In some embodiments, the first set of optical elements 800-A includes a subset, or a superset of optical components illustrated in FIG. 8A. For example, the first set of optical elements 800-A may include other optical elements, that are not illustrated in FIG. 8A, for providing a wide-field illumination onto optically recordable medium 826. In some implementations, the first set of optical elements 800-A may not include one or more optical elements illustrated as components of the first set of optical elements 800-A in FIG. 8A. A wide-field beam has a spot size applicable for illuminating, with a single exposure, an area on optically recordable medium 826 for forming any of the holographic mediums described above with respect to FIGS. 4A-4D. In some embodiments, a wide-field beam refers to a beam with a spot size with a characteristic dimension (e.g., a diameter or width) of at least 10 mm. In some embodiments, a wide-field beam refers to a beam with a spot size with a characteristic dimension (e.g., a diameter or width) of at least 100 mm. In some embodiments, lens 824-1 is a microscopic objective (e.g., lens 824-1 is a microscopic objective with 20× magnification with numerical aperture of 0.4). In some embodiments, lens 824-1 is a lens assembly including two or more lenses. Optionally, lens 824-1 is optically coupled with aperture 828-1 for adjusting a size of beam 832-B. In some embodiments, aperture 828-1 has a diameter between 5 mm and 6 mm. In some embodiments, aperture 828-1 has a diameter between 6 mm and 7 mm. In some embodiments, aperture 828-1 has a diameter between 7 mm and 8 mm. In some embodiments, aperture 828-1 has a diameter between 8 mm and 9 mm. In some embodiments, aperture 828-1 has a diameter between 9 mm and 10 mm. In some embodiments, aperture 828-1 has a diameter between 10 mm and 11 mm. In some embodiments, reflector 822-1 is an adjustable reflector configured for adjusting the direction of beam 832-A, thereby adjusting the direction of wide-field beam 832-B transmitted from lens 824-1 toward optically recordable medium 826. In some implementations, wide-field beam 832-B provides a single-shot off-axis illumination with a diameter of at least 10 mm (e.g., 100 mm or more) onto surface 826-1 of optically recordable medium 826.

In some embodiments, optically recordable medium 826 includes photosensitive polymers, silver halide, dichromatic gelatin and/or other standard holographic materials. In some embodiments, optically recordable medium 826 includes other types of wavefront shaping materials (e.g., metamaterials, polarization sensitive materials, etc.). In some embodiments, optically recordable medium 826 has a thickness (e.g., distance between surfaces 826-1 and 826-2) that is much greater than the wavelength of lights 832-B and 834-B in order to record a volume hologram.

In some embodiments, optically recordable medium 826 is coupled with a waveguide (e.g., waveguide 456 in FIG. 4E) in order to record a holographic medium (e.g., holographic medium 454) that is configured to receive light propagating through a waveguide, as described above with respect to holographic illuminator 450 in FIG. 4E.

Beam 834-A is directed, by beam splitter 810, toward the second set of optical elements 800-B. The second set of optical elements 800-B includes optical elements for providing a wide-field illumination to a third set of optical elements 800-C.

In some embodiments, the second set of optical elements 800-B includes lens 814-1 and parabolic reflector 816. In some embodiments, the second set of optical elements 800-B includes a subset, or a superset of optical components illustrated in FIG. 8A. For example, the first set of optical elements 800-A may include other optical elements, that are not illustrated in FIG. 8A, for providing a wide-field illumination to the third set of optical elements 800-C. In some implementations, the second set of optical elements 800-B may not include one or more optical elements illustrated as components of the second set of optical elements 800-B in FIG. 8A.

In some embodiments, lens 814-1 is a microscopic objective (e.g., lens 814-1 is a microscopic objective with 20× magnification and a numerical aperture of 0.4) configured to expand beam 834-A. In some embodiments, lens 814-1 is a lens assembly including two or more lenses. In FIG. 8A, lens 814-1 transmits beam 834-A toward parabolic reflector 816. Parabolic reflector 816 collimates beam 834-A and reflects collimated wide-field beam 834-B toward the third set of optical elements 800-C. In some embodiments, parabolic reflector 816 is positioned in 45-degree angle with respect an optical axis of beam 834-A transmitted through lens 814-1. In some embodiments, the combination of lens 814-1 and parabolic reflector 816 expands beam 834-A such that beam 834-B has a beam diameter of 10 mm or more. For example, the combination of lens 814-1 and parabolic reflector 816 is configured to expand beam 834-A with a beam diameter of 8 mm into a wide-field beam 834-B with a beam diameter of 100 mm.

In FIG. 8A, parabolic reflector 816 of the second set of optical elements 800-B is located to intersect with an optical axis of the holographic medium formed from optically recordable medium 826 (e.g., an axis that is perpendicular to the holographic medium). In some implementations, parabolic reflector 816 reflects beam 834-B onto optically recordable medium 826 in a direction perpendicular to optically recordable medium 826, thereby providing an on-axis illumination onto surface 826-2 of optically recordable medium 826 while beam 832-B provides an off-axis illumination onto surface 826-1 of optically recordable medium 826.

The third set of optical elements 800-C receives wide-field beam 834-B and project the beam as a plurality of light patterns 836 toward optically recordable medium 826 for forming a holographic medium. System 800 is configured to form holographic mediums described above with respect to FIGS. 4A-4B. The holographic mediums formed by formed by system 800 are configured to project configurations such as any of those described above with respect to FIGS. 5A-5F. In some embodiments, the third set of optical elements 800-C includes condenser lens 818 and lenses 820. Condenser lens 818 is configured to transmit wide-field beam 834-B through lenses 820. In some embodiments, condenser lens 818 focuses wide-field beam 834-B toward a reference pupil (e.g., the position of the reference pupil corresponding to a position of a pupil of an eye of a user of a display device, such as eye 408 in FIG. 6A). Different embodiments of the third set of optical elements 800-C are described below with respect to FIGS. 9A-9L.

Figure 8B:
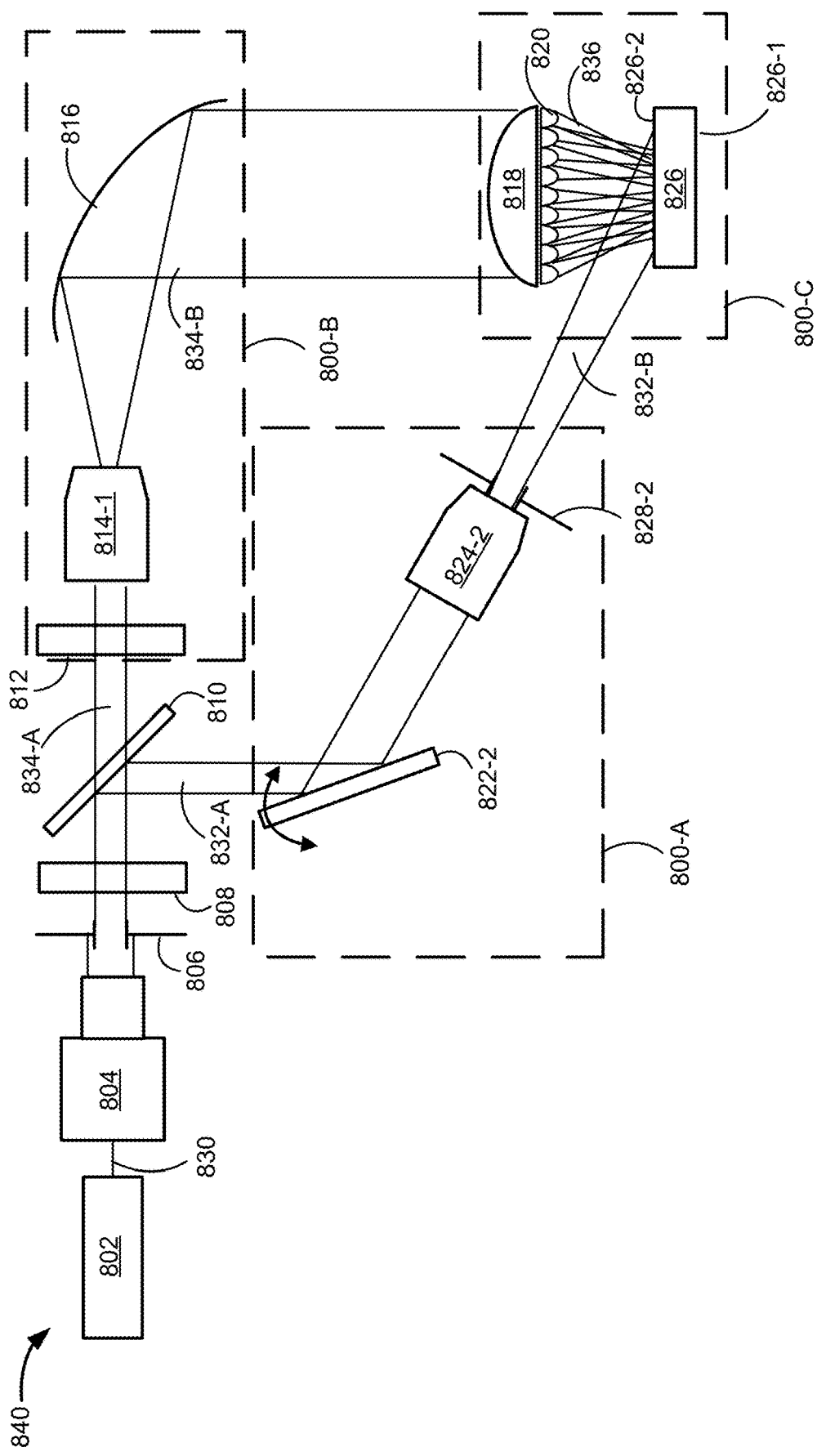
FIG. 8B is a schematic diagram illustrating a system for preparing a wide-field holographic medium in accordance with some embodiments.

FIG. 8B is a schematic diagram illustrating system 840 for generating a wide-field holographic medium in accordance with some embodiments. System 840 is similar to system 800 described above with respect to FIG. 8A, except that the first set of optical elements 800-A including reflective mirror 822-2, lens 824-2 and aperture 828-2 in FIG. 840 is configured to provide wide-field beam 832-B onto surface 826-2 of optically recordable medium 826 (e.g., both the first set of optical elements 800-A and the second set of optical elements 800-B provide wide-field beams 832-B and 834-B onto a same surface of optically recordable medium 826). System 840 is configured to form holographic mediums described above with respect to FIG. 4C.

Figure 8C:
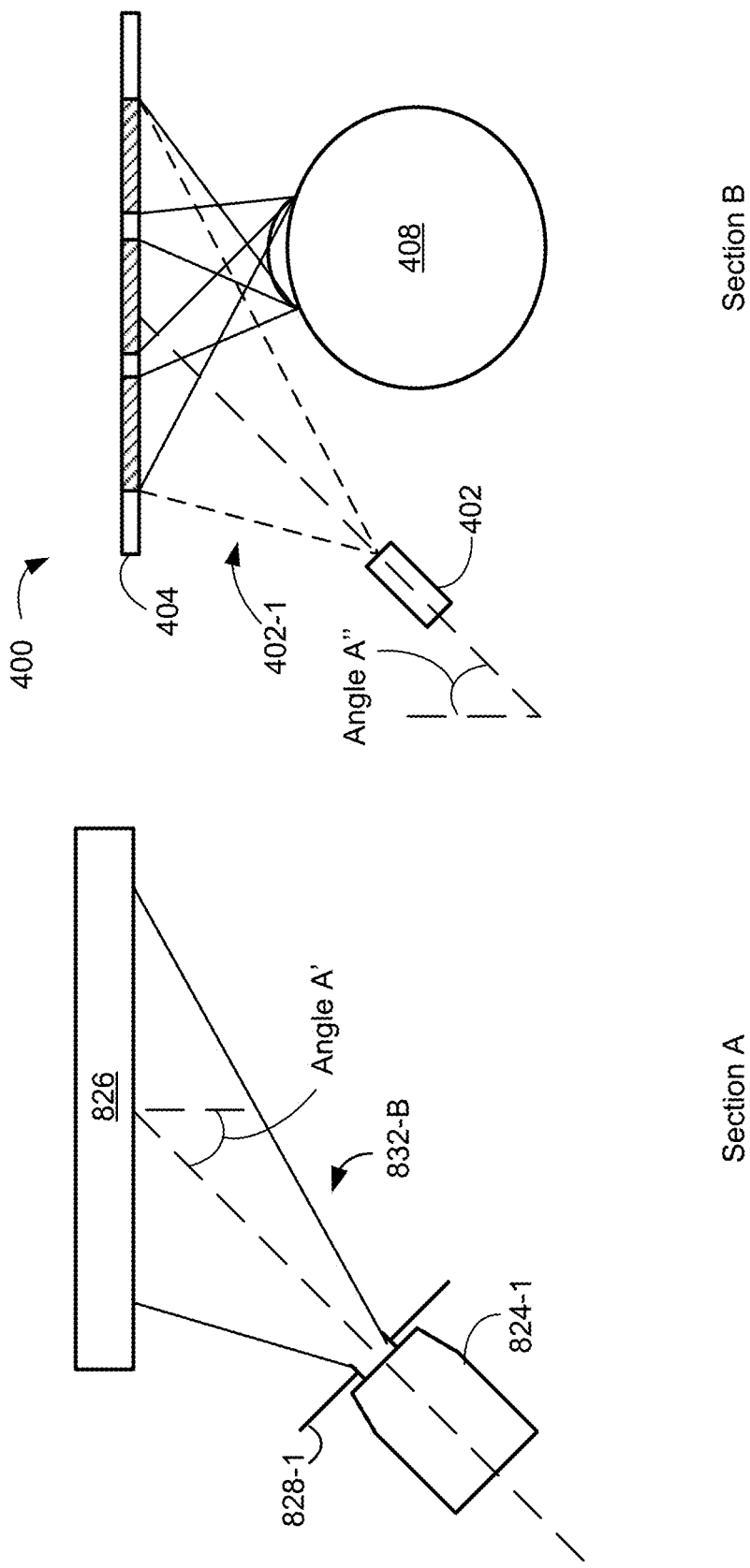
FIG. 8C is a schematic diagram illustrating adjustment of a direction of a reference beam onto an optically recordable medium for preparing a wide-field holographic medium in accordance with some embodiments.

FIG. 8C is a schematic diagram illustrating selection of a direction of reference beam 832-B onto optically recordable medium 826 for generating a wide-field holographic medium in accordance with some embodiments. Section A of FIG. 8C illustrates a portion of system 800 described above with respect to FIG. 8A including lens 824-1 transmitting beam 832-B through aperture 828-1 onto optically recordable medium 826. Angle A' describes an angle at which beam 832-B is transmitted by lens 824-1 toward optically recordable medium 826, with respect to a reference line perpendicular to optically recordable medium 826. Section B of FIG. 8C illustrates holographic illuminator 400 described above with respect to FIG. 4A with light source 402 and holographic medium 404 projecting a plurality of light patters toward eye 408. Angle A" describes an angle at which light 402-1 is projected toward holographic illuminator 404 by light source 402, with respect to a reference line perpendicular to holographic medium 404. In some embodiments, Angle A' at which beam 832-B in Section A is transmitted toward optically recordable medium 826 is selected to correspond to Angle A" at which light source 402 directs light 402-1 toward holographic medium 404. In some embodiments, Angle A' is adjusted by reflector 822-1 shown in FIG. 8A.

Figure 9A:
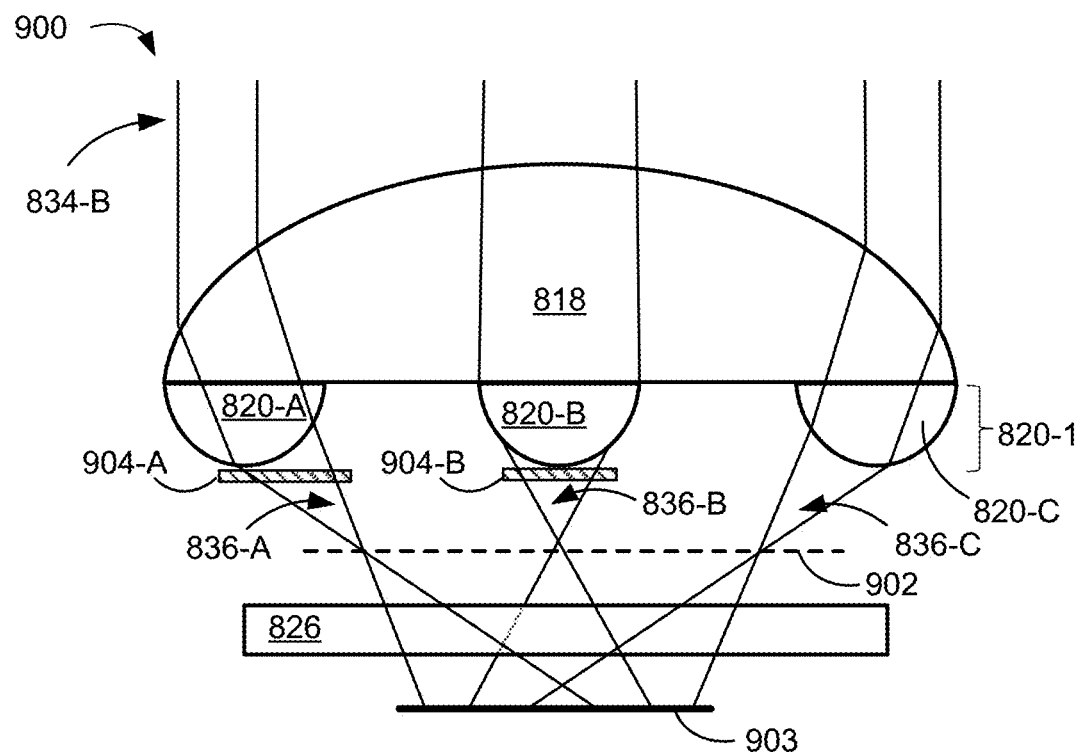
FIG. 9A is a schematic diagram illustrating a side view of optical elements for preparing a holographic medium in accordance with some embodiments.

FIG. 9A is a schematic diagram illustrating a side view of optical elements 900 for generating a holographic medium in accordance with some embodiments. Optical elements 900 is similar to the third set of optical elements 800-C described above with respect to FIG. 8A. In FIG. 9A, three lenses (e.g., lenses 820-A, 820-B, and 820-C) of lenses 820-1 are illustrated. Wide-field beam 834-B, received from the second set of optical elements 800-B in system 800, is transmitted through condenser lens 818. Condenser lens 818 is configured to transmit wide-field beam 834-B, through lenses 820-1, toward reference pupil 903 (e.g., in some cases, reference pupil 903 corresponding to a pupil of an eye of a user of a display device, such as eye 408 in FIG. 6A). In some embodiments, condenser lens 818 has a diameter ranging from 50 mm to 100 mm. In some embodiments, condenser lens 818 has a diameter of 75 mm.

Condenser lens 818 is optically coupled with lenses 820-1, including lenses 820-A, 820-B, and 820-C. In some embodiments, lenses 820-1 are attached to or coupled with condenser lens 808. In some embodiments, lenses 820-1 are positioned adjacent to, but separated from, condenser lens 808. In some embodiments, lenses 820-1 are positioned adjacent to optically recordable medium 826. Each lens of lenses 820-1 focuses a respective portion of wide-field beam 834-B as a respective light pattern of light patterns 836. In FIG. 9A, lens 820-A projects a portion of beam 834-B as pattern 836-A, lens 820-B projects a portion of beam 834-B as pattern 836-B, and lens 820-C projects a portion of beam 834-B as pattern 836-C. Pattern 836-A is projected toward optically recordable medium 826 at an angle different from an angle of projection of pattern 836-B. The angles at which light patterns 836-A and 836-B are projected toward the reference eye correspond to the respective angles at which light patterns 406-1 and 406-2 are projected toward the pupil of eye 408 in FIG. 4D. In some embodiments, light pattern 836-A projected by lens 820-A, which is the outermost lens of lenses 820-1, is projected toward reference pupil 903 (e.g., reference pupil 903 corresponding to eye 408 in FIG. 4D). In some embodiments, light pattern 836-A is projected toward reference pupil 903 at an angle ranging from 40 to 50 degrees. In some embodiments, light pattern 836-A is projected toward reference pupil 903 at an angle ranging from 50 to 55 degrees. In some embodiments, light pattern 836-A is projected toward reference pupil 903 at angle 45 degrees or more.

In FIG. 9A, light patterns 836 converge on reference plane 902. Reference plane 902 is positioned between optically recordable medium 826 and lenses 820-1. In some embodiments, reference line 902 corresponds to reference line 410-1 shown in FIG. 4A. In some embodiments, optical elements 900 are configured to form a holographic medium corresponding to holographic medium 404 in FIG. 4A. The holographic medium transmits light patterns 406-1, 406-2, and 402-3 toward eye 408 so that the convergence points of light patterns 406-1, 406-2, and 402-3 create a plurality of virtual single-point light sources near the surface of eye 408. In some embodiments, optical elements 900 are configured to form a holographic medium corresponding to holographic medium 424 in FIG. 4B that transmits light patterns 426-1, 426-2, and 426-3 toward eye 408 so that projected convergence points of light patterns 426-1, 426-2, and 426-3 create a plurality of virtual single-point light sources on an opposite side of holographic medium 424 (e.g., facing surface 424-1 of holographic medium 424).

In some embodiments, lenses 820-1 are coupled with a plurality of optical attenuators (e.g., attenuators 904-A and 904-B). Attenuator 904-A is coupled with lens 820-A and configured to attenuate an intensity of light pattern 836-A. Attenuator 904-B is coupled with lens 820-B and configured to attenuate an intensity of light pattern 836-B. In some embodiments, the attenuators are adjustable attenuators. In some embodiments, the attenuators are fixed intensity attenuators.

In some embodiments, lenses 820-A and 820-B are microlenses. In some embodiments, lenses 820-1 are arranged in a microlens array. Lenses 820-1 include a number of lenses ranging from seven to 2000. In some embodiments, the number of lenses ranges from seven to 20 lenses. In some embodiments, the number of lenses ranges from 20 to 1000 lenses. In some embodiments, the number of lenses ranges from 1000 to 2000 light lenses. In some embodiments, each lens of lenses 820-1 projects a light pattern corresponding to an area on the holographic medium, such that each area is configured to transmit a light pattern (e.g., areas 412-1, 412-2, and 412-3 of holographic medium 404 transmitting respective light patterns 406-1, 406-2, and 406-3 in FIG. 4A). In some embodiments, lenses 820-1 are arranged in a circular, rectangular, square, triangular, polygonal, distorted configuration (e.g., a pincushion shaped configuration) and/or any other uniform or non-uniform configuration. Lenses 820-1 are arranged to form an interference pattern that creates a holographic medium that projects a plurality of separate light patterns arranged in a particular configuration, including any of the configurations described above with respect to FIGS. 5A-5F.

Figure 9B:
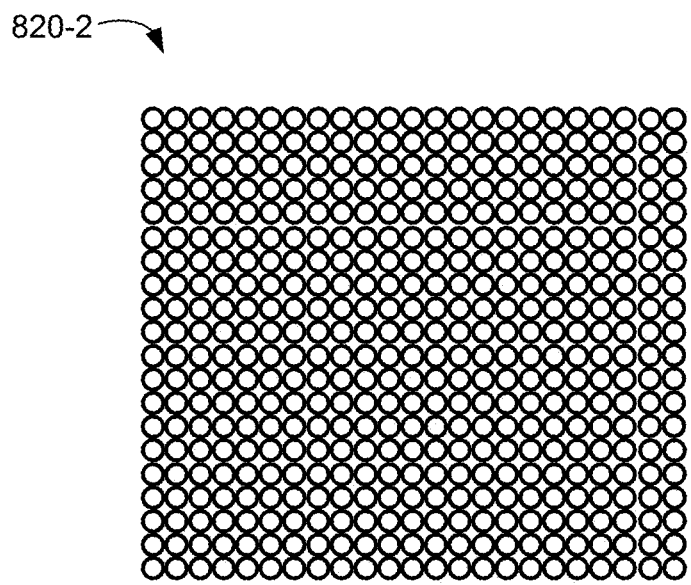
FIG. 9B is a schematic diagram illustrating a plan view of lenses for preparing a holographic medium in accordance with some embodiments.

FIG. 9B is a schematic diagram illustrating a plan view of lenses 820-2 (e.g., a lens array) for generating a holographic medium in accordance with some embodiments. In some embodiments, lenses 820-2 correspond to lenses 820-1 described with respect to FIG. 9A (e.g., lenses 820-1 are arranged in the configuration shown in FIG. 9B). FIG. 9B includes an array of 20 by 20 lenses arranged in a rectangular configuration.

Figure 9C:
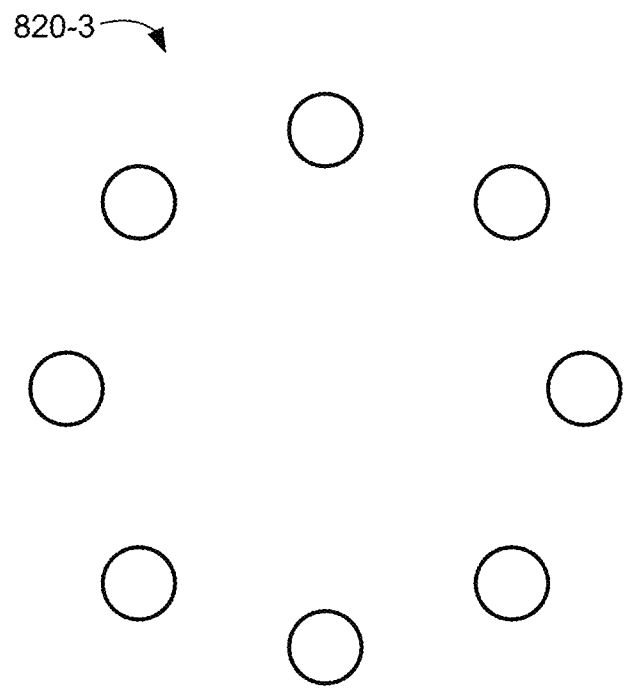
FIG. 9C is a schematic diagram illustrating a plan view of lenses for preparing a holographic medium in accordance with some embodiments.

FIG. 9C is a schematic diagram illustrating a plan view of lenses 820-3 for generating a holographic medium in accordance with some embodiments. In some embodiments, lenses 820-3 correspond to lenses 820-1 described with respect to FIG. 9A (e.g., lenses 820-1 are arranged in the configuration shown in FIG. 9C). FIG. 9C includes a lens array including eight lenses in a circular configuration.

Figure 9D:
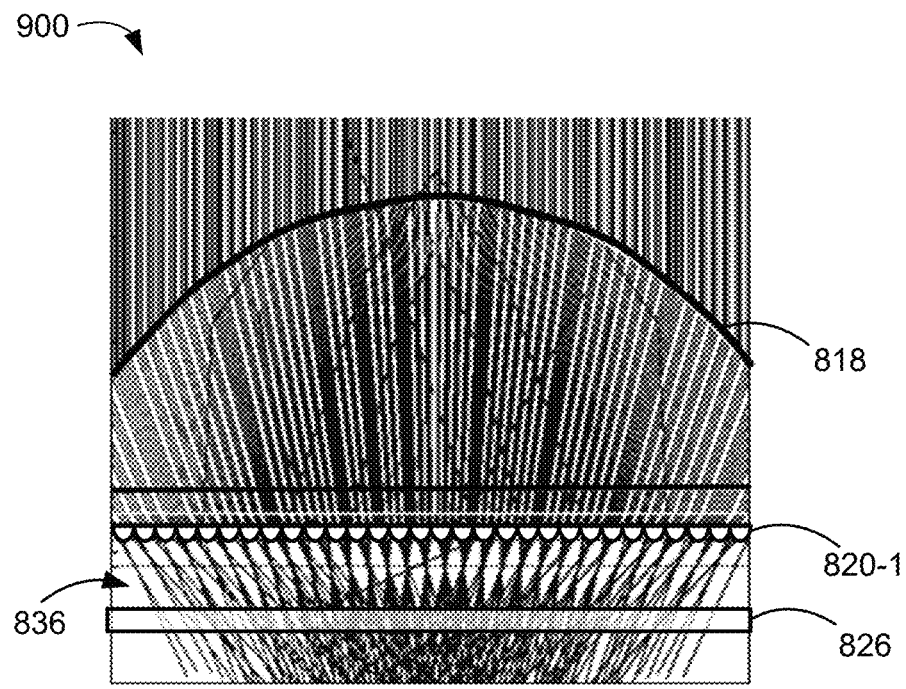
FIG. 9D is a schematic diagram illustrating a side view of optical elements for preparing a holographic medium in accordance with some embodiments.

FIG. 9D is a schematic diagram illustrating a side view of optical elements 900 for generating a holographic medium in accordance with some embodiments. In some embodiments, lenses 921 include 30 or more lenses (e.g., a microlens array of lenses). FIG. 9D also illustrates optical paths of a plurality of rays being transmitted through condenser lens 818, and projected by lenses 820-1 toward optically recordable medium 826 as a plurality of light patterns 936.

Figure 9E:
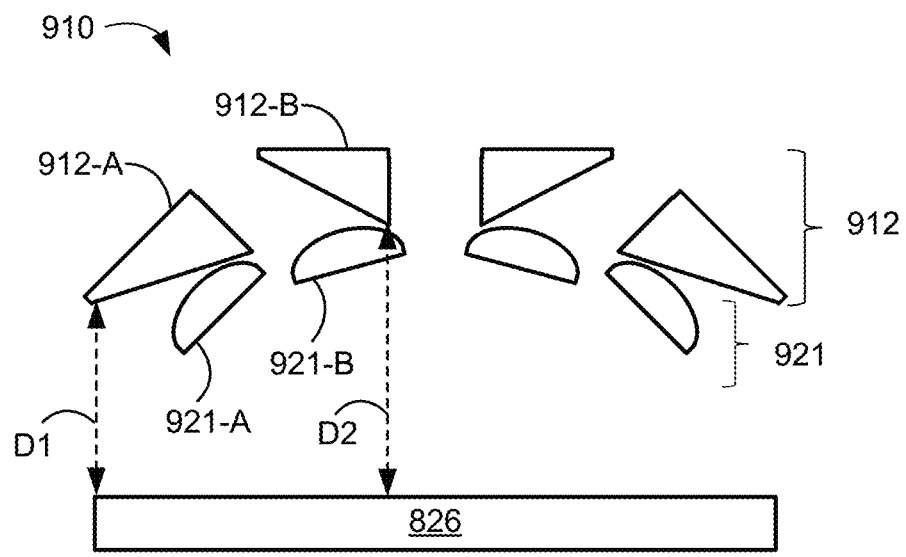
FIG. 9E is a schematic diagram illustrating a side view of optical elements for preparing a holographic medium in accordance with some embodiments.

FIG. 9E is a schematic diagram illustrating a side view of optical elements 910 for generating a holographic medium in accordance with some embodiments. Optical elements 910 are similar to the third set of optical elements 800-C described above with respect to FIG. 8A for providing a plurality of light patterns (e.g., light patterns 836) onto optically recordable medium 826 for forming a holographic medium, expect that optical elements 910 include prisms 912 (e.g., prisms 912-A and 912-B). Prisms 912 are configured to received wide-field beam 834-B and project the beam as a plurality of beams onto optically recordable medium 826. In some embodiments, the number of prisms 912 and/or the configurations of prisms 912 are selected to provide any configuration of a plurality of light patterns described herein (e.g., configurations illustrated in FIGS. 5A-5F). In some embodiments, prisms 912 are optically coupled with lenses 921, as shown in FIG. 9E. Lenses 921 receive the plurality of beams projected by prisms 912 and project a plurality of light patterns toward optically recordable medium 826 in a manner similar to lenses 820-1 described with respect to FIG. 9A.

In FIG. 9E, lenses 921 and prisms 912 are arranged in a dome configuration adjacent to optically recordable medium 826, so that the peripheral prisms and lenses (e.g., prism 912-A and lens 921-A) are positioned closer to optically recordable medium 826 than the prisms and lenses positioned in the center (e.g., prism 912-B and lens 921-B). For example, distance D1 between prism 912-A and optically recordable medium 826 is less than distance D2 between prism 912-B and optically recordable medium 826. Similarly, a distance between lens 921-A and optically recordable medium 826 is less than a distance between lens 921-B and optically recordable medium 826.

Figure 9F:
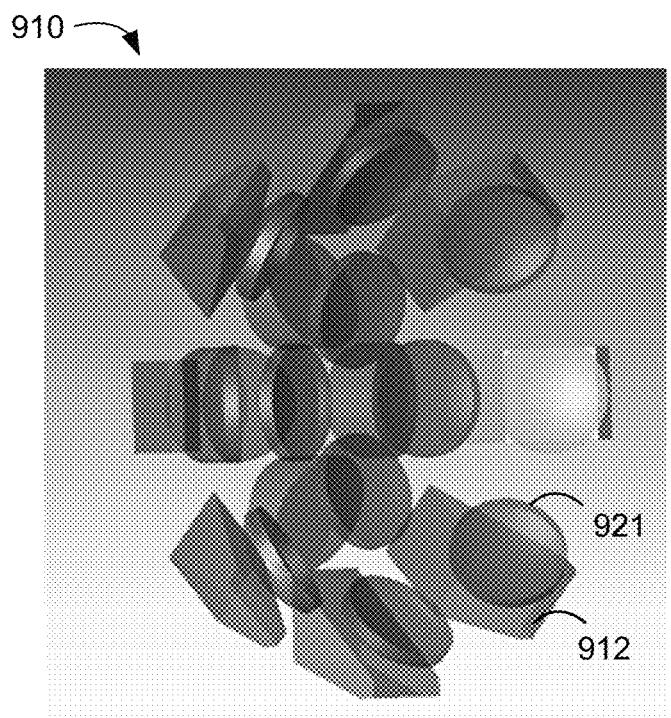
FIG. 9F is a schematic diagram illustrating optical elements for preparing a holographic medium in accordance with some embodiments.

FIG. 9F is a schematic diagram illustrating optical elements 910 for generating a holographic medium in accordance with some embodiments. FIG. 9F illustrates a three-dimensional view of optical elements 910 including prisms 912 optically coupled with lenses 921. In some embodiments, prisms 912 are arranged in multiple concentric circles defining a dome configuration. In FIG. 9F, prisms 912 includes twelve prisms arranged in a dome configuration (e.g., four prisms in an inner circle and eight prisms in an outer circle).

Figure 9G:
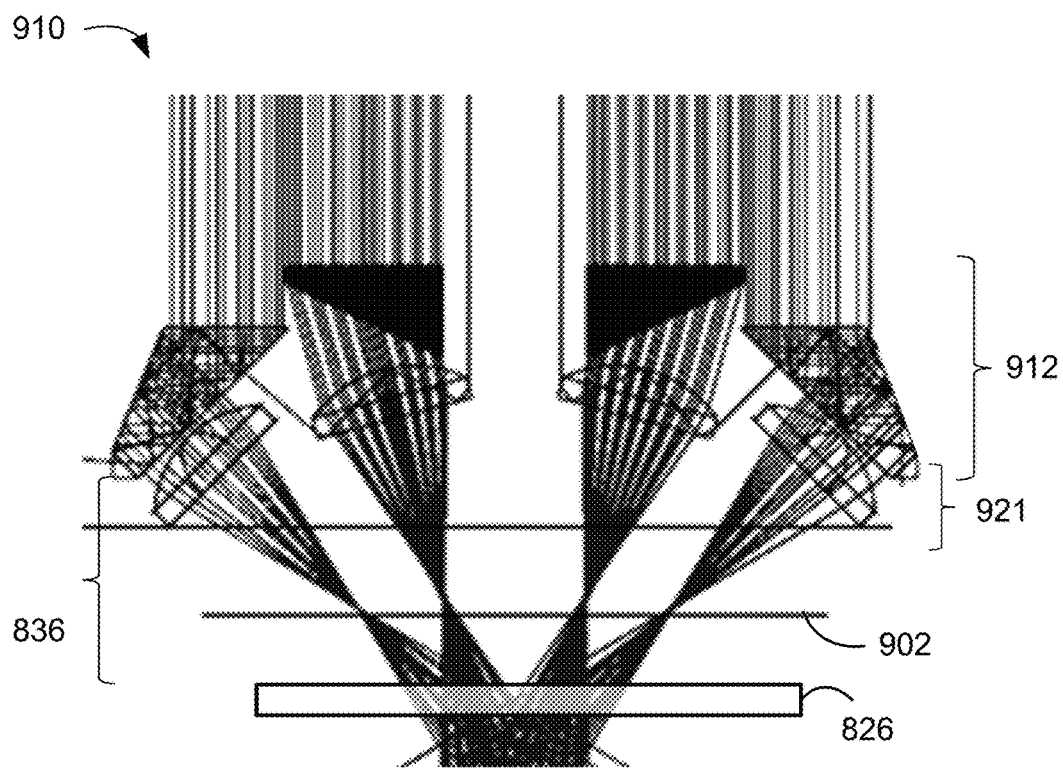
FIG. 9G is a schematic diagram illustrating a side view of optical elements for preparing a holographic medium in accordance with some embodiments.

FIG. 9G is a schematic diagram illustrating a side view of optical elements 910 for generating a holographic medium in accordance with some embodiments. FIG. 9G illustrates optical paths of a plurality of rays being transmitted through prisms 912 and lenses 921 toward optically recordable medium 826.

Figure 9H:
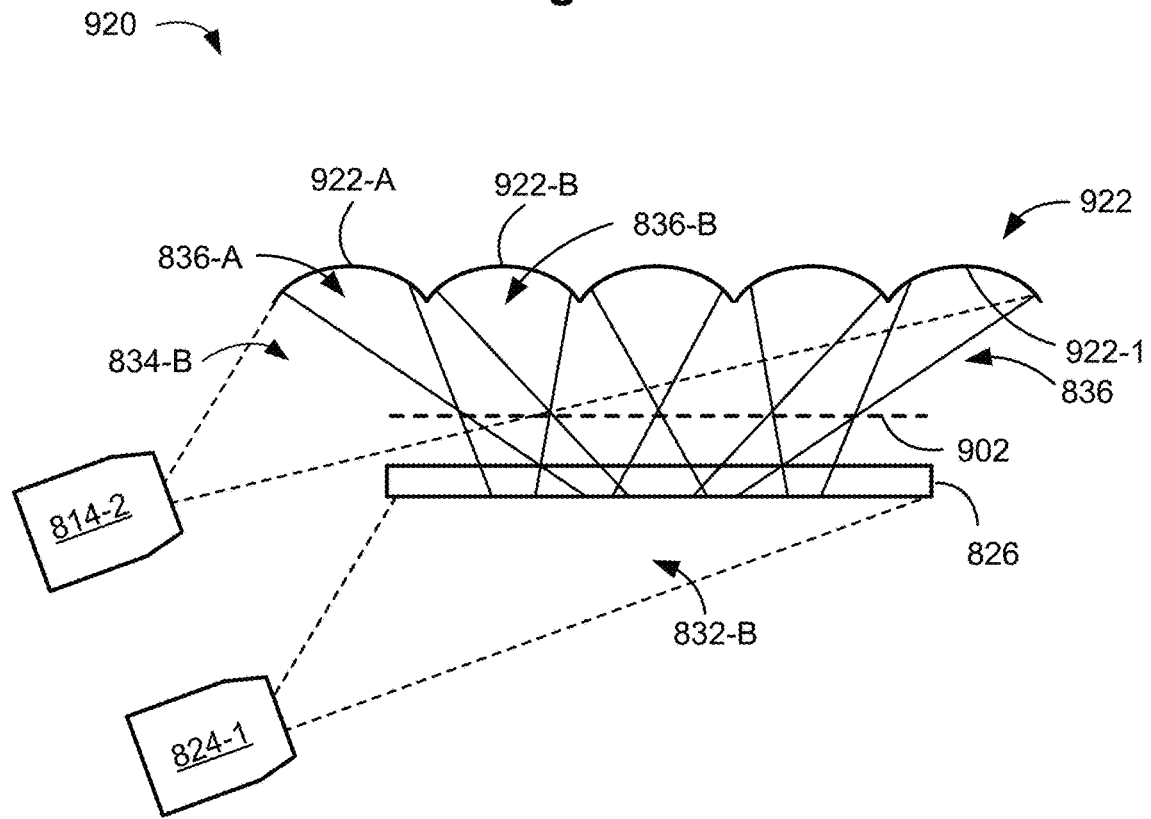
FIGS. 9H-9J are schematic diagrams illustrating side views of optical elements for preparing a holographic medium in accordance with some embodiments.
Figure 9I:
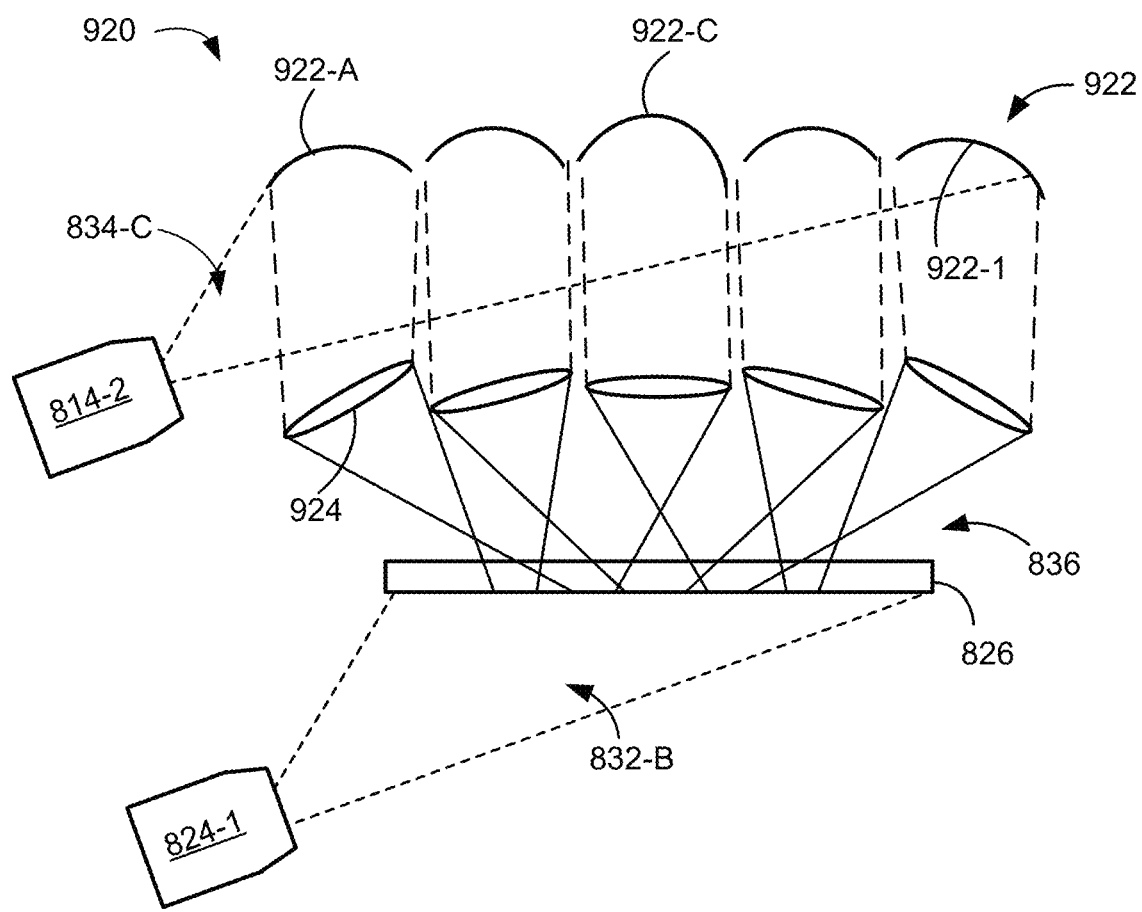
Figure 9J:
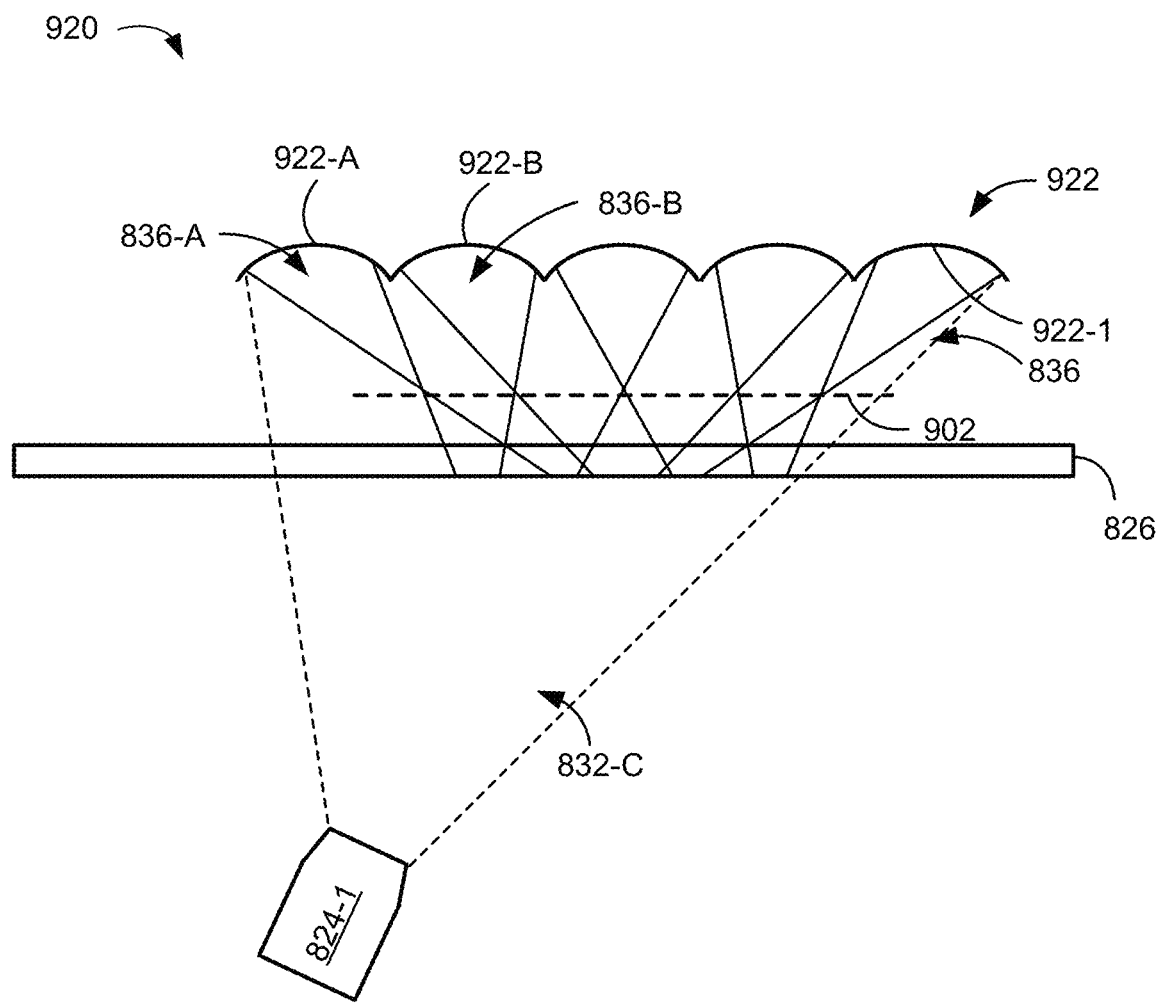

FIGS. 9H-9J are schematic diagrams illustrating side views of optical elements 920 for generating a holographic medium in accordance with some embodiments. Optical elements 920 are similar to the third set of optical elements 800-C described above with respect to FIG. 8A for providing a plurality of light patterns (e.g., light patterns 836) onto optically recordable medium 826 for forming a holographic medium, expect that optical elements 920 include parabolic reflectors 922 (e.g., parabolic reflectors 922-A and 922-B) instead of lenses 820. In some embodiments, parabolic reflectors 922 are replaced by ellipsoidal reflectors and/or freeform shaped reflectors. In some embodiments, the number of parabolic reflectors 922 and/or the configurations of parabolic reflectors 922 are selected to provide any configuration of a plurality of light patterns described herein (e.g., configurations illustrated in FIGS. 5A-5F). In some implementations, parabolic reflectors 922 include reflective surfaces 922-1 facing optically recordable medium 826. In FIG. 9H, wide-field beam 834-B is projected toward parabolic reflectors 922 (e.g., off-axis) such that beam 834-B is received by reflective surfaces 922-1 of parabolic reflectors 922 and reflected by reflective surfaces 922-1 onto optically recordable medium 826 as a plurality of light patterns 836 (e.g., in-line). In some embodiments, wide-field beam 834-B is projected by lens 814-2 corresponding to lens 814-1 of the second set of optical elements 800-B.

In some implementations, parabolic reflectors 922 project light patterns 836 converging on reference plane 902 positioned between optically recordable medium 826 and parabolic reflectors 922, similar to lenses 820-1 in FIG. 9A. In some embodiments, reference line 902 corresponds to reference line 410-1 in FIG. 4A.

In some embodiments, parabolic reflectors 922 have identical shapes (e.g., curvature) and sizes (e.g., diameter). For example, in FIG. 9H, parabolic reflector 922-A is identical to parabolic reflector 922-B. In some embodiments, parabolic reflectors 922 have different shapes and sizes. For example, parabolic reflector 922-A has a curvature different from a curvature of parabolic reflector 922-C in FIG. 9I. In some embodiments, parabolic reflectors are attached to or coupled with each other, as shown in FIG. 9H. In some embodiments, parabolic reflectors are separated from each other, as shown in FIG. 9I.

In some embodiments, optical elements 920 including parabolic reflectors 922 are used in an illumination configuration using a single-beam. In FIG. 9J, lens 824-1 is configured to provide beam 832-C that is transmitted through recordable medium 826 toward parabolic reflectors 922. Beam 832-C is reflected off reflective surfaces 922-1 of parabolic reflectors 922 onto optically recordable medium 826 as a plurality of light patterns 836 (e.g., in-line). A holographic medium (e.g., holographic medium 404 described above with respect to FIG. 4A) is therefore created by using a single beam (e.g., beam 832-C) illumination.

Figure 9K:
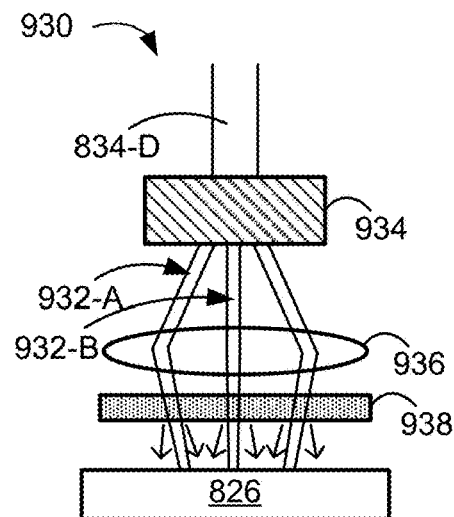
FIG. 9K is a schematic diagram illustrating a side view of optical elements for preparing a holographic medium in accordance with some embodiments.

FIG. 9K is a schematic diagram illustrating a side view of optical elements 930 for generating a holographic medium in accordance with some embodiments. Optical elements 930 is similar to the third set of optical elements 800-C described above with respect to FIG. 8A for providing a plurality of light patterns (e.g., light patterns 932-A and 932-B) onto optically recordable medium 826 for forming a holographic medium, expect that optical elements 930 include diffractive optical element (DOE) 934. In some embodiments, optical elements 930 include two or more diffractive optical elements 934. DOE 934 receives beam 834-D. Beam 834-D does not need to be a wide-field beam. In some embodiments, beam 834-D corresponds to beam 834-A shown in FIG. 8A. DOE 934 projects beam 834-D as a plurality of light patterns (e.g., light patterns 932-A and 932-B) onto optically recordable medium 826. In some embodiments, DOE 934 is configured to provide any configuration of a plurality of light patterns described herein (e.g., configurations illustrated in FIGS. 5A-5F). In some embodiments, DOE 934 is used to form holographic mediums described above with respect to FIGS. 4A-4B. In some embodiments, DOE 934 is used to form holographic mediums described above with respect to FIG. 4C.

In some embodiments, DOE 934 includes one or more diffractive beam splitters configured to project an array of spots (e.g., an array of light patterns including light patterns 932-A and 932-B). In some embodiments, DOE 934 includes one or more diffractive diffusers for modifying the projected light patterns. In some embodiments, DOE 934 is optically coupled with lens 936 (e.g., lens 936 is a condenser lens), which focuses the plurality of light patterns including light patterns 932-A and 932-B. In some embodiments, DOE 934 is coupled with a plurality of lenses, such as lenses 820-1 described above with respect to FIG. 9A. For example, DOE 934 is coupled with lens 820-A configured to focus light pattern 932-A and with lens 820-B configured to focus light pattern 932-B. In some embodiments, optical elements 930 further include diffuser 938 optically coupled with DOE 934 and/or lens 936. Diffuser 938 diffuses light, thereby expanding light patterns 932 projected onto optically recordable medium 826. In some embodiments, diffuser 938 is used to reduce or eliminate high (spatial) frequency variation in the plurality of light patterns.

Figure 9L:
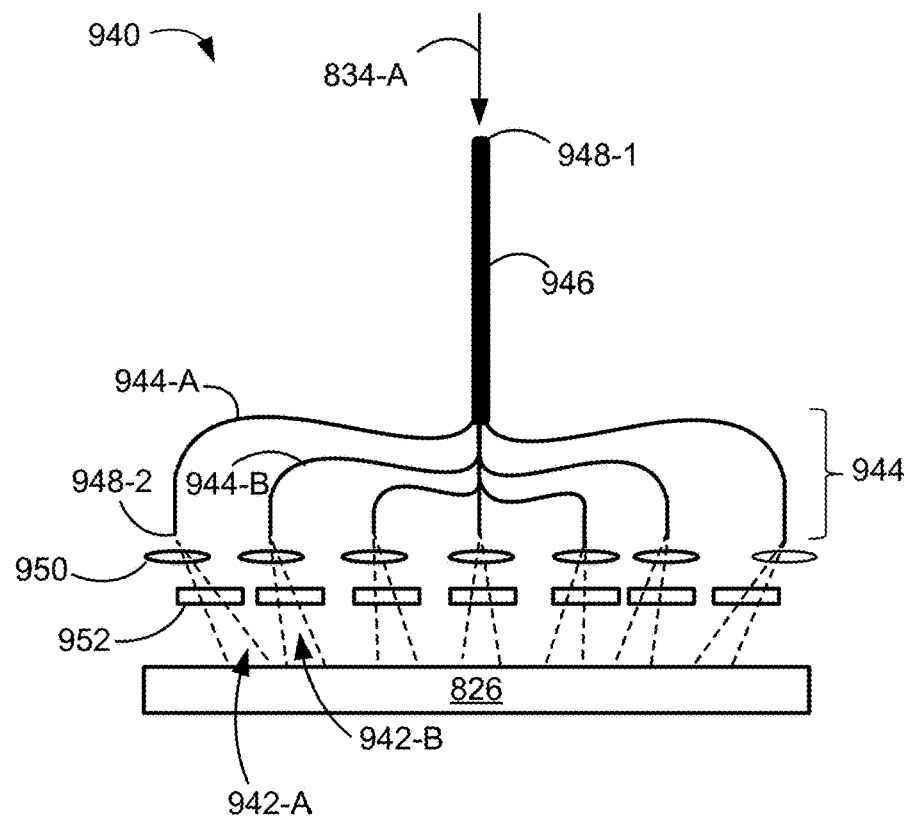
FIG. 9L is a schematic diagram illustrating a side view of optical elements for preparing a holographic medium in accordance with some embodiments.

FIG. 9L is a schematic diagram illustrating a side view of optical elements 940 for generating a holographic medium in accordance with some embodiments. Optical elements 940 are similar to the third set of optical elements 800-C described above with respect to FIG. 8A for providing a plurality of light patterns (e.g., light patterns 942) onto optically recordable medium 826 for forming a holographic medium, expect that optical elements 940 include optical fibers 944 (e.g., optical fibers 944-A and 944-B). Each optical fiber (e.g., optical fiber 944-A) is configured to receive a portion of light (e.g., beam 834-A) projected by light source 802 in FIG. 8A onto input fiber end 948-1 and project the beam as a light pattern (e.g., light pattern 942-A) onto optically recordable medium 826 from output fiber end 948-2. In some embodiments, optical fibers 944 are optically coupled to light source 802 through a single fiber (e.g., a multi-mode fiber). In some embodiments, optical fibers 944 are optically coupled to light source 802 as bundle 946 of optical fibers. In some embodiments, optical fibers 944 are optically coupled to beam splitter 810 and optionally to polarizer 814-1 and are configured to receive beam 834-A described with respect to FIG. 8A. In some embodiments, optical fibers 944 are coupled with other optical elements (e.g., one or more lenses) for receiving beam 834-A. In some embodiments, optical fibers 944 are single-mode optical fibers. In some embodiments, optical fibers 944 are multi-mode optical fibers.

In some embodiments, optical fibers 944 (e.g., output fiber ends 948-2 of optical fibers 944) are configured to provide any configuration of a plurality of light patterns described herein (e.g., configurations illustrated in FIGS. 5A-5F). In some embodiments, optical fibers 944 are used to form holographic mediums described above with respect to FIGS. 4A-4B. In some embodiments, optical fibers 944 are used to form holographic mediums described above with respect to FIG. 4C.

In some embodiments, optical fibers 944 are coupled with lenses 950. In some embodiments, lenses 950 are arranged in a microlens array. In some embodiments, optical fibers 944 are coupled with a single lens (e.g., a condenser lens), such as lens 936 described above with respect to FIG. 9K.

In some embodiments, optical fibers 944 are coupled with plurality of filters 952 (e.g., color filters). In some embodiments, filters 952 are configured to modify a wavelength (e.g., color) of light patterns 942 provided by optical fibers 944. In some embodiments, optical fibers 944 are optically coupled with one or more attenuators, such as attenuators 904-A and 904-B described above with respect to FIG. 9A.

In light of these principles, we now turn to certain embodiments.

In accordance with some embodiments, a method for making a holographic medium includes providing light from a light source (e.g., light source 802 provides beam 830 in FIG. 8A) and separating the light into a first portion of the light and a second portion of the light that is spatially separated from the first portion of the light (e.g., beam splitter 810 separates beam 830 into beam 832-A and 834-A). The method also includes transmitting the first portion of the light through a first set of optical elements (e.g., the first set of optical elements 800-A) to provide a first wide-field beam (e.g., beam 832-B), transmitting the second portion of the light through a second set of optical elements (e.g., the second set of optical elements 800-B) to provide a second wide-field beam (e.g., beam 834-B) that is spatially separated from the first wide-field beam, and transmitting the second wide-field beam through a third set of optical elements (e.g., the third set of optical elements 800-C) to provide a plurality of separate light patterns (e.g., light patterns 836). The method further includes concurrently projecting the first wide-field beam and the plurality of separate light patterns onto an optically recordable medium to form a holographic medium (e.g., beam 832-B and light patterns 836 are concurrently projected on optically recordable medium 826 to form a holographic medium). In some embodiments, the light is coherent light, such as a laser beam.

In some embodiments, the first wide-field beam is projected onto the optically recordable medium through a first surface of the optically recordable medium (e.g., beam 832-B is projected onto surface 826-1 of optically recordable medium 826 in FIG. 8A) and the plurality of separate light patterns is projected onto the optically recordable medium through a second surface of the optically recordable medium that is opposite to the first surface of the optically recordable medium (e.g., light patterns 836 are projected onto surface 826-2 of optically recordable medium 826).

In some embodiments, the first wide-field beam and the plurality of separate light patterns are projected onto the optically recordable medium through a first surface of the optically recordable medium (e.g., beam 832-B and light patterns 836 are projected onto surface 826-2 of optically recordable medium 826 in FIG. 8B).

In some embodiments, the first set of optical elements is located away from an optical axis of the holographic medium (e.g., the first set of optical elements 800-A is located away from an optical axis of optically recordable medium 826 forming the holographic medium, as shown in FIG. 8A), and projecting the first wide-field beam onto the optically recordable medium to form the holographic medium includes projecting the first wide-field beam onto the holographic medium at a first angle (e.g., beam 832-B is projected onto holographic medium 826 at Angle A' as shown in Section A of FIG. 8C).

In some embodiments, at least a subset of the second set of optical elements is located to intersect with an optical axis of the holographic medium (e.g., parabolic reflector 816 of the second set of optical elements 800-B is located or positioned to intersect with an optical axis of optically recordable medium 826 that forms the holographic medium), and projecting the second wide-field beam onto the optically recordable medium to form the holographic medium includes projecting the second wide-field beam onto the holographic medium at a second angle that is distinct from the first angle (e.g., beam 832-B and beam 834-B are projected onto optically recordable medium 826 at different angles as shown in FIG. 8A). For example, in some implementations, the first wide-field beam is projected onto the holographic medium at an off-axis angle (e.g., 45 degrees) and the second wide-field beam is projected onto the holographic medium at an on-axis angle (e.g., a projection angle of 0 degree).

In some embodiments, the first set of optical elements includes a first lens (e.g., lens 824-1 in FIG. 8A) and the second set of optical elements includes a second lens (e.g., lens 814-1) that is distinct and separate from the first lens. In some embodiments, lenses 824-1 and 814-1 are microscopic objectives.

In some embodiments, the second set of optical elements includes a parabolic reflector (e.g., parabolic reflector 816 in FIG. 8A) optically coupled with the second lens (e.g., lens 814-1), and transmitting the second portion of the light through the second set of optical elements includes, with the parabolic reflector, receiving the first portion of the light (e.g., parabolic reflector 816 receives beam 834-A) and collimating the first portion of the light to provide the second wide-field beam (e.g., parabolic reflector 816 collimates beam 834-A and provides wide-field beam 834-B).

In some embodiments, the third set of optical elements includes a plurality of lenses (e.g., the third set of optical elements 800-C includes lenses 820 in FIG. 8A). In some embodiments, the plurality of lenses includes a first pattern lens and a second pattern lens distinct and separate from the first pattern lens (e.g., lenses 820-A and 820-B in FIG. 9A). The method includes projecting, with the first pattern lens, a first portion of the plurality of separate light patterns onto the optically recordable medium (e.g., projecting light pattern 836-A with lens 820-A onto optically recordable medium 826), and projecting, with the second pattern lens, a second portion of the plurality of separate light patterns onto the optically recordable medium (e.g., projecting light pattern 836-B with lens 820-B onto optically recordable medium 826).

In accordance with some embodiments, a system for making a holographic medium includes a light source configured to provide light, and a beam splitter configured to separate the light into a first portion of the light and a second portion of the light that is spatially separated from the first portion of the light (e.g., light source 802 and beam splitter 810 in FIG. 8A). The system also includes (i) a first set of optical elements (e.g., the first set of optical elements 800-A) configured to transmit the first portion of the light for providing a first wide-field beam, (ii) a second set of optical elements (e.g., the second set of optical elements 800-B) configured to transmit the second portion of the light for providing a second wide-field beam, and (iii) a third set of optical elements (e.g., the third set of optical elements 800-C) optically coupled with the second set of optical elements and configured to transmit the second wide-field beam for providing a plurality of separate light patterns onto an optically recordable medium for forming the holographic medium.

In some embodiments, the first set of optical elements is configured to project the first wide-field beam onto the optically recordable medium through a first surface of the optically recordable medium (e.g., surface 826-1 in FIG. 8A). The second set of optical elements and the third set of optical elements are configured to project the plurality of separate light patterns onto the optically recordable medium through a second surface of the optically recordable medium that is opposite to the first surface of the optically recordable medium (e.g., surface 826-2 in FIG. 8A).

In some embodiments, the first set of optical elements, the second set of optical elements, and the third set of optical elements are configured to project the first wide-field beam and the plurality of separate light patterns onto the optically recordable medium through a first surface of the optically recordable medium (e.g., surface 826-2 in FIG. 8B).

In some embodiments, the first set of optical elements is located away from an optical axis of the holographic medium (e.g., an axis that is perpendicular to the holographic medium), and projecting the first wide-field beam onto the optically recordable medium to form the holographic medium includes projecting the first wide-field beam onto the holographic medium at a first angle (e.g., FIG. 8A).

In some embodiments, at least a subset of the second set of optical elements is located to intersect with an optical axis of the holographic medium, and projecting the second wide-field beam onto the optically recordable medium to form the holographic medium includes projecting the second wide-field beam onto the holographic medium at a second angle that is distinct from the first angle (e.g., FIG. 8A).

In some embodiments, the first set of optical elements includes a first lens (e.g., lens 824-1 in FIG. 8A) and the second set of optical elements includes a second lens that is distinct and separate from the first lens (e.g., lens 814-1 in FIG. 8A). In some embodiments, the first lens is a first objective (e.g., a microscope objective). In some embodiments, the second lens is a second objective (e.g., a microscope objective). In some embodiments, the first objective is coupled with an aperture (e.g., aperture 828-1 in FIG. 8A).

In some embodiments, the first set of optical elements includes an adjustable reflector configured to direct the first portion of the light toward the first lens (e.g., reflector 822-1 in FIG. 8A). In some embodiments, an angular position of the adjustable reflector is selected according to the angle for projecting the eye tracking light from the light source in a head-mounted display device. For example, in FIG. 8C, the angle at which beam 832-B is transmitted toward optically recordable medium 826 (e.g., Angle A') is adjusted to correspond to the angle at which beam 402-1 is projected toward holographic medium 404 (e.g., Angle A'') in holographic illuminator 400.

In some embodiments, the second set of optical elements includes a parabolic reflector optically coupled with the second lens and configured to collimate the first portion of the light to provide the second wide-field beam (e.g., parabolic reflector 816 in FIG. 8A). In some embodiments, the parabolic reflector is positioned at a 45-degree angle with respect to the direction of the second portion of the light. In some embodiments, the parabolic reflector is configured to provide the second wide-field beam having a diameter of at least 100 mm (e.g., beam 834-B has a diameter of at least 100 mm).

In some embodiments, the third set of optical elements includes a plurality of lenses (e.g., lenses 820 in FIG. 8A). In some embodiments, the plurality of lenses is arranged in a circular configuration (e.g., lenses 820-3 are arranged in a circular configuration in FIG. 9C).

In some embodiments, the beam splitter is a polarizing beam splitter (e.g., beam splitter 810 in FIG. 8A) configured to separate the light into the first portion of the light having a first polarization (e.g., beam 832-A has a first polarization, such as a horizontal polarization) and the second portion of the light having a second polarization (e.g., beam 834-A has a second polarization, such as a vertical polarization) that is distinct from the first polarization. In some embodiments, the light source is a laser (e.g., light source 802 is a laser). In some embodiments, the light source is coupled with a polarizer (e.g., polarizer 808). In some embodiments, the light source is coupled with a beam expander (e.g., beam expander 804) and an aperture (e.g., aperture 806).

In some embodiments, the first set of optical elements includes a polarizer for adjusting a polarization of the first portion of the light and/or the second set of optical elements includes a polarizer (e.g., a half-wave plate) for adjusting a polarization of the second portion of the light. For example, polarizer 812 (e.g., a half-wave plate) adjusts the polarization of beam 834-A in FIG. 8A.

In accordance with some embodiments, a holographic medium is made by any of the methods described herein (e.g., holographic medium 404 in FIG. 4A).

In accordance with some embodiments, an eye tracker includes a light source (e.g., light source 402 in FIG. 6A), the holographic medium (e.g., holographic medium 404) optically coupled with the light source and a detector (e.g., detector 602). The holographic medium is configured to receive light (e.g., light 402-1) provided from the light source and project a plurality of separate light patterns (e.g., light patterns 406-1, 406-2, and 406-3) concurrently toward an eye. In some embodiments, a respective pattern of the plurality of separate light patterns is a spot (e.g., a circular spot, a rectangular spot, etc. as shown in FIGS. 5A, 5C, and 5D). In some embodiments, a respective pattern of the plurality of separate light pattern is a line (e.g., a straight line as shown in FIG. 5B or a curved line).

The detector is configured to detect a reflection (e.g., an image of an area defined by rays 608-1) of at least a subset of the plurality of separate light patterns, reflected off the eye, for determining a location of a pupil of the eye (e.g., eye 408).

In accordance with some embodiments, a head-mounted display device includes one or more optical elements (e.g., one or more lenses), one or more displays configured to project light through or off of the one or more optical elements toward an eye of a wearer of the head-mounted display device, and the eye tracker described herein (e.g., display device 600 in FIG. 6A). In some embodiments, the one or more optical elements include one or more combiners (e.g., combiner 644 in FIG. 6D).

In accordance with some embodiments, an eye-tracking system includes a holographic illuminator that includes a light source configured to provide light and a holographic medium optically coupled with the light source (e.g., holographic illuminator 400 includes light source 402 and holographic medium 404 as shown in FIG. 4A). The holographic medium is configured to receive the light provided from the light source (e.g., light 402-1) and project a plurality of separate light patterns concurrently toward an eye (e.g., light patterns 406-1, 406-2, and 406-3 are projected toward eye 408). The eye-tracking system also includes a detector configured to detect a reflection of at least a subset of the plurality of separate light patterns, reflected off the eye, for determining a location of a pupil of the eye (e.g., detector 602 in FIG. 6A).

In some embodiments, the holographic medium is configured to transmit a concurrent projection of the plurality of separate light patterns (e.g., light patterns 406-1, 406-2, and 406-3). In some embodiments, the resultant glints (e.g., reflections) have identifiable signatures, such as location, intensity, and shape, for eye tracking (e.g., FIG. 7B illustrates a plurality of separate glints with identifiable signatures).

In some embodiments, the light source is a single-point light source (e.g., light source 402 in FIG. 4A is a single-point light source). In some embodiments, the light source is a wide-field light source. In some embodiments, the light projected by the light source is collimated.

In some embodiments, the light source is located away from an optical axis of the holographic medium (e.g., light source 402 is located away from an optical axis of holographic medium 404 in FIG. 4A). In some embodiments, the light source is on the optical axis of the holographic medium.

In some embodiments, the holographic medium is a reflection holographic medium configured to receive the light from the light source on a first surface of the holographic medium (e.g., surface 404-2 of holographic medium 404 in FIG. 4A) and concurrently project (e.g., reflect, diffract, etc.) the plurality of separate light patterns through the first surface of the holographic medium.

In some embodiments, the holographic medium is a transmission holographic medium configured to receive the light from the light source on a first surface of the holographic medium (e.g., surface 404-1 of holographic medium 404 in FIG. 4C) and concurrently project (e.g., transmit, diffract, etc.) the plurality of separate light patterns through a second surface of the holographic medium (e.g., surface 404-2 of holographic medium 404) that is opposite to the first surface of the holographic medium.

In some embodiments, the plurality of separate light patterns includes a first light pattern (e.g., light pattern 406-1 in FIG. 4D) and a second light pattern distinct and separate from the first light pattern (e.g., light pattern 406-2). The first light pattern of the plurality of separate light patterns is projected toward the eye at a first angle (e.g., the angle defined by reference line 442 and reference line 440) and the second light pattern of the plurality of separate light patterns is projected toward the eye at a second angle (e.g., the angle defined by reference line 444 and reference line 440) distinct from the first angle. In some embodiments, the first light pattern and the second light pattern have the same shape when projected on the eye. In some embodiments, the first light pattern and the second light pattern have different shapes when projected on the eye.

In some embodiments, the plurality of separate light patterns is arranged in a circular configuration (e.g., in FIG. 5A, configuration 502 includes light patterns 502-1, 502-2, and 502-3 arranged in a circular configuration). In some embodiments, the circular configuration includes a plurality of separate spots along a periphery of a reference circle. In some embodiments, the plurality of separate light patterns is arranged in a striped, rectangular, sinusoidal, crossed, or non-uniform configuration (e.g., FIG. 5B).

In some embodiments, the plurality of separate light patterns arranged in the circular configuration is configured to illuminate an area with a diameter of at least 10 mm on a surface of the eye. For example, light patterns 704 in Section A of FIG. 7B span over an area with a diameter of at least 10 mm on a surface of an eye.

In some embodiments, the plurality of separate light patterns is arranged in a distorted configuration (e.g., a non-rectangular and non-circular configuration, such as a pincushion configuration) that counters for a contoured surface of the eye so that the at least a subset of the plurality of separate light patterns reflected off the contoured surface of the eye is arranged in a non-distorted configuration. For example, FIG. 7B illustrates that reflection of the plurality of light patterns arranged in the pincushion configuration (as shown in section A of FIG. 7B) off one or more surfaces of an eye is in a substantially non-distorted configuration, such as a rectangular configuration (as shown in section B of FIG. 7B).

In some embodiments, the holographic medium is configured to project the plurality of separate light patterns concurrently so that each light pattern of the plurality of separate light patterns converges in proximity to a surface of the eye (e.g., light patterns 406-1, 406-2, and 406-3 converge on a reference plane 410-1 in FIG. 4A). In some implementations, the convergence points create a plurality of virtual single-point light sources near the surface of the eye.

In some embodiments, the holographic medium is coupled with a waveguide to receive the light provided from the light source and propagated through the waveguide (e.g., holographic medium 454 is coupled with waveguide 456 to receive light 402-1 in FIG. 4E). In some embodiments, the light propagates through the waveguide in a direction that is not parallel to the optical axis of the holographic medium (e.g., light 402-2 propagates in a direction not parallel to optical axis of holographic medium 454). In some embodiments, projecting, by the holographic medium, the plurality of separate light patterns concurrently toward the eye includes directing toward the eye at least a portion of the light propagated through the waveguide as the plurality of separate light patterns (e.g., light patterns 454-1 and 454-2). In some embodiments, the waveguide includes, or is coupled with, an in-coupling element (e.g., a prism or a diffractive or holographic structure), which is configured to in-couple the light into the waveguide in order to reach angles of total internal reflection (e.g., in-coupling device 452).

In accordance with some embodiments, a head-mounted display device includes one or more optical elements (e.g., one or more lenses 608), one or more displays (e.g., display 610 in FIG. 6A) configured to project light through the one or more lenses, and the eye-tracking system described herein (e.g., an eye-tracking system including detector 602, light source 402, and holographic medium 404). In some embodiments, the head-mounted display device renders augmented reality images (e.g., display device 640 renders augmented reality images as shown in FIG. 6D). In some embodiments, the head-mounted display device renders virtual reality images (e.g., display device 600 renders virtual reality images as shown in FIG. 6A).

In some embodiments, the holographic medium of the eye-tracking system is positioned adjacent to the one or more optical elements (e.g., in FIG. 6A, holographic medium 404 is positioned adjacent to one or more lenses 608).

In some embodiments, the light source of the eye-tracking system is positioned away from the one or more optical elements so that the light source does not occlude the one or more displays (e.g., in FIG. 6A, light source 402 is positioned away from one or more lenses 608). In some embodiments, the light source of the eye-tracking system is positioned off-axis from the one or more lenses (e.g., the light source of the eye-tracking system is positioned away from an optical axis of the one or more lenses). In some embodiments, the light source of the eye-tracking system is positioned so that the light source does not occlude the field of view provided by the one or more lenses and the one or more displays.

In some embodiments, the detector of the eye-tracking system is positioned away from the one or more optical elements so that the detector does not occlude the one or more displays. In some embodiments, the detector of the eye-tracking system is positioned off-axis from the one or more lenses. In some embodiments, the detector is positioned so that the light source does not occlude the field of view provided by the one or more lenses and the one or more displays.

In some embodiments, the eye-tracking system is configured to determine a location of a pupil of a first eye and the device includes a second eye-tracking system, that is distinct and separate from the eye-tracking system, configured to determine a location of a pupil of a second eye that is distinct from the first eye (e.g., in FIG. 6C, device 630 includes display device 600-A with a first eye-tracking system for eye 408-A and display device 600-B with a second eye-tracking system for eye 408-B).

In some embodiments, the device includes a combiner (e.g., combiner 644 in FIG. 6D) configured to combine the light from the one or more displays (e.g., light 642-1 from display 642) and light from an outside of the head-mounted display device (e.g., light 650) for providing an overlap of an image rendered by the light from the one or more displays and a real image that corresponds to the light from the outside of the head-mounted display device.

In accordance with some embodiments, a method for determining a location of a pupil of an eye includes providing light with a light source (e.g., light 402-1 provided by light source 402 in FIG. 6A), receiving, with a holographic medium (e.g., holographic medium 404 receives light 402-1) optically coupled with the light source, the light provided by the light source, and projecting, with the holographic medium, a plurality of separate light patterns concurrently toward an eye (e.g., holographic medium 404 projects light patterns 406-1, 406-2, and 406-3 toward eye 408). The method also includes detecting, with a detector, a reflection of at least a subset of the plurality of separate light patterns reflected off the eye of the wearer (e.g., detector 602 captures an image of at least a subset of light patterns 406-1, 406-2, and 406-3 reflected off a surface of eye 408). The method further includes determining, based on the reflection of at least the subset of the plurality of separate light patterns reflected off the eye, a location of a pupil of the eye. For example, as shown in Section B of FIG. 7A, in accordance with a determination that reflection of all of the plurality of separate light patterns is detected, it is determined that the pupil of the eye is located in a center position (also called a neutral position). In another example, as shown in Section A of FIG. 7A, in accordance with a determination that reflection of one or more light patterns of the plurality of separate light patterns is not detected or detected at a lower intensity, it is determined that the pupil of the eye is tilted (e.g., toward the one or more light patterns of the plurality of separate light patterns).

In some embodiments, determining the location of the pupil of the eye includes determining respective locations of at least the subset of the plurality of separate light patterns in the reflection (e.g., determining whether one or more glints are not detected, and/or which glints are not detected).

In some embodiments, determining the location of the pupil of the eye includes determining respective intensities of the plurality of separate light patterns in the reflection (e.g., determining whether one or more glints are detected at a lower intensity, such as an intensity below a predefined intensity threshold, and/or which glints are detected at a lower intensity).

In some embodiments, determining the location of the pupil of the eye includes determining a respective configuration of the plurality of separate light patterns in the reflection (e.g., determining the configuration of glints 706 in Section B of FIG. 7B).

In some implementations, a respective light pattern of the plurality of separate light patterns has a distinct combination of optical characteristics (e.g., color, shape, size, intensity, etc.). As a result, each light pattern is identifiable based on the combination of optical characteristics.

In accordance with some embodiments, a system for making a holographic medium includes a light source configured to provide light and a beam splitter configured to separate the light into a first portion of the light (e.g., beam 832-A in FIG. 8A) and a second portion of the light (e.g., beam 834-A in FIG. 8A) that is spatially separated from the first portion of the light. The system also includes a first set of optical elements (e.g., the first set of optical elements 800-A) configured to transmit the first portion of the light for providing a first wide-field beam onto an optically recordable medium (e.g., optically recordable medium 826 in FIG. 8A), a second set of optical elements (e.g., the second set of optical elements 800-B) configured to transmit the second portion of the light through for providing a second wide-field beam, and a plurality of lenses (e.g., lenses 820) optically coupled with the second set of optical elements configured to receive the second wide-field beam (e.g., beam 834-B) and project a plurality of separate light patterns (e.g., light patterns 836) onto the optically recordable medium (e.g., optically recordable medium 826) for forming the holographic medium.

In some embodiments, the plurality of lenses is arranged in a microlens array (e.g., in FIG. 9A, lenses 820 are arranged in a microlens array).

In some embodiments, the plurality of lenses is arranged in a circular configuration (e.g., lenses 820-3 are arranged in a circular configuration as shown in FIG. 9C). In some embodiments, the plurality of lenses includes seven or more lenses (e.g., between 7 and 20 lenses).

In some embodiments, the plurality of lenses is arranged in a rectangular configuration (e.g., lenses 820-2 are arranged in a rectangular configuration in FIG. 9B). In some embodiments, the plurality of lenses includes at least 20 lenses (e.g., between 20 and 1000 lenses).

In some embodiments, the plurality of lenses is positioned adjacent to the optically recordable medium (e.g., lenses 820 are adjacent to optically recordable medium 826 in FIG. 9A). In some embodiments, the plurality of lenses is positioned within 25 mm from the optically recordable medium. In some embodiments, the plurality of lenses is positioned within 10 mm from the optically recordable medium. In some embodiments, the plurality of lenses is positioned within 5 mm from the optically recordable medium.

In some embodiments, the system includes a condenser lens that is distinct from the plurality of lenses and optically coupled with the plurality of lenses (e.g., condenser lens 818 is optically coupled with lenses 820 in FIG. 9A). In some embodiments, the diameter of the condenser lens is at least 75 mm. In some embodiments, each lens of the plurality of lenses is configured to direct the second wide-field beam toward a reference pupil. For example, lens 818 directs beam 834-B toward reference pupil 903 in FIG. 9A. In some implementations, the position of reference pupil 903 corresponds to a position of eye 408 in FIG. 4A (e.g., an eye of a user of a display device, such as display device 600 in FIG. 6A).

In some embodiments, each lens of the plurality of lenses is configured to focus a respective portion of the second wide-field beam on a reference focal plane. The reference focal plane is located between the optically recordable medium and the reference pupil. As a result, when holographic medium 404 formed using the optically recordable medium is illuminated with light from light source 402 as shown in FIG. 4A, the holographic medium projects light toward reference focal plane 410-1 that is located between holographic medium 404 and the pupil of eye 408.

In some embodiments, the plurality of lenses includes a first lens configured to project a first light pattern of the plurality of separate light patterns onto the optically recordable medium at a first angle (e.g., lens 820-A projects light pattern 836-A onto optically recordable medium 826 at a first angle in FIG. 9A), and a second lens configured to project a second light pattern of the plurality of separate light patterns onto the optically recordable medium at a second angle that is distinct from the first angle (e.g., lens 820-B projects light pattern 836-B onto optically recordable medium 826 at a second angle in FIG. 9A). In some embodiments, the first angle is 45 degrees with respect to an optical axis of the holographic medium (e.g., an optical axis that is perpendicular to the holographic medium). In some embodiments, the second angle is 0 degrees with respect to the optical axis of the holographic medium.

In some embodiments, the system includes a plurality of attenuators optically coupled with the plurality of lenses and configured to attenuate intensity of light provided to respective lenses of the plurality of lenses (e.g., attenuators 904-A and 904-B in FIG. 9A).

In some embodiments, the plurality of attenuators includes a first attenuator optically coupled with a first lens of the plurality of lenses (e.g., attenuator 836-A optically coupled with lens 820-A in FIG. 9A) and configured to attenuate intensity of light (e.g., light pattern 836-A) provided to the first lens by a first attenuation factor (e.g., 10% attenuation or no attenuation) and a second attenuator optically coupled with a second lens (e.g., attenuator 836-B optically coupled with lens 820-B), that is distinct from the first lens, of the plurality of lenses and configured to attenuate intensity of light (e.g., light pattern 736-B) provided to the second lens by a second attenuation factor (e.g., 20% attenuation) that is distinct from the first attenuation factor.

In accordance with some embodiments, a method for making a holographic medium includes providing light from a light source and separating the light into a first portion of the light and a second portion of the light that is spatially separated from the first portion of the light. The method also includes transmitting the first portion of the light through a first set of optical elements to provide a first wide-field beam, transmitting the second portion of the light through a second set of optical elements to provide a second wide-field beam that is spatially separated from the first wide-field beam onto an optically recordable medium, and transmitting the second wide-field beam through a plurality of lenses to provide a plurality of separate light patterns. The method further includes concurrently projecting the first wide-field beam and the plurality of separate light patterns onto the optically recordable medium to form the holographic medium.

In some embodiments, the plurality of lenses is arranged in a microlens array.

In some embodiments, the method includes projecting the plurality of separate light patterns arranged in a circular configuration (e.g., FIG. 9C).

In some embodiments, the method includes projecting the plurality of separate light patterns arranged in a rectangular configuration (e.g., FIG. 9B).

In some embodiments, the method includes focusing the second wide-field beam onto a focal plane that is adjacent to the optically recordable medium (e.g., in FIG. 9A, lenses 820-1 focus light patterns 836 onto reference plane 902 adjacent to optically recordable medium 826). In some embodiments, the reference focal plane corresponds to a focal plane located between the holographic medium and an eye of a user of an eye tracker (e.g., reference plane 410-1 located between holographic medium 404 and eye 408 in FIG. 4A).

In some embodiments, the method includes transmitting the second wide-field beam (e.g., beam 834-B in FIG. 9A) through a condenser lens (e.g., lens 818) that is distinct from the plurality of lenses prior to transmitting the second wide-field beam through the plurality of lenses (e.g., lenses 820). In some embodiments, the condenser lens is configured to direct the second wide-field beam toward a reference pupil (e.g., reference pupil 903).

In some embodiments, the method includes focusing, with each lens of the plurality of lenses, a respective portion of the second wide-field beam on a reference focal plane (e.g., FIG. 9A). The reference focal plane is located between the optically recordable medium and the reference pupil. In some embodiments, the reference focal plane corresponds to a focal plane located between the holographic medium and an eye of a user of an eye tracker (e.g., FIG. 4A).

In some embodiments, the method includes projecting, with a first lens of the plurality of lenses, a first light pattern of the plurality of separate light patterns onto the optically recordable medium at a first angle, and projecting, with a second lens of the plurality of lenses, a second light pattern of the plurality of separate light patterns onto the optically recordable medium at a second angle that is distinct from the first angle (e.g., FIG. 9A). In some embodiments, the first angle is 55 degrees with respect to an optical axis of the holographic medium (e.g., an optical axis that is perpendicular to the holographic medium), and the second angle is 0 degrees.

In some embodiments, the method includes attenuating, with a first attenuator optically coupled with a first lens of the plurality of lenses, intensity of light provided to the first lens by a first attenuation factor (e.g., 10% attenuation or no attenuation) and attenuating, with a second attenuator optically coupled with a second lens, that is distinct from the first lens, of the plurality of lenses, intensity of light provided to the second lens by a second attenuation factor (e.g., 20% attenuation) that is distinct from the first attenuation factor (e.g., FIG. 9A).

In accordance with some embodiments, a holographic medium is made by the method described herein (e.g., holographic medium 404 in FIG. 4A).

In accordance with some embodiments, a system for making a holographic medium includes a light source configured to provide light, and a beam splitter configured to separate the light into a first portion of the light and a second portion of the light that is spatially separated from the first portion of the light. The system also includes a first set of optical elements (e.g., the first set of optical elements 800-A in FIG. 8A) configured to transmit the first portion of the light for providing a first wide-field beam onto an optically recordable medium, a second set of optical elements (e.g., the second set of optical elements 800-B) configured to transmit the second portion of the light for providing a second wide-field beam, and a plurality of prisms (e.g., prisms 912 in FIG. 9E) optically coupled with the second set of optical elements and configured to receive the second wide-field beam (e.g., beam 834-B) and project a plurality of separate light patterns onto the optically recordable medium for forming the holographic medium (e.g., light patterns 836 are projected by prisms 912 onto optically recordable medium 826 in FIG. 9G).

In some embodiments, the plurality of prisms is arranged in a circular configuration (e.g., prisms 912 in FIG. 9E are arranged in a circular configuration illustrated in FIG. 9C).

In some embodiments, the plurality of prisms is arranged in a rectangular configuration (e.g., prisms 912 in FIG. 9E are arranged in a rectangular configuration illustrated in FIG. 9B).

In some embodiments, the plurality of prisms is positioned adjacent to the optically recordable medium (e.g., prisms 912 are positioned adjacent to optically recordable medium 826 in FIG. 9E).

In some embodiments, the system includes a plurality of lenses that is optically coupled with the plurality of prisms (e.g., lenses 921 are optically coupled with prisms 912 in FIG. 9E). For example, the system includes a first lens that is optically coupled with a first prism of the plurality of prisms (e.g., lens 921-A is optically coupled with prism 912-A), and a second lens that is distinct from the first lens and optically coupled with a second prism of the plurality of prisms that is distinct and separate from the first prism (e.g., lens 921-B is optically coupled with prism 912-B). In some embodiments, the plurality of lenses is arranged in a micro-lens array.

In some embodiments, each lens of the plurality of lenses is configured to focus a respective portion of the second wide-field beam on a reference focal plane, and the reference focal plane is located between the optically recordable medium and a reference pupil (e.g., lenses 921 focus light patterns 836 on reference plane 902 in FIG. 9G).

In some embodiments, the plurality of prisms includes a first prism configured to project a first light pattern of the plurality of separate light patterns onto the optically recordable medium at a first angle, and a second prism configured to project a second light pattern of the plurality of separate light patterns onto the optically recordable medium at a second angle that is distinct from the first angle (e.g., FIG. 9G).

In some embodiments, the first prism is located at a first distance from the optically recordable medium (e.g., distance D1 in FIG. 9E) and the second prism is located at a second distance from the optically recordable medium (e.g., distance D2). The second distance is distinct from the first distance (e.g., distance D2 is greater than distance D1).

In some embodiments, the plurality of prisms is arranged in a dome configuration (e.g., prisms 912 are arranged in a dome configuration as shown in FIG. 9F). In some embodiments, the plurality of prisms is arranged in a dome configuration (e.g., 12 prisms are arranged in concentric circles, where 4 prisms are arranged to form an inner circle and 8 prisms are arranged to form an outer circle). In some implementations, the outermost prisms direct light onto the optically recordable medium at a 45-degree angle. The angle is defined with respect to an optical axis of the optically recordable medium (e.g., directions of light patterns 836 in FIG. 9G correspond to the directions of light patterns 406-1 and 406-2 in FIG. 4D).

In some embodiments, the system includes a plurality of attenuators optically coupled with the plurality of prisms and configured to attenuate intensity of light provided by respective prisms of the plurality of prisms (e.g., attenuators 904-A and 904-B described with respect to FIG. 9A are coupled with prisms 912 in FIG. 9E).

In some embodiments, the plurality of attenuators includes a first attenuator (e.g., attenuator 904-A in FIG. 9A) optically coupled with a first prism of the plurality of prisms (e.g., prism 912-A in FIG. 9E) and configured to attenuate intensity of light provided by the first prism by a first attenuation factor and a second attenuator (e.g., attenuator 904-B in FIG. 9A) optically coupled with a second prism (e.g., prism 912-B), that is distinct from the first prism, of the plurality of prisms and configured to attenuate intensity of light provided by the second prism by a second attenuation factor that is distinct from the first attenuation factor.

In some embodiments, the system includes a condenser lens coupled with the plurality of prisms (e.g., condenser lens 818 described with respect to FIG. 9A is coupled with prisms 912 shown in FIG. 9E).

In accordance with some embodiments, a method for making a holographic medium includes providing light from a light source, and separating the light into a first portion of the light and a second portion of the light that is spatially separated from the first portion of the light (e.g., FIG. 8A). The method also includes transmitting the first portion of the light through a first set of optical elements to provide a first wide-field beam (e.g., FIG. 8A), transmitting the second portion of the light through a second set of optical elements to provide a second wide-field beam that is spatially separated from the first wide-field beam onto an optically recordable medium (e.g., FIG. 8A), and transmitting the second wide-field beam through a plurality of prisms to provide a plurality of separate light patterns (e.g., FIG. 9G). The method further includes concurrently projecting the first wide-field beam and the plurality of separate light patterns onto the optically recordable medium to form the holographic medium.

In some embodiments, the plurality of prisms is optically coupled with a plurality of lenses (e.g., FIG. 9G).

In some embodiments, the method includes transmitting the second wide-field beam through the plurality of lenses (e.g., FIG. 9G).

In some embodiments, in some embodiments, the plurality of lenses is configured to direct the second wide-field beam toward a reference pupil (e.g., analogous to the configuration shown in FIG. 9A).

In some embodiments, the method includes focusing, with each lens of the plurality of lenses, a respective portion of the second wide-field beam on a reference focal plane, the reference focal plane located between the optically recordable medium and the plurality of lenses. For example, the reference focal plane is located between the holographic medium and an eye of a user of an eye tracker (e.g., analogous to the configuration shown in FIG. 9A).

In some embodiments, the method includes projecting, with a first prism of the plurality of prisms, a first light pattern of the plurality of separate light patterns onto the optically recordable medium at a first angle, and projecting, with a second prism of the plurality of prisms, a second light pattern of the plurality of separate light patterns onto the optically recordable medium at a second angle that is distinct from the first angle (e.g., FIG. 9G). For example, the first angle is 45 degrees with respect to an optical axis of the holographic medium (e.g., an optical axis that is perpendicular to the holographic medium) and the second angle is 30 degrees with respect to the optical axis of the holographic medium.

In some embodiments, the first prism is located at a first distance from the optically recordable medium and the second prism is located at a second distance from the optically recordable medium, the second distance being distinct from the first distance (e.g., FIG. 9E).

In some embodiments, the method includes projecting the plurality of separate light patterns arranged in a circular configuration (e.g., prisms 912 in FIG. 9E are arranged in a circular configuration illustrated in FIG. 9C for projecting light patterns arranged in a circular configuration).

In accordance with some embodiments, a holographic medium is made by the method described herein (e.g., holographic medium 404 in FIG. 4A).

In accordance with some embodiments, a system for making a holographic medium includes a light source configured to provide light and a beam splitter configured to separate the light into a first portion of the light and a second portion of the light that is spatially separated from the first portion of the light (e.g., FIG. 8A). The system also includes a first set of optical elements configured to transmit the first portion of the light for providing a first wide-field beam onto an optically recordable medium (e.g., FIG. 8A), a second set of optical elements configured to transmit the second portion of the light for providing a second wide-field beam (e.g., FIG. 8A), and a plurality of parabolic reflectors (e.g., parabolic reflectors 922 in FIG. 9H) optically coupled with the second set of optical elements and configured to receive the second wide-field beam (e.g., beam 834-B in FIG. 9H) and project a plurality of separate light patterns (e.g., light patterns 836) onto the optically recordable medium (e.g., optically recordable medium 826) for forming the holographic medium.

In some embodiments, the plurality of parabolic reflectors is arranged in a circular configuration (e.g., parabolic reflectors 922 in FIG. 9H are arranged in a circular configuration illustrated in FIG. 9C). In some embodiments, the plurality of parabolic reflectors includes seven or more parabolic reflectors (e.g., between 7 and 20 parabolic reflectors).

In some embodiments, the plurality of parabolic reflectors is arranged in a rectangular configuration (e.g., parabolic reflectors 922 in FIG. 9H are arranged in a rectangular configuration illustrated in FIG. 9B). In some embodiments, the plurality of parabolic reflectors includes at least 20 parabolic reflectors (e.g., between 20 and 1000 parabolic reflectors).

In some embodiments, each parabolic reflector of the plurality of parabolic reflectors is configured to focus a respective portion of the second wide-field beam on a reference focal plane (e.g., parabolic reflectors 922 focus light patterns 836 on reference plane 902 in FIG. 9H).

In some embodiments, the reference focal plane is located between the optically recordable medium and a reference pupil. For example, the reference focal plane is located between the holographic medium and an eye of a user of an eye tracker (e.g., reference plane 410-1 located between holographic medium 404 and eye 408 in FIG. 4A). In some embodiments, the reference focal plane is located on one side of the optically recordable medium that is opposite to the plurality of parabolic reflectors. For example, the optically recordable medium is located between the plurality of parabolic reflectors and the reference focal plane.

In some embodiments, the plurality of parabolic reflectors includes a first parabolic reflector configured to project a first light pattern of the plurality of separate light patterns onto the optically recordable medium at a first angle (e.g., parabolic reflector 922-A projects light pattern 836-A at a first angle in FIG. 9H), and a second parabolic reflector configured to project a second light pattern of the plurality of separate light patterns onto the optically recordable medium at a second angle that is distinct from the first angle (e.g., parabolic reflector 922-B projects light pattern 836-B at a second angle).

In some embodiments, the first parabolic reflector has a first surface profile and the second parabolic reflector has a second surface profile distinct from the first surface profile (e.g., in FIG. 9I, parabolic reflector 922-C has a surface profile that is distinct from surface profile 922-A).

In some embodiments, the system includes a plurality of attenuators optically coupled with the plurality of parabolic reflectors and configured to attenuate intensity of light provided by respective parabolic reflectors of the plurality of parabolic reflectors (e.g., parabolic reflectors 922-A and 922-B in FIG. 9H are optically coupled with attenuators 904-A and 904-B shown in FIG. 9A).

In some embodiments, the plurality of attenuators includes a first attenuator (e.g., attenuator 904-A in FIG. 9A) optically coupled with a first parabolic reflector of the plurality of parabolic reflectors (e.g., parabolic reflector 922-A) and configured to attenuate intensity of light provided by the first parabolic reflector (e.g., light pattern 836-A) by a first attenuation factor (e.g., 10% or zero attenuation) and a second attenuator (e.g., attenuator 904-B in FIG. 9A) optically coupled with a second parabolic reflector (e.g., parabolic reflector 922-B), that is distinct from the first parabolic reflector, of the plurality of parabolic reflectors and configured to attenuate intensity of light provided by the second parabolic reflector (e.g., light pattern 836-B) by a second attenuation factor (e.g., 20% attenuation) that is distinct from the first attenuation factor.

In some embodiments, the system includes one or more lenses coupled with the plurality of parabolic reflectors (e.g., lenses 924 in FIG. 9I). In some embodiments, lenses 924 are arranged in a microlens array. In some embodiments, lenses 924 are replaced by a single condenser lens (e.g., lens 936 in FIG. 9K).

In accordance with some embodiments, a method for making a holographic medium includes providing light from a light source, and separating the light into a first portion of the light and a second portion of the light that is spatially separated from the first portion of the light (e.g., FIG. 8A). The method also includes transmitting the first portion of the light through a first set of optical elements to provide a first wide-field beam (e.g., FIG. 8A), transmitting the second portion of the light through a second set of optical elements to provide a second wide-field beam that is spatially separated from the first wide-field beam onto an optically recordable medium (e.g., FIG. 8A), and reflecting the second wide-field beam with a plurality of parabolic reflectors to provide a plurality of separate light patterns (e.g., reflecting wide-field beam 836-A with parabolic reflectors 922 as light patterns 836 as shown in FIG. 9H). The method further includes concurrently projecting the first wide-field beam and reflecting the plurality of separate light patterns onto the optically recordable medium to form the holographic medium (e.g., projecting wide-field beam 832-B and light patterns 836 concurrently onto optically recordable medium 826 in FIG. 9H).

In some embodiments, the plurality of parabolic reflectors is arranged in a circular configuration (e.g., FIG. 9C).

In some embodiments, the method includes projecting the plurality of separate light patterns arranged in a circular configuration (e.g., parabolic reflectors 922 in FIG. 9H are arranged in a circular configuration illustrated in FIG. 9C for projecting light patterns arranged in a circular configuration).

In some embodiments, the plurality of parabolic reflectors is arranged in a rectangular configuration (e.g., FIG. 9B).

In some embodiments, the method includes projecting the plurality of separate light patterns arranged in a rectangular configuration (e.g., parabolic reflectors 922 in FIG. 9H are arranged in a rectangular configuration for projecting light patterns arranged in a rectangular configuration illustrated in FIG. 9B).

In some embodiments, the method includes focusing the second wide-field beam onto a focal plane that is adjacent to the optically recordable medium (e.g., FIG. 9H).

In some embodiments, the method includes focusing, with each parabolic reflector of the plurality of parabolic reflectors, a respective portion of the second wide-field beam on a reference focal plane, the reference focal plane located between the optically recordable medium and a reference pupil. For example, the reference focal plane is located between the holographic medium and an eye of a user of an eye tracker (e.g., reference plane 902 corresponds to reference plane 410-1 FIG. 4A).

In some embodiments, the method includes projecting, with a first parabolic reflector of the plurality of parabolic reflectors, a first light pattern of the plurality of separate light patterns onto the optically recordable medium at a first angle, and projecting, with a second parabolic reflector of the plurality of parabolic reflectors, a second light pattern of the plurality of separate light patterns onto the optically recordable medium at a second angle that is distinct from the first angle (e.g., FIG. 9H). For example, the first angle is 45 degrees with respect to an optical axis of the holographic medium (e.g., an optical axis that is perpendicular to the holographic medium), and the second angle is 20 degrees with respect to the optical axis of the holographic medium.

In some embodiments, the method includes attenuating, with a first attenuator optically coupled with a parabolic reflector of the plurality of parabolic reflectors, intensity of light provided to the first parabolic reflectors by a first attenuation factor (e.g., 10% or no attenuation) and attenuating, with a second attenuator optically coupled with a second parabolic reflector, that is distinct from the first parabolic reflector, of the plurality of parabolic reflectors, intensity of light provided to the second parabolic reflectors by a second attenuation factor (e.g., 20% attenuation) that is distinct from the first attenuation factor (e.g., attenuators 904-A and 904-B in FIG. 9A optically coupled with parabolic reflectors 836-A and 836-B in FIG. 9H).

In accordance with some embodiments, a holographic medium is made by the method described herein (e.g., holographic medium 404 in FIG. 4A).

In accordance with some embodiments, a system for making a holographic medium includes a light source configured to provide light and a beam splitter configured to separate the light into a first portion of the light and a second portion of the light that is spatially separated from the first portion of the light (e.g., FIG. 8A). The system also includes a first set of optical elements configured to transmit the first portion of the light for providing a first wide-field beam onto an optically recordable medium (e.g., FIG. 8A) and one or more diffractive optical elements configured to receive the second portion of the light and project a plurality of separate light patterns onto the optically recordable medium for forming the holographic medium (e.g., in FIG. 9K, DOE 934 receives beam 834-D and projects it as light patterns, such as light patterns 932-A and 932-B, onto optically recordable medium 826).

In some embodiments, the light provided by the light source is coherent light (e.g., light source 802 provides coherent light in FIG. 8A).

In some embodiments, the one or more diffractive optical elements are configured to project a first light pattern (e.g., light pattern 932-A in FIG. 9K) of the plurality of separate light patterns onto the optically recordable medium at a first angle (e.g., 15 degrees), and project a second light pattern (e.g., light pattern 932-B) of the plurality of separate light patterns onto the optically recordable medium at a second angle (e.g., 0 degrees) that is distinct from the first angle.

In some embodiments, the one or more diffractive optical elements are optically coupled with one or more lenses configured to focus light from the one or more diffractive optical elements (e.g., in FIG. 9K, DOE 934 is coupled with lens 936).

In some embodiments, the one or more lenses are configured to focus the light from the one or more diffractive optical elements on a reference focal plane located between the optically recordable medium and a reference pupil.

In some embodiments, the one or more diffractive optical elements include one or more diffractive beam splitters configured to project an array of spots (e.g., DOE 934 in FIG. 9K includes one or more diffractive beam splitters forming a plurality of light patterns shown in FIG. 9B).

In some embodiments, the one or more diffractive optical elements include one or more diffractive diffusers (e.g., DOE 934 in FIG. 9K includes one or more diffractive diffusers).

In some embodiments, the one or more diffractive optical elements (e.g., DOE 934 in FIG. 9K) are optically coupled with a plurality of lenses (e.g., lens 936 in FIG. 9A is replaced with lenses 820-1 in FIG. 9A), a first lens of the plurality of lenses configured to focus a first portion of light from the one or more diffractive optical elements (e.g., light pattern 932-A) and a second lens of the plurality of lenses configured to focus a second portion (e.g., light pattern 932-B), distinct from the first portion, of light from the one or more diffractive optical elements.

In some embodiments, the plurality of lenses is arranged in a microlens array (e.g., lenses 820-1 in FIG. 9A are arranged in a microlens array).

In some embodiments, the system includes one or more diffusers configured to diffuse light from the one or more diffractive optical elements (e.g., diffuser 938 diffuses light patterns 932-A and 932-B in FIG. 9K).

In some embodiments, the plurality of separate light patterns is arranged in a circular configuration (e.g., DOE 934 projects light patterns, such as light patterns 932-A and 932-B, in a circular configuration).

In some embodiments, the plurality of separate light patterns is arranged in a rectangular configuration (e.g., DOE 934 projects light patterns, such as light patterns 932-A and 932-B, in a rectangular configuration).

In some embodiments, the system includes a second set of optical elements configured to direct the second portion of the light toward the one or more diffractive optical elements (e.g., the second set of optical elements 800-B in FIG. 8A directs beam 834-D in FIG. 9K toward DOE 934).

In accordance with some embodiments, a method for making a holographic medium includes providing light from a light source and separating the light into a first portion of the light and a second portion of the light that is spatially separated from the first portion of the light (e.g., FIG. 8A). The method also includes transmitting the first portion of the light through a first set of optical elements to provide a first wide-field beam (e.g., FIG. 8A), transmitting the second portion of the light through one or more diffractive optical elements to provide a plurality of separate light patterns (e.g., FIG. 9K), and concurrently projecting the first wide-field beam and the plurality of separate light patterns onto the optically recordable medium to form the holographic medium (e.g., FIG. 8A).

In some embodiments, the method includes focusing, with one or more lenses, light from the one or more diffractive optical elements (e.g., FIG. 9K).

In some embodiments, the light from the one or more diffractive optical elements is focused by the one or more lenses onto a reference focal plane located between the optically recordable medium and a reference pupil.

In some embodiments, the method includes projecting the one or more diffractive optical elements, a first light pattern of the plurality of separate light patterns onto the optically recordable medium at a first angle, and projecting, with the one or more diffractive optical elements, a second light pattern of the plurality of separate light patterns onto the optically recordable medium at a second angle that is distinct from the first angle (e.g. FIG. 9K).

In some embodiments, the method includes directing, with a second set of optical elements, the second portion of the light toward the one or more diffractive optical elements (e.g., FIG. 8A).

In some embodiments, the method includes diffusing, with one or more diffusers, light from the one or more diffractive optical elements (e.g., FIG. 9K).

In accordance with some embodiments, a holographic medium is made by the method described herein (e.g., holographic medium 404 in FIG. 4A).

In accordance with some embodiments, a system for making a holographic medium, includes a light source configured to provide light and a beam splitter configured to separate the light into a first portion of the light and a second portion of the light that is spatially separated from the first portion of the light (e.g., FIG. 8A). The system also includes a first set of optical elements configured to transmit the first portion of the light for providing a first wide-field beam onto an optically recordable medium (e.g., FIG. 8A) and a plurality of optical fibers configured to receive the second portion of the light and project a plurality of separate light patterns onto the optically recordable medium for forming the holographic medium (e.g., optical fibers 944 receive beam 834-A and project light patterns 942 onto optically recordable medium 826 in FIG. 9L).

In some embodiments, the light provided by the light source is coherent light (e.g., light source 802 provides coherent light in FIG. 8A).

In some embodiments, each optical fiber of the plurality of optical fibers includes a first optical fiber end optically coupled with the light source (e.g., input fiber end 948-1 in FIG. 9L) and a second optical fiber end (e.g., output fiber end 948-2), opposite to the first optical fiber end, configured to provide a respective light pattern of the plurality of separate light patterns (e.g., light patterns 942). In some embodiments, the optical fibers are single-mode fibers. In some embodiments, the plurality of optical fibers is optically coupled with the light source by a single fiber (e.g., optical fiber 946). For example, a single optical fiber is split into a plurality of optical fibers 944.

In some embodiments, respective second optical fiber ends of the plurality of optical fibers are arranged in a circular configuration (e.g., respective output fiber ends 948-2 of optical fibers 942 are arranged in a circular configuration illustrated in FIG. 9C).

In some embodiments, respective second optical fiber ends of the plurality of optical fibers are arranged in a rectangular configuration (e.g., respective output ends 948-2 of optical fibers 942 are arranged in a rectangular configuration illustrated in FIG. 9B).

In some embodiments, respective second fiber ends of the plurality of optical fibers are positioned adjacent to the optically recordable medium (e.g., output fiber ends 948-2 are positioned adjacent to optically recordable medium 826 in FIG. 9L).

In some embodiments, the plurality of optical fibers includes a first optical fiber configured to project a first light pattern of the plurality of separate light patterns onto the optically recordable medium at a first angle (e.g., optical fiber 944-A projects light pattern 942-A onto optically recordable medium 826 at a first angle in FIG. 9L, such as 30 degrees), and a second optical fiber configured to project a second light pattern of the plurality of separate light patterns onto the optically recordable medium at a second angle that is distinct from the first angle (e.g., optical fiber 944-B projects light pattern 942-B onto optically recordable medium 826 at a second angle, such as 20 degrees).

In some embodiments, the plurality of optical fibers is coupled with a plurality of lenses (e.g., lenses 950 in FIG. 9L).

In some embodiments, the plurality of lenses is arranged in a microlens array (e.g., lenses 950 are arranged in a microlens array).

In some embodiments, each lens of the plurality of lenses is configured to focus a respective light pattern of the plurality of separate light patterns on a reference focal plane, the reference focal plane located between the optically recordable medium and a reference pupil.

In some embodiments, the plurality of optical fibers is coupled with a condenser lens (e.g., lenses 950 in FIG. 9L are replaced with a single condenser lens, such as lens 936 in FIG. 9K, or a condenser lens is used in conjunction with lenses 950). In some embodiments, the condenser lens is configured to focus the plurality of separate light patterns on a reference focal plane, the reference focal plane located between the optically recordable medium and a reference pupil.

In some embodiments, the system includes a second set of optical elements configured to couple the second portion of the light into the plurality of optical fibers (e.g., the second set of optical elements 800-B in FIG. 8A couples beam 834-A to optical fibers 944 in FIG. 9K).

In some embodiments, the system includes a plurality of optical filters (e.g., filters 952 in FIG. 9L) optically coupled with the plurality of optical fibers and configured to modify a color of the light provided by respective optical fibers of the plurality of optical fibers.

In some embodiments, the system includes a plurality of attenuators optically coupled with the plurality of optical fibers and configured to attenuate intensity of light provided by respective optical fibers of the plurality of optical fibers (e.g., attenuators 904-A and 904-B in FIG. 9A are coupled with respective optical fibers 944-A and 944-B in FIG. 9B).

In accordance with some embodiments, a method for making a holographic medium includes providing light from a light source and separating the light into a first portion of the light and a second portion of the light that is spatially separated from the first portion of the light (e.g., FIG. 8A). The method also includes transmitting the first portion of the light through a first set of optical elements to provide a first wide-field beam (e.g., FIG. 8A), transmitting the second portion of the light through a plurality of optical fibers to provide a plurality of separate light patterns (e.g., FIG. 9L), and concurrently projecting the first wide-field beam and the plurality of separate light patterns onto the optically recordable medium to form the holographic medium (e.g., FIG. 8A).

In some embodiments, the method includes projecting the plurality of separate light patterns arranged in a circular configuration (e.g., optical fibers 944 project light patterns 942 in FIG. 9L in a circular configuration).

In some embodiments, the method includes projecting the plurality of separate light patterns arranged in a rectangular configuration (e.g., optical fibers 944 project light patterns 942 in FIG. 9L in a rectangular configuration).

In some embodiments, the method includes focusing, with a plurality of lenses coupled with the plurality of optical fibers, the plurality of separate light patterns onto a focal plane that is adjacent to the optically recordable medium (e.g., lenses 950 focus light patterns 924-A and 942-B in FIG. 9A on a reference plane, such as reference plane 902 in FIG. 9A).

In some embodiments, the plurality of lenses is arranged in a microlens array (e.g., lenses 950 in FIG. 9A).

In some embodiments, the method includes focusing, with a condenser lens coupled with the plurality of optical fibers (e.g., lens 936 in FIG. 9K is coupled with optical fibers 944 in FIG. 9L), the plurality of separate light patterns onto a focal plane that is adjacent to the optically recordable medium (e.g., light patterns 924 in FIG. 9L are focused on a reference plane, such as reference plane 902 in FIG. 9A).

In some embodiments, the method includes projecting, with a first optical fiber of the plurality of optical fibers, a first light pattern of the plurality of separate light patterns onto the optically recordable medium at a first angle, and projecting, with a second optical fiber of the plurality of optical fibers, a second light pattern of the plurality of separate light patterns onto the optically recordable medium at a second angle that is distinct from the first angle (e.g., FIG. 9L).

In accordance with some embodiments, a holographic medium is made by the method described herein (e.g., holographic medium 404 in FIG. 4A).

Although various drawings illustrate operations of particular components or particular groups of components with respect to one eye, a person having ordinary skill in the art would understand that analogous operations can be performed with respect to the other eye or both eyes. For brevity, such details are not repeated herein.

Although some of various drawings illustrate a number of logical stages in a particular order, stages which are not order dependent may be reordered and other stages may be combined or broken out. While some reordering or other groupings are specifically mentioned, others will be apparent to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:

1. An eye-tracking system, comprising:
a holographic illuminator that includes:
a light source configured to provide light; and
a holographic medium optically coupled with the light source, the holographic medium configured to:
receive the light provided from the light source; and
project a plurality of separate light patterns having a common wavelength range concurrently toward an eye; and
a detector configured to detect a reflection of at least a subset of the plurality of separate light patterns, reflected off the eye, for determining a location of a pupil of the eye.

2. The eye-tracking system of claim 1, wherein:
the light source is a single-point light source.

3. The eye-tracking system of claim 1, wherein:
the light source is located away from an optical axis of the holographic medium.

4. The eye-tracking system of claim 1, wherein:
the holographic medium is a reflection holographic medium configured to receive the light from the light source on a first surface of the holographic medium and concurrently project the plurality of separate light patterns through the first surface of the holographic medium.

5. The eye-tracking system of claim 1, wherein:
the holographic medium is a transmitting holographic medium configured to receive the light from the light source on a first surface of the holographic medium and concurrently project the plurality of separate light patterns through a second surface of the holographic medium that is opposite to the first surface of the holographic medium.

6. The eye-tracking system of claim 1, wherein:
the plurality of separate light patterns includes a first light pattern and a second light pattern distinct and separate from the first light pattern; and
the first light pattern of the plurality of separate light patterns is projected toward the eye at a first angle and the second light pattern of the plurality of separate light patterns is projected toward the eye at a second angle distinct from the first angle.

7. The eye-tracking system of claim 1, wherein:
the plurality of separate light patterns is arranged in a circular configuration.

8. The eye-tracking system of claim 7, wherein:
the plurality of separate light patterns arranged in the circular configuration is configured to illuminate an area with a diameter of at least 10 mm on a surface of the eye.

9. The eye-tracking system of claim 1, wherein:
the plurality of separate light patterns is arranged in a distorted configuration that counters for a contoured surface of the eye so that the at least a subset of the plurality of separate light patterns reflected off the contoured surface of the eye is arranged in a non-distorted configuration.

10. The eye-tracking system of claim 1, wherein:
the holographic medium is configured to project the plurality of separate light patterns concurrently so that each light pattern of the plurality of separate light patterns converges in proximity to a surface of the eye.

11. A head-mounted display device, comprising:
one or more optical elements;
one or more displays configured to project light through or off of the one or more optical elements; and
the eye-tracking system of claim 1.

12. The device of claim 11, wherein:
the holographic medium of the eye-tracking system is positioned adjacent to the one or more optical elements.

13. The device of claim 11, wherein:
the light source of the eye-tracking system is positioned away from the one or more optical elements so that the light source does not occlude the one or more displays; and/or
the detector of the eye-tracking system is positioned away from the one or more optical elements so that the detector does not occlude the one or more displays.

14. The device of claim 11, wherein:
the eye-tracking system is configured to determine a location of a pupil of a first eye; and
the device includes a second eye-tracking system, that is distinct and separate from the eye-tracking system, configured to determine a location of a pupil of a second eye that is distinct from the first eye.

15. The device of claim 11, including:
a combiner configured to combine the light from the one or more displays and light from an outside of the head-mounted display device for providing an overlap of an image rendered by the light from the one or more displays and a real image that corresponds to the light from the outside of the head-mounted display device.

16. An eye-tracking system, comprising:
a holographic illuminator that includes:
a light source configured to provide light; and
a holographic medium optically coupled with the light source, the holographic medium configured to:
receive the light provided from the light source; and
project a plurality of separate light patterns concurrently toward an eye; and
a detector configured to detect a reflection of at least a subset of the plurality of separate light patterns, reflected off the eye, for determining a location of a pupil of the eye, wherein:
the holographic medium is coupled with a waveguide to receive the light provided from the light source and propagated through the waveguide; and,
projecting, by the holographic medium, the plurality of separate light patterns concurrently toward the eye includes directing toward the eye at least a portion of the light propagated through the waveguide as the plurality of separate light patterns.

17. A method for determining a location of a pupil of an eye of a wearer, the method comprising:
providing, with a light source, light;
receiving, with a holographic medium optically coupled with the light source, the light provided by the light source;
projecting, with the holographic medium, a plurality of separate light patterns having a common wavelength range concurrently toward an eye;
detecting, with a detector, a reflection of at least a subset of the plurality of separate light patterns reflected off the eye of the wearer; and
determining, based on the reflection of at least the subset of the plurality of separate light patterns reflected off the eye, a location of a pupil of the eye.

18. The method of claim 17, wherein determining the location of the pupil of the eye includes determining respective locations of at least the subset of the plurality of separate light patterns in the reflection.

19. The method of claim 17, wherein determining the location of the pupil of the eye includes determining respective intensities of the plurality of separate light patterns in the reflection.

20. The method of claim 17, wherein determining the location of the pupil of the eye includes determining a respective configuration of the plurality of separate light patterns in the reflection.

* * * * *